United States Patent
Ivanova et al.

(10) Patent No.: US 10,420,822 B2
(45) Date of Patent: Sep. 24, 2019

(54) COMPOSITIONS AND METHODS TO PREVENT AND TREAT BIOFILMS

(71) Applicant: ZIOLASE, LLC, Winter Springs, FL (US)

(72) Inventors: Svetlana A. Ivanova, Winter Springs, FL (US); Dennis W. Davis, Palm Bay, FL (US); Brad W. Arenz, Orlando, FL (US); Thomas K. Connellan, Charlottesville, FL (US)

(73) Assignee: ZIOLASE, LLC, Winter Springs, FL (US)

( * ) Notice: Subject to any disclaimer, the term of this patent is extended or adjusted under 35 U.S.C. 154(b) by 208 days.

(21) Appl. No.: 15/632,618

(22) Filed: Jun. 26, 2017

(65) Prior Publication Data

US 2017/0312345 A1 Nov. 2, 2017

Related U.S. Application Data

(63) Continuation-in-part of application No. 13/481,787, filed on May 26, 2012, now abandoned.
(Continued)

(51) Int. Cl.
*C12N 9/24* (2006.01)
*A61K 38/47* (2006.01)
(Continued)

(52) U.S. Cl.
CPC .............. *A61K 38/47* (2013.01); *A01N 63/00* (2013.01); *A01N 63/02* (2013.01); *A61K 8/66* (2013.01);
(Continued)

(58) Field of Classification Search
None
See application file for complete search history.

(56) References Cited

U.S. PATENT DOCUMENTS 5,593,869 A    1/1997  Kitahata et al.
6,759,040 B1   7/2004  Manyak
(Continued)

FOREIGN PATENT DOCUMENTS

EP    1068871    1/2001
EP    1081232    3/2001
(Continued)

OTHER PUBLICATIONS

Ostergaard et al., "Industrial Applications of Fungal Enzymes," Industrial Applications, 2nd Edition, The Mycota X, M. Hofrichter (Ed.); 2010; pp. 269-290.
(Continued)

*Primary Examiner* — Renee Claytor
*Assistant Examiner* — Trent R Clarke
(74) *Attorney, Agent, or Firm* — Allen, Dyer, Doppelt + Gilchrist, P.A.

(57) ABSTRACT

Compositions and methods to treat biofilms are disclosed based on the discovery of the role of the disaccharide trehalose in microbial biofilm development. In various embodiments to treat body-borne biofilms systemically and locally, the method includes administering trehalase, the enzyme which degrades trehalose, in combination with other saccharidases for an exposition time sufficient to adequately degrade the biofilm gel matrix at the site of the biofilm. The method also includes administering a combination of other enzymes such as proteolytic, fibrinolytic, and lipolytic enzymes to break down proteins and lipids present in the biofilm, and administering antimicrobials for the specific type(s) of infectious pathogen(s) underlying the biofilm. Additionally, methods are disclosed to address degradation of biofilms on medical device surfaces and biofilms present in industrial settings.

10 Claims, 12 Drawing Sheets

Related U.S. Application Data

(60) Provisional application No. 61/520,654, filed on Jun. 13, 2011.

(51) Int. Cl.
*A01N 63/00* (2006.01)
*A61K 9/00* (2006.01)
*A61K 9/70* (2006.01)
*A61Q 11/00* (2006.01)
*A61K 8/66* (2006.01)
*A01N 63/02* (2006.01)
*A61P 31/04* (2006.01)
*A61K 38/14* (2006.01)
*A61K 31/496* (2006.01)
*A61K 31/546* (2006.01)
*A61K 31/7036* (2006.01)

(52) U.S. Cl.
CPC ............ *A61K 9/006* (2013.01); *A61K 9/7007* (2013.01); *A61K 31/496* (2013.01); *A61K 31/546* (2013.01); *A61K 31/7036* (2013.01); *A61K 38/14* (2013.01); *A61P 31/04* (2018.01); *A61Q 11/00* (2013.01); *C12N 9/2405* (2013.01); *C12Y 302/01028* (2013.01); *Y10T 29/49826* (2015.01)

(56) References Cited

U.S. PATENT DOCUMENTS

| | | |
|---|---|---|
| 2006/0121019 A1 | 6/2006 | Budny |
| 2009/0202516 A1 | 8/2009 | Olmstead |
| 2011/0129454 A1 | 6/2011 | Olmstead |
| 2012/0315260 A1 | 12/2012 | Ivanova et al. |

FOREIGN PATENT DOCUMENTS

| | | |
|---|---|---|
| EP | 0820516 | 3/2002 |
| JP | H07-051063 | 2/1995 |
| JP | 2000508175 | 7/2000 |
| JP | 2001-519404 | 10/2001 |
| JP | 2003-061651 | 3/2003 |
| JP | 2009542618 | 12/2009 |
| JP | 2010527335 | 8/2010 |
| WO | 9738122 | 10/1997 |
| WO | 97/42326 | 11/1997 |
| WO | 9918999 | 4/1999 |
| WO | 2006/032011 | 3/2006 |
| WO | 2008004128 A2 | 1/2008 |
| WO | 2008141416 A1 | 11/2008 |

OTHER PUBLICATIONS

Japanese Patent Office, Printing or Correction by Regulation of Patent Law Article 17bis, Amendment of JP2010-527335, May 17, 2012, 7 pages. ****See Priority U.S. Appl. No. 13/481,787, filed May 26, 2012.
NPL pdf document "Sigma Trehalase T8778"—enzyme assay protocol for Sigma product 18778, Trehalase from porcine kidney ****See Priority U.S. Appl. No. 13/481,787, filed May 26, 2012.
Zheng et al. "Substrate cycles in Penicillium chrysogenum quantified by isotopic non-stationary flux analysis" 2012, Microbial Cell Factories, vol. 11 :140, pp. 1-14 ****See Priority U.S. Appl. No. 13/481,787, filed May 26, 2012.
Sansing et al. "Virus Particles from Conidia of *Penicillium* Species" Applied Microbiology, Dec. 1973, pp. 914-918. ****See Priority U.S. Appl. No. 13/481,787, filed May 26, 2012.
Bell et al. "Composition and functional analysis of the *Saccharomyces cerevisiae* trehalose synthase complex" 1998, J. Bioi. Chem., vol. 273, pp. 33311-33319 ****See Priority U.S. Appl. No. 13/481,787, filed May 26, 2012.
Elliott et al. "Synergy between trehalose and Hsp1 04 for thermotolerance in *Saccharomyces cerevisiae*" 1996, Genetics, vol. 144, pp. 923-933 ****See Priority U.S. Appl. No. 13/481,787, filed May 26, 2012.
"Guidance memorandum Mar. 4, 2014" accessed Mar. 27, 2014 from pp. 18. ****See Priority U.S. Appl. No. 13/481,787, filed May 26, 2012.
Leonard et al. "Bioactivity of selected essential oils and some components on Listeria monocytogenes biofilms" South African Journal of Botany, 2010, vol. 76, pp. 676-680 ****See Priority U.S. Appl. No. 13/481,787, filed May 26, 2012.
Wills et al. "Characterization and Regulation of the Trehalose Synthesis Pathway and Its Importance in the Pathogenicity of Cryptococcus neoformans" Infect. Immun. 2006, vol. 74(1 0), pp. 5877-5887. ****See Priority U.S. Appl. No. 13/481,787, filed May 26, 2012.
Ramage et al. "Our Current Understanding of Fungal" Biofilms, 2009, Critical Reviews in Microbiology, vol. 35(4): pp. 340-355. ****See Priority U.S. Appl. No. 13/481,787, filed May 26, 2012.
Biofilms: Survival Mechanisms of Clinically Relevant Microorganisms, Clinical Microbiology Reviews, Apr. 2002: 167-193 ****See Priority U.S. Appl. No. 13/481,787, filed May 26, 2012.
Review. Bacterial extracellular polysaccharides involved in biofilm formation, Molecules, 2009; 14:2535-2554 ****See Priority U.S. Appl. No. 13/481,787, filed May 26, 2012.
Review. Mechanisms of biofilm resistance to antimicrobial agents, Trends in Microbiology, Jan. 2001, 9(1 ): 34-39 ****See Priority U.S. Appl. No. 13/481,787, filed May 26, 2012.
Bacterial biofilms: a common cause of persistent infections, Science 1 999; 284: 1318-1322 ****See Priority U.S. Appl. No. 13/481,787, filed May 26, 2012.
Enzymatic removal and disinfection of bacterial biofilm, Appl. Environ. Microbial., 1997; 63: 3724-3728 ****See Priority U.S. Appl. No. 13/481,787, filed May 26, 2012.
Alginate lyase promotes diffusion of aminoglycosides through the extracellular polysaccharide of mucoid Pseudomonas aeruginosa, Antimicrob. Agents Chemother., 1998: 42: 974-977 ****See Priority U.S. Appl. No. 13/481,787, filed May 26, 2012.
New antibiotic agents and approaches to treat biofilm-associated infections, Expert Opin. Ther. Patents (201 0); 20(1 0): 1373-1387 ****See Priority U.S. Appl. No. 13/481,787, filed May 26, 2012.
A Potpourri of Probing and Treating Biofilms of the Oral Cavity, Microbe Magazine, Oct. 2009 ****See Priority U.S. Appl. No. 13/481,787, filed May 26, 2012.
The role of biofilm in wounds, a thesis submitted to the University of Wales, Cardiff, UK, May 2010, Chapter 5: Antimicrobial effect of honey on biofilm and quorum sensing: 190-234 ****See Priority U.S. Appl. No. 13/481,787, filed May 26, 2012.
Treatment of Biofilm Infections on Implants with Low-frequency Ultrasound and Antibiotics, Am J Infect Control. Mar. 2005; 33(2): 78-82 ****See Priority U.S. Appl. No. 13/481,787, filed May 26, 2012.
A comparison of two antimicrobial-impregnated central venous catheters, N Engl J Med, 1999; 340: 1-8 ****See Priority U.S. Appl. No. 13/481,787, filed May 26, 2012.
Reduced intravascular catheter infection by antibiotic bonding. A prospective, randomized, controlled trial, JAMA, 1991; 265:2364-2368 ****See Priority U.S. Appl. No. 13/481,787, filed May 26, 2012.
Efficacy of an attachable subcutaneous cuff for the prevention of intravascular catheter-related infection, JAMA, 1 989; 261:878-883 ****See Priority U.S. Appl. No. 13/481,787, filed May 26, 2012.
In vivo efficacy of silver-coated (Silzone) infection-resistant polyester fabric against a biofilm-producing bacteria, *Staphylococcus epidermidis*, J Heart Valve Dis 1998; 7: 524 **** See Priority U.S. Appl. No. 13/481,787, filed May 26, 2012.

(56) References Cited

OTHER PUBLICATIONS

Definitive cure of recurrent prosthetic endocarditis using silver-coated St. Jude medical heart valves: a preliminary case report, J Heart Valve Dis., 1998; 7: 531 ****See Priority U.S. Appl. No. 13/481,787, filed May 26, 2012.
Biofilms and Device-Associated Infections, Emerging Infectious Diseases Journal, Mar.-Apr. 2001; vol. 7, No. 2: 277-281 ****See Priority U.S. Appl. No. 13/481,787, filed May 26, 2012.
The effectiveness of acoustic energy induced by UroShield device in the prevention of bacteriuria and the reduction of 19 patients' complaints related to long-term indwelling urinary catheters, Poster presentation at 26th Annual Congress of the European Association of Urology (EAU); Vienna, Mar. 2011: No. 483 ****See Priority U.S. Appl. No. 13/481,787, filed May 26, 2012.
WHO Food Additives Series 46: Trehalose. International Programme on Chemical Safety, http:/fwww.inchem.org/documents/jecfa/jecmono/v46je05.htm ****See Priority U.S. Appl. No. 13/481,787, filed May 26, 2012.
"Microbe" is a screenprint of the webpage http://commtechlab.msu.edu/sites/dlc-me/zoo/ziwim.html acessed Sep. 10, 2016 ****See Priority U.S. Appl. No. 13/481,787, filed May 26, 2012.
Alan B.G. Lansdown "Silver in Health Care: Antimicrobial Effects and Safety in Use" Curr Probl Dermatol. Basel, Karger, 2006, vol. 33, pp. 17-34.
Sugimoto et al. "Molecular Cloning, Sequencing, and Expression of cDNA Encoding Serine Protease with Fibrinolytic Activity from Earthworm" Bioscience, Biotechnology, and Biochemistry: 2001; 65:7, 1575-1580.
Kadurugamuwa et al. "Direct Continuous Method for Monitoring Biofilm Infection in a Mouse Model" Infection and Immunity: Feb. 2003, p. 882-890.
Ammons et al. "In vitro susceptibility of established biofilms composed of a clinical wound isolate of Pseudomonas aeruginosa treated with lactoferrin and xylitol" International Journal of Antimicrobial Agents: 33 2009, 230-236.
Pineau et al. Comparison of the fixative properties of five disinfectant solutions Journal of Hospital Infection: 2008, 68, 171-177.
Schmidt et al. . Sustained Reduction of Microbial Burden on Common Hospital Surfaces through Introduction of Copper Journal of Clinical Microbiology: Jul. 2012, vol. 50 No. 7; p. 2217-2223.
Ben-Knaz et al. "Antibacterial activity of silver-killed bacteria: the "zombies" effect" Scientific Reports: Apr. 23, 2015. pp. 5.
Arne Dahlqvist "Method for assay of intestinal disaccharidases" Anal. Biochem. 7:18-25, 1964. Abstract Only.
Anonymous "Antimicrobial Resistance—Antimicrobial Copper touch surfaces are a new weapon in the fight against healthcare associated infections and the spread of antimicrobial resistance" http://www.antimicrobialcopper.org/uk/antimicrobial-resistance; retrieved from internet Jul. 5, 2017; pp. 6.
Y. Yoneyama "Purification and properties of detergent-solubilized pig kidney trehalase" Arch Biochem Biophys. May 15, 1987;255(1):168-75. Abstract Only.
Casey et al. "Role of copper in reducing hospital environment contamination" Journal of Hospital Infection: Jan. 2010 vol. 74, Issue 1, pp. 72-77. Abstract Only.
Salgado et al. "Copper surfaces reduce the rate of healthcare-acquired infections in the intensive care unit" Infect Control Hosp Epidemiol: May 2013;34(5):479-86. Abstract Only.
Alfa et al. "Cleaning efficacy of medical device washers in North American healthcare facilities" J Hosp Infect: Feb. 2010; 74(2):168-77. Abstract Only.
Ammons et al. Anti-biofilm efficacy of a lactoferrin/xylitol wound hydrogel used in combination with silver wound dressings Int Wound J.: Jun. 2011;8(3):268-73. Abstract Only.
Wg et al. "Water, water everywhere nor any a sterile drop to rinse your endoscope" J Hosp Infect: Aug. 2002; 51(4):256-61. Abstract Only.
Pace et al., "Biofilms, Infection, and Antimicrobial Therapy," CRC Press; Taylor & Francis Group, LLC; 2006; Chapter 16, p. 360.

TREHALOSE CHEMICAL STRUCTURE ($C_{12}H_{22}O_{11}$)

TREHALOSE BACKBONE

EXAMPLE RIBBON MODELS OF TREHALASE ENZYMES

NEUTRAL TREHALASE; SACHAROMYCES CEREVISIAE (STRAIN RM11-1a, BAKER'S YEAST)

ALPHA, ALPHA-TREHALASE TreB/Nth1; PENICILLIUM MARNEFFEI (STRAIN ATCC 18224/ CBS 334.59/QM 7333)

ALPHA,ALPHA-TREHALASE; HOMO SAPIENS

NEUTRAL TREHALASE: CANDIDA ALBICANS (YEAST)

BIOFILM PRODUCED BY P. AERUGINOSA PAO1

| BIOFILM FORMATION | BIOFILM MASS | | CELL VIABILITY | | BACTERIAL COUNT | |
|---|---|---|---|---|---|---|
| | 24 | 48 | 24 | 48 | 24 | 48 |
| TREHALASE 0.092UI | + | + | - | - | - | - |
| CEFTAZIDIME 0.25µg/ml + TREHALASE | + | + | - | - | - | - |
| TOBRAMYCIN 0.06µg/ml + TREHALASE | + | + | - | - | - | - |

| PREFORMED BIOFILM | BIOFILM MASS | | CELL VIABILITY | | BACTERIAL COUNT | |
|---|---|---|---|---|---|---|
| | 24 | 48 | 24 | 48 | 24 | 48 |
| TREHALASE 0.092UI | + | - | - | + | - | - |
| CEFTAZIDIME 0.25µg/ml + TREHALASE | + | - | - | + | - | - |
| TOBRAMYCIN 0.06µg/ml + TREHALASE | + | - | - | + | - | - |

LEGEND:
+ : INHIBITION OF BIOFILM (VS. CONTROL GROUP);
- : NO EFFECT OR INCREASE OF BIOFILM (VS. CONTROL GROUP)

FIG. 3

BIOFILM PRODUCED BY S. AUREUS ATCC25923

| BIOFILM FORMATION | BIOFILM MASS | | CELL VIABILITY | | BACTERIAL COUNT | |
|---|---|---|---|---|---|---|
| | 24 | 48 | 24 | 48 | 24 | 48 |
| TREHALASE 0.092UI | + | NT | + | NT | + | NT |
| CEFTAZIDIME 2μg/ml + TREHALASE | + | NT | + | NT | + | NT |
| GENTAMICIN 0.5μg/ml + TREHALASE | + | NT | + | NT | + | NT |

| PREFORMED BIOFILM | BIOFILM MASS | | CELL VIABILITY | | BACTERIAL COUNT | |
|---|---|---|---|---|---|---|
| | 24 | 48 | 24 | 48 | 24 | 48 |
| TREHALASE 0.092UI | + | + | + | + | + | + |
| CEFTAZIDIME 2μg/ml + TREHALASE | + | + | + | + | + | + |
| GENTAMICIN 0.5μg/ml + TREHALASE | + | + | + | + | + | + |

LEGEND:
+ : INHIBITION OF BIOFILM (VS. CONTROL GROUP);
- : NO EFFECT OR INCREASE OF BIOFILM (VS. CONTROL GROUP)
NT = NOT TESTED

FIG. 4

| 24 HOURS | BIOFILM PRODUCED BY S. AUREUS ATCC25923 | | | | | |
|---|---|---|---|---|---|---|
| | BIOFILM FORMATION | | | PRE-FORMED BIOFILM | | |
| TREATMENT | BIOFILM MASS (CRISTAL VIOLET) | BACTERIAL COUNT (cfu/ml) | CELL VIABILITY (RESAZURIN) | BIOFILM MASS (CRISTAL VIOLET) | BACTERIAL COUNT (cfu/ml) | CELL VIABILITY (RESAZURIN) |
| SIGMA SOLVENT 1 (CONTENT 50% GLYCEROL CONTAINING 1% TRITON™ X-100 AND 25 mM POTASSIUM PHOSPHATE, pH 6.5) | DECREASE 85% | INCREASE (0.5 log) | DECREASE 40% | DECREASE 60% | DECREASE (1.0 log) | NO EFFECT |
| TREHALASE 0.092 UI (SIGMA ALDRICH) | DECREASE 76% | DECREASE (1.2 log) | DECREASE 80% | DECREASE 34% | DECREASE (0.8 log) | NO EFFECT |
| SOLVENT 2 (CONTENT 25 mM POTASSIUM PHOSPHATE, pH 6.5) | NO EFFECT | INCREASE (0.5 log) | NO EFFECT | DECREASE 45% | NO EFFECT | NO EFFECT |
| TREHALASE 0.092 UI (DIALYZED IN AMICON® ULTRA-15 CENTRIFUGAL FILTER DEVICES) | DECREASE 72% | INCREASE (0.1 log) | NO EFFECT | DECREASE 36% | DECREASE (0.8 log) | NO EFFECT |

FIG. 5

| 24 HOURS | BIOFILM PRODUCED BY P. AERUGINOSA PAO1 ||||||
|---|---|---|---|---|---|---|
| | BIOFILM FORMATION ||| PRE-FORMED BIOFILM |||
| TREATMENT | BIOFILM MASS (CRISTAL VIOLET) | BACTERIAL COUNT (cfu/ml) | CELL VIABILITY (RESAZURIN) | BIOFILM MASS (CRISTAL VIOLET) | BACTERIAL COUNT (cfu/ml) | CELL VIABILITY (RESAZURIN) |
| SIGMA SOLVENT 1 (CONTENT 50% GLYCEROL CONTAINING 1% TRITON™ X-100 AND 25 mM POTASSIUM PHOSPHATE, pH 6.5) | INCREASE 58% | NO EFFECT | NO EFFECT | NO EFFECT | DECREASE (0.4 log) | NO EFFECT |
| TREHALASE 0.092 UI (SIGMA ALDRICH) | NO EFFECT | NO EFFECT | NO EFFECT | DECREASE 38% | DECREASE (0.6 log) | DECREASE 80% |
| SOLVENT 2 (CONTENT 25 mM POTASSIUM PHOSPHATE, pH 6.5) | INCREASE 23% | NO EFFECT | NO EFFECT | NO EFFECT | NO EFFECT | DECREASE 25% |
| TREHALASE 0.092 UI (DIALYZED IN AMICON® ULTRA-15 CENTRIFUGAL FILTER DEVICES) | INCREASE 32% | NO EFFECT | NO EFFECT | DECREASE 31% | DECREASE (0.2 log) | NO EFFECT |

FIG. 6

| ORGANISM | CIPROFLOXACIN + TREHALASE MIC (µg/mL) | CIPROFLOXACIN - TREHALASE MIC (µg/mL) | VANCOMYCIN + TREHALASE MIC (µg/mL) | VANCOMYCIN - TREHALASE MIC (µg/mL) | GENTAMICIN + TREHALASE MIC (µg/mL) | GENTAMICIN - TREHALASE MIC (µg/mL) |
|---|---|---|---|---|---|---|
| S. AUREUS ATCC25923 | 0.125 | 0.125 | 1 | 2 | 0.03 | 0.25 |
| S. AUREUS ATCC35556 | 0.03 | 0.125 | 0.5 | 1 | 0.015 | 0.5 |
| S. AUREUS OXFORD | 0.125 | 0.125 | 0.5 | 0.5 | 0.03 | 0.5 |

FIG. 7

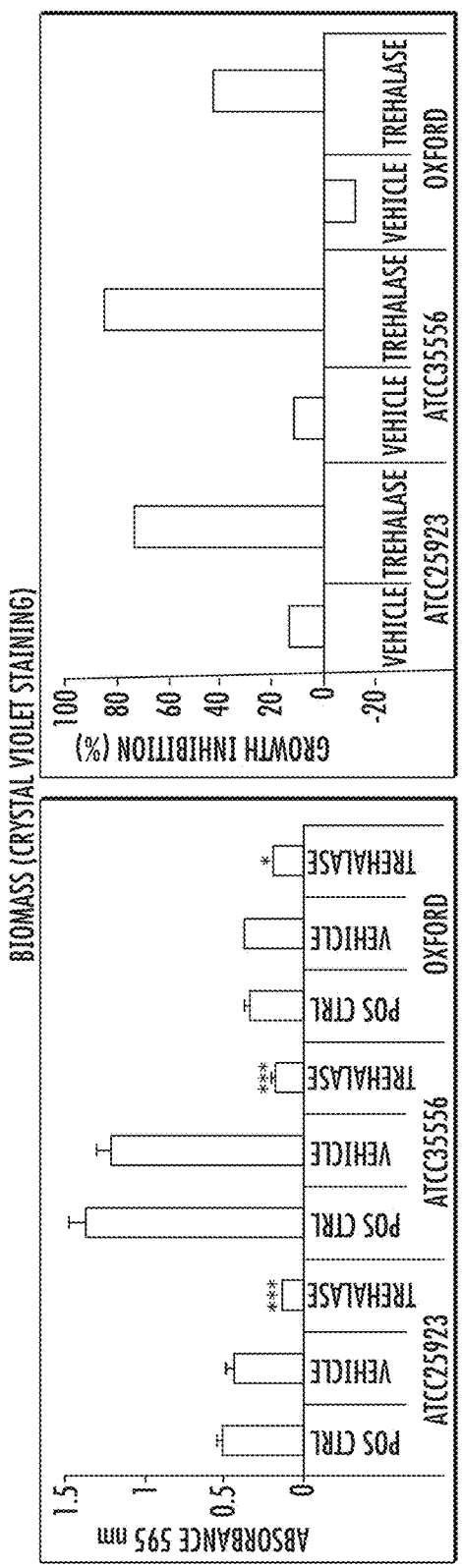
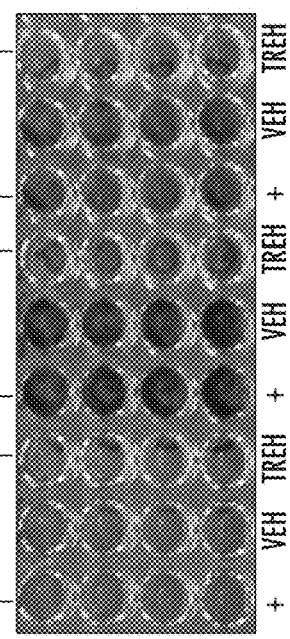
FIG. 9A
FIG. 9B
FIG. 9C

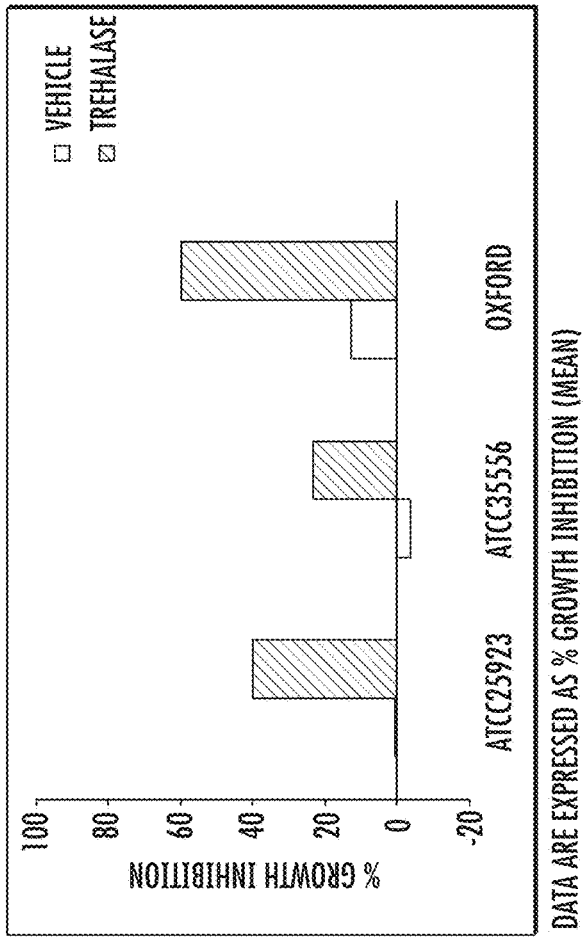
FIG. 10A
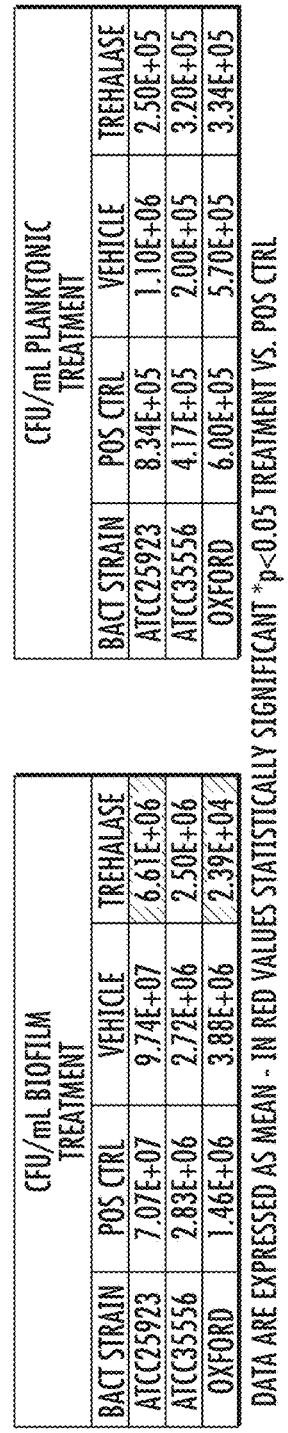
FIG. 10B
FIG. 10C

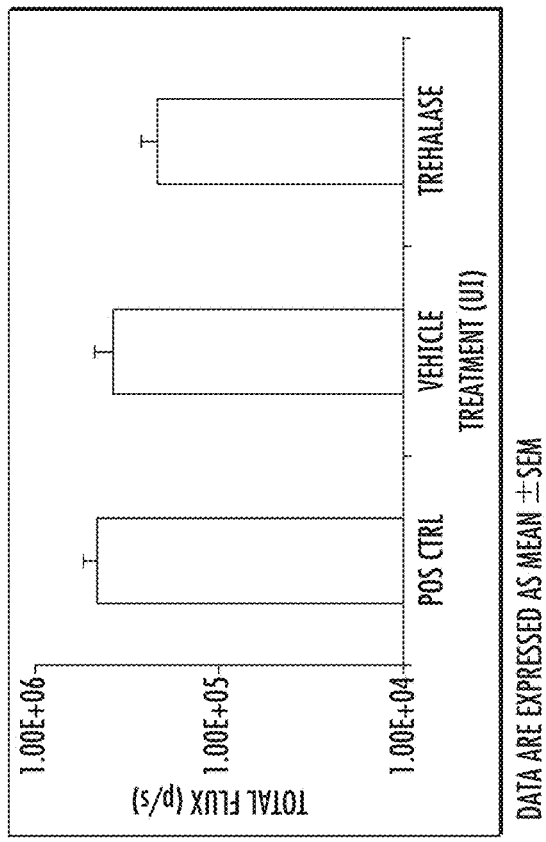

FIG. 11B

DATA ARE EXPRESSED AS MEAN ±SEM

| TREATMENT | PLANKTONIC LOG CFU/mL MEAN ±SEM | BIOFILM LOG CFU/mL MEAN ±SEM |
|---|---|---|
| POSITIVE CONTROL | 8.18 ±0.04 | 7.49 ±0.04 |
| VEHICLE | 7.78 ±0.16 | 7.47 ±0.10 |
| TREHALASE | 7.28 ±0.20* | 6.20 ±0.10* |

DATA ARE EXPRESSED AS MEAN ±SEM - ONE-FACTOR ANOVA FOLLOWED BY DUNNET'S POST HOC ANALYSIS. *p<0.05 POS CTRL VS. TREATMENT

FIG. 11C

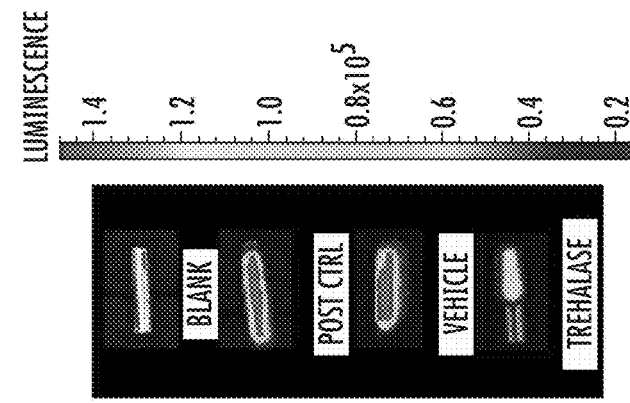

FIG. 11A

MONITORING LEVEL OF BIOLUMINESCENCE ACTIVITY ON CATHETER SEGMENTS. IMAGES WERE ACQUIRED WITH THE IVIS CAMERA AND ARE DISPLAYED AS PSEUDOCOLOR IMAGES. THE COLOR BAR INDICATES RELATIVE SIGNAL INTENSITY

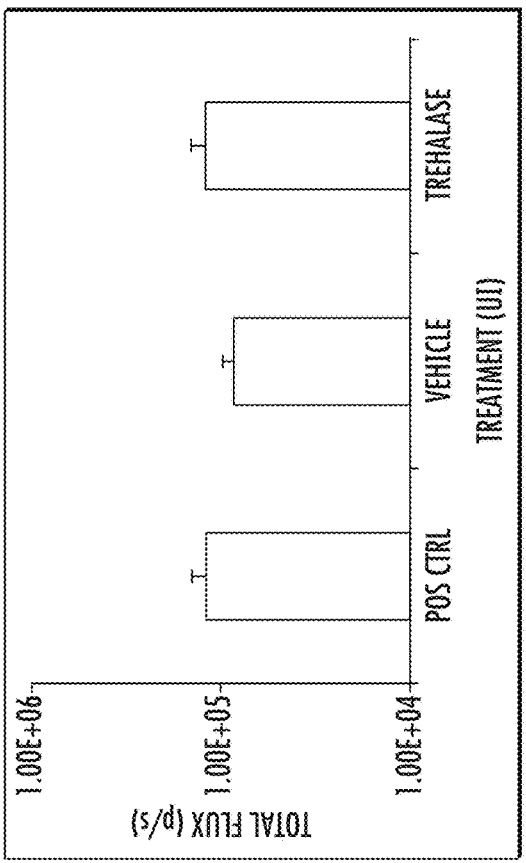
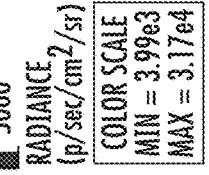
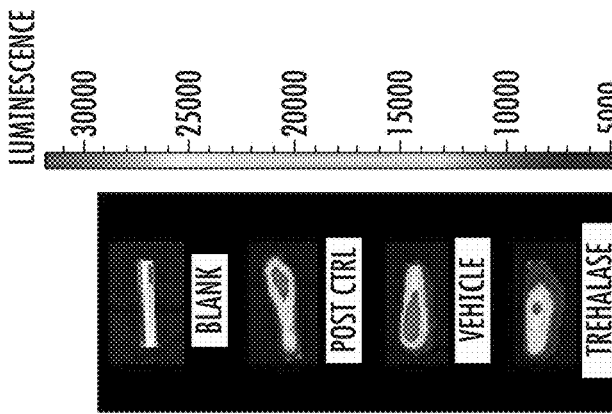
FIG. 12A
FIG. 12B
FIG. 12C

COMPOSITIONS AND METHODS TO PREVENT AND TREAT BIOFILMS

RELATED APPLICATIONS

This is continuation-in-part application of Ser. No. 13/481,787 filed May 26, 2012, which is based on provisional application Ser. No. 61/520,654 filed Jun. 13, 2011, the disclosures which are hereby incorporated by reference in their entirety.

FIELD OF THE INVENTION

The present disclosure is generally related to compositions and methods to prevent and treat biofilms.

DESCRIPTION OF RELATED ART

Over the last century, bacterial biofilms have been described as a ubiquitous form of microbial life in various ecosystems which can occur at solid-liquid, solid-air, liquid-liquid, and liquid-air interfaces. The general theory of biofilm predominance was defined and published in 1978 (Costerton J W, Geesey G G, and Cheng G K, "How bacteria stick," Sci. Am., 1978; 238: 86-95). The basic data for this theory initially came mostly from natural aquatic ecosystems showing that more than 99.9% of the bacteria grow in biofilms on a variety of surfaces, causing serious problems in industrial water systems as well as in various pipelines and vessels.

Later this fundamental theory of bacterial biofilm was accepted in the medical and dental areas. New and advanced methods for the direct examination of various biofilms showed that microorganisms that cause many medical device-related and other chronic infections in the human body actually grow in biofilms in or on these devices, as well as on mucosal linings of various organs and systems (oral cavity, respiratory tract, eyes, ears, GI tract, and urinary tract). As stated in this theory, "bacteria have certain basic survival strategies that they employ wherever they are" (Donlan R M and Costerton J W, "Biofilms: Survival Mechanisms of Clinically Relevant Microorganisms," Clinical Microbiology Reviews, April 2002: 167-193.)

The Nature and Structure of Biofilms

Over decades, direct physical and chemical studies of various biofilms (mostly grown in laboratory settings) show that they consist of single microbial cells and microcolonies, all embedded in a highly hydrated exopolymer matrix comprising biopolymers of microbial origin, such as polysaccharides (the major component), proteins, glycoproteins, nucleic acids, lipids, phospholipids, and humic substances; ramifying water channels bisect the whole structure, carrying bulk fluid into the biofilm by convective flow, providing transport of nutrients and waste products, and contributing to a pH gradient within the biofilm (Costerton J W and Irvin R T, "The Bacteria Glycocalyx in Nature and Disease," Ann. Rev. Microbiol., 1981; 35: 299-324); (de Beer D, Stoodley P, and Lewandowski Z, "Liquid flow in heterogeneous biofilms," Biotechnol. Bioeng, 1994; 44: 636-641); (Himmelsbach D S and Akin D E, "Near-Infrared Fourier-Transform Raman. Spectroscopy of Flax (Linum usitatissimum L.) Stems," J Agric Food Chem, 1998; 46: 991-998); (Maquelin K, Kirschner C, Choo-Smith L P, van den Braak N, Endtz H P, Naumann D, and Puppels G J, "Identification of medically relevant microorganisms by vibrational spectroscopy," J Microbiol Methods, 2002; 51: 255-271); (Neu T R and Marshall K C, "Bacterial Polymers: Physicochemical Aspects of Their Interactions at Interfaces," J Biomater Appl, 1990; 5: 107-133); (Neugebauer U, Schmid U, Baumann K, Ziebuhr W, Kozitskaya S, Deckert V, Schmitt M, Popp J, "Toward a Detailed Understanding of Bacterial Metabolism—Spectroscopic Characterization of *Staphylococcus* Epidermidis," ChemPhysChem, 2007; 8: 124-137); (Weldon M K, Zhelyaskov V R, Morris M D, "Surface-enhanced Raman spectroscopy of lipids on silver microprobes," Appl Spectrosc, 1998; 52: 265-269). Depending on the biofilm type and the microorganisms involved, microcolonies of microbial cells make up approximately 10%-15% of the biofilm by volume, and the biofilm matrix comprises approximately 85%-90%. Water, the major component of the biofilm matrix, can make up to 95%-98% of the matrix volume, and the particulate fraction of the matrix can comprise the rest 2%-5% correspondingly. Extracellular polysaccharides and proteins have been considered to be the key components of the biofilm matrix and have been most extensively studied over decades (Sutherland I W, "The biofilm matrix—an immobilized but dynamic microbial environment," Trends Microbiol, 2001; 9: 222-227); (Stewart P S and Costerton J W, "Antibiotic resistance of bacteria in biofilms," Lancet, 2001; 358: 135-138); (Staudt C, Horn H, Hempel D C, Neu T R, "Volumetric measurements of bacteria and EPS-glycoconjugates in biofilms," Biotechnol Bioeng, 2004; 88: 585-592); (Zhang X Q, Bishop P L, and Kupferle M J, "Measurement of polysaccharides and proteins in biofilm extracellular polymers," Water Sci Technol, 1998; 37: 345-348).

Polysaccharides, postulated to be the key component of the biofilm matrix, provide diverse structural variations of the glycocalux formed by saprophytic and pathogenic microorganisms in a variety of environments (Barbara Vu, et al., "Review. Bacterial extracellular polysaccharides involved in biofilm formation," Molecules, 2009; 14: 2535-2554; doi: 3390/molecules 14072535). The types of polysaccharides in microbial biofilms are of enormous range and depend on the genetic profile of microorganisms involved and the physicochemical properties of local environment (Sutherland I W, "The biofilm matrix—an immobilized but dynamic microbial environment," Trends Microbiol., 2001; 9: 222-227). Many polysaccharides are constitutively produced by various bacteria as structural elements of the bacterial cell wall and virulence factors; they can stay attached to the bacterial cell wall surface, forming a complex network surrounding the cell with electrostatic and hydrogen bonds involved, or they can be released into media as exopolysaccharides (EPS) (Mayer C, Moritz R., Kirschner C., Borchar W, Maibaum R, Wingender J, and Flemming H C, "The role of intermolecular interactions: studies on model systems for bacterial biofilms," Int J Biol Macromol, 1999; 26: 3-16). Polysaccharides, as well as mono- and disaccharides, can be taken by bacteria from the environment and metabolized as a carbon source, and their metabolism is genetically regulated via balanced production of enzymes for both synthesis and degradation pathways (Sutherland I W, "Polysaccharases for microbial polysaccharides," Carbohydr Polym, 1999; 38: 319-328). Depending on their structure, EPS can bind various amount of water, and some of them (such as cellulose, mutan or curdlan) can even exclude most water from their tertiary structure. Over the years, the gel-like viscosity of the biofilm matrix was attributed mainly to the physical and chemical properties of the polysaccharides involved (Christensen B E, "The role of extracellular polysaccharides in biofilms," J Biotechnol, 1989; 10: 181-202); (Stoodley P, et al., "Oscillation characteristics of biofilm streamers in turbulent flowing water as related to drag and pressure drop," Biotechnol Bioeng, 1998; 57: 536-544). Exopolysaccharides can be neutral homopolymers (such as cellulose, dextrans, levans), but the majority are polyanionic (for example, alginates, gellan, xanthan produced by Gram-negative bacteria) with attraction of divalent cations (Ca, Mg) to increase binding force, and a few are polycationic, such as those produced by some Gram-positive bacteria (Sutherland I W, "Biotechnology of Exopolysaccharides," Cambridge: Cambridge University Press, 1990); (Mack D, Fische W, Krokotsc A, Leopold K, Hartmann R, Egge H, and Laufs R, "The intercellular adhesin involved in biofilm accumulation of Staphylococcus epidermidis is a linear β-1, 6-linked glucosaminoglycan: purification and structural analysis," J Bacteriol, 1996; 178: 175-183).

Because only small amounts of the biofilm-derived EPS are normally available for direct studies, the researchers usually use data derived from planktonic cell cultures and extrapolate them to biofilms. There is no conclusive evidence to support the idea of existence of the biofilm-specific polysaccharides, and to date, all studied polysaccharides present in various biofilms resemble closely the corresponding polymers synthesized by planktonic cells. It has been proposed that the increased amount of polysaccharides in biofilm (one or more, specific for a given bacteria in any given biofilm) can be part of a stress response in biofilm-grown microorganisms, and bacteria form exopolysaccharides as a by-product to release reducing equivalents accumulated in non-optimal growth conditions (Creti R, Koch S, Fabretti F, Baldassarri L, and Huebneri J, "Enterococcal colonization of the gastro-intestinal tract: role of biofilm and environmental oligosaccharides," BMC Microbiology, 2006; 6: 60 doi: 10.11.86/1471-2180-6-60); (Rinker K D, Kelly R M, "Effect of carbon and nitrogen sources on growth dynamics and exopolysaccharide production for the hyperthermophilic archaeon Thermococcus litoralis and bacterium Thermotoga maritime," Biotechnol Bioeng, 2000; 69: 537-547); (Sutherland I W, "Biofilm exopolysaccharides: a strong and sticky framework," Microbiology, 2001; 147: 3-9).

Other extracellular products (specific substances or by-products of bacterial metabolism), as well as detritus, can be either released into the biofilm from aging and lysed cells or trapped within the biofilm matrix, and "cemented" there by mixture of exopolysaccharides (Christensen B E, "The role of extracellular polysaccharides in biofilms," J. Biotechnol., 1989; 10: 181-201). These extracellular products include small sugars (mono-, disaccharides), polyols, proteins, glycoproteins, enzymes, lipids, glycolipids, phospholipids, nucleic acids, and DNA (Boyd A and Chakrabarty A M, "Role of alginate lyase in cell detachment of Pseudomonas aeruginosa," Appl Environ Microbiol, 1994; 60: 2355-2359); (Harz M, Røsch P, Peschke K D, Ronneberger O, Burkhardt H, and Popp J, "Micro-Raman spectroscopic identification of bacterial cells of the genus Staphylococcus and dependence on their cultivation conditions," Analyst, 2005; 130: 1543-1550); (Nottingher I, Verrier S, Haque S, Polak J M, Hench L L, "Spectroscopic study of human lung epithelial cells (A549) in culture: living cells versus dead cells," Biopolymers, 2003; 72: 230-240); (Sutherland I W, "A natural terrestrial biofilm," J Ind Microbiol, 1996; 17: 281-283); (Webb J S et al, "Cell death in Pseudomonas aeruginosa biofilm development," J. Bacteriol., 2003; 185: 4585-4592); (Weldon M K, Zhelyaskov V R, Morris M D, "Surface-enhanced Raman spectroscopy of lipids on silver microprobes," Appl Spectrosc, 1998; 52: 265-269); (Yarwood J M, et al., "Quorum sensing in Staphylococcus aureus biofilms," J. Bacteriol., 2004; 186: 1838-1850). It has been suggested that extracellular DNA, released from the lysed cells, plays an important role in supporting the biofilm structure and provides opportunities for microorganisms to exchange the genetic material for possible development of the biofilm-specific phenotypes (Costerton J W, Veeh R, Shirtliff M, Pasmore M, Post C, and Ehrich G D, "The application of biofilm science to the study and control of chronic bacterial infections," J. Clin. Invest., 2003; 112: 1466-1477); (Gilbert P, Maira-Litran T, McBain A J, Rickard A H, and Whyte F W, "The physiology and collective recalcitrance of microbial biofilm communities," Adv. Microb. Physiol., 2002; 46: 202-256); (Osterreicher-Ravid D, Ron E Z, & Rosenberg E, "Horizontal transfer of an exopolymer complex from one bacterial species to another," Environ Microbiol, 2000; 2: 366-372); (Stoodley P, Sauer K, Davies D G, and Costerton J W, "Biofilms as complex differentiated communities," Annu. Rev. Microbiol., 2002; 56: 187-209); (Whitchurch C B, et al., "Extracellular DNA required for bacterial biofilm formation," Science, 2002; 295: 1487).

It has been proposed that in the dynamic environment of biofilm, microorganisms use special chemical signaling molecules to communicate (the process called quorum-sensing—QS), and the presence of an adequate number of neighboring cells with coordinated chemical signaling between them allow bacteria to properly respond to changes in environmental conditions, including insult from antimicrobials, and benefit from living in the biofilm community. It was assumed that QS can regulate extracellular polysaccharide production, based on the major alterations in the extracellular matrix of laboratory-grown Pseudomonas aeruginosa biofilm when the mutant strain was unable to produce the N-(3-oxododecanoyl)-L-homoserine lactone signal specific for QS (Davies D, Parsek M, Pearson J, et al., "The involvement of cell-to-cell signals in the development of a bacterial biofilm," Science, 1998; 280: 295-298); (Singh P, Schaeffer A, Parsek M, et al., "Quorum sensing signals indicate that cystic fibrosis lungs are infected with bacterial biofilms," Nature, 2000; 407: 762-764). But to date, the quorum-sensing-regulated genes involved in Pseudomonas aeruginosa biofilm matrix production have not been identified, and the pel and/or psl genes (regulating production of other polysaccharides PEL and PSL) have not been revealed as quorum-sensing-regulated genes as well (Branda S S, Vik A, Friedman L, and Kolter R, "Biofilms: the matrix revisited," Trends in Microbiology, 2005; 13(1): 20-26); (Whiteley M, et al., "Identification of genes controlled by quorum sensing in Pseudomonas aeruginosa," Proc. Natl. Acad. Sci. U.S.A., 1999; 96: 13904-13909). Also, the role of quorum sensing in resistance of biofilm to antimicrobials is not clear yet; for example, the laboratory mutants defective in quorum sensing, are unaffected in their resistance to detergents and antibiotics (Brooun A, et al., "A dose-response study of antibiotic resistance in Pseudomonas aeruginosa biofilms," Antimicrob. Agents Chemother, 2000; 44: 640-646).

According to a classical model, any biofilm can be described as: a non-homogenous multi-layer structure with dynamic environment; growing in a 3-dimensional mode, with constant addition of the new layers and detachment of the parts of the biofilm; with spatial and temporal heterogeneity within the biofilm and variations in bacterial growth rate; with different metabolic and genetic activities of the microorganisms resulting in increased resistance to antimicrobials (including antibiotics) and host defense mechanisms (Charaklis W G, Marshall K C, "Biofilm as a basis for interdisciplinary approach," pp. 3-15, In: Biofilms, 1990, John Wiley and Sons, Charaklis W G. and Marshall K C. (ed.), New York, N.Y.); (Fux C A, et al., "Review. Survival strategies of infectious biofilms", Trends in Microbiology, January 2005; Vol. 13, No 1: 34-40). The heterogeneity within the biofilm has been confirmed for protein synthesis and respiratory activity, but the DNA content remained relatively constant throughout biofilm (Wentland E J, et al., "Spatial variations in growth rate within *Klebsiella pneumoniae* colonies and biofilm," Biotechnol. Prog., 1996; 12: 316-321); (Xu K D, et al., "Biofilm resistance to antimicrobial agents," Microbiology, 2000; 146: 547-549). An oxygen tension gradient exists within biofilm with the superficial areas being more metabolically active than the deeper areas where bacteria adapt to decreased oxygen availability (De Beer D, Stoodley P, Roe F, et al., "Effects of biofilm structure on oxygen distribution and mass transport," Biotechnology Bioengineering, 1994; 43: 1131-1138). The outer layers of biofilm are more permeable to antimicrobials due to slow build-up of polysaccharides and other constituents (proteins, lipids, etc.), and the inner (deeper) layers are more dense, compressed, and less permeable. Bacteria in the outer layers of biofilm, exposed to the bulk medium, grow faster and can be less resistant to antimicrobials. Conversely, the bacteria in the inner or deeper layers, located closer to the attached surface, grow slower, adapting to decreased oxygen and nutrients availability, and in time, can become more resistant to antimicrobials with possible consequent emergence of biofilm-specific antibiotic-resistant phenotype (Brown M R, et al., "Resistance of bacterial biofilms to antibiotics: a growth-rate related effect?," J. Antimicrob. Chemother., 1998; 22: 777-780).

It has been proposed that "any given cell within the biofilm will experience a slightly different environment compared with other cells within the same biofilm, and thus be growing at a different rate" (Mah T C, and O'Toole G A, "Review. Mechanisms of biofilm resistance to antimicrobial agents," Trends in Microbiology, January 2001, 9(1): 34-39). With continuous bacterial growth, increased cell density triggers the general stress response in microbial cells, as confirmed by increased production of osmoprotectant trehalose and degrading enzyme catalase, with higher concentration of trehalose in proximity to the pathogenic cell colonies (Liu X, et al., "Global adaptations resulting from high population densities in *Escherichia coli* cultures," J. Bacteriol., 2000; 182: 4158-4164). These events result in physiological changes in biofilm, including reduced flow of solutes (nutrients) into biofilm and diminished growth rate of bacterial microcolonies for genotype survival (Brown M R, and Barker J, "Unexplored reservoirs of pathogenic bacteria: protozoa and biofilms," Trends Microbiol., 1999; 7: 46-50); (Mah T C., and O'Toole G A, "Review: Mechanisms of biofilm resistance to antimicrobial agents", Trends in Microbiology, January 2001; 9(1): 34-39).

About two decades ago, the existence of biofilm-specific phenotypes of bacteria was an emerging idea. Such biofilm-specific phenotypes, thought to be induced in a subpopulation of microorganisms upon attachment to a surface, were proposed to express specific biofilm-related genes compared with their planktonic counterparts (Kuchma S L, and O'Toole G A, "Surface-induced and biofilm-induced changes in gene expression," Curr. Opin. Biotechnol., 2000; 11: 429-433). Multiple research data, based mostly upon the genetic studies of the laboratory-constructed and laboratory-grown mutant strains, provided supportive evidence that the biofilm-grown cells differ from their planktonic counterparts in specific properties, including nutrients utilization, growth rate, stress response, and increased resistance to antimicrobial agents and the host defenses.

Biofilm Resistance to Antimicrobial Agents

The mechanism of resistance to antimicrobial agents (including antibiotics) in biofilm-related microorganisms is different from plasmid, transposons, and mutations that confer innate resistance in individual bacterial cells (Stewart P S and Costerton J W, "Review. Antibiotic resistance of bacteria in biofilms," Lancet, 2001; 358: 135-138); (Costerton J W, Stewart P S, and Greenberg E, "Bacterial biofilms: a common cause of persistent infections," Science, 1999; 284: 1318-1322); (Costerton J W and Stewart P S, "Biofilms and device-related infections," In: Nataro J P, Blaser M J, Cunningham-Rundles S., (eds.), Persistent bacterial infections. Washington, D.C.: ASM Press, 2000; 432-439).

Multiple research studies provided basis for various mechanisms of biofilm resistance to antimicrobials, including:

physical and/or chemical diffusion barriers to penetration of antimicrobials and host defense cells into the exopolymer matrix of biofilm activation of a general stress response of the microorganisms slow growth of the microorganisms possible emergence of a biofilm-specific bacterial phenotype These mechanisms can be applied to any type of biofilm, varying with the bacteria present and the type of antimicrobials being used (Geddes A, "Infection in the twenty-first century: Predictions and postulates," J Antimicrob Chemother, 2000; 46: 873-878); (Stewart P S, "Theoretical aspects of antibiotic diffusion into microbial biofilms," Antimicrob. Agents Chemother., 1996; 40: 2517-2522); (Stewart P S, "Mechanisms of antibiotic resistance in bacterial biofilms," Int J Med Microbiol, 2002; 292: 107-113).

Most of the biofilm-resistance mechanisms are provided by the biofilm exopolymer matrix as the initial physical and/or chemical barrier that can prevent, inhibit or delay penetration of antimicrobials and host defense cells into the biofilm. The diffusion of antimicrobials through the biofilm can be inhibited by various means: for example, the common disinfectant chlorine is consumed by chemical reaction within the matrix of a mixed *Klebsiella pneumoniae* and *Pseudomonas aeruginosa* biofilm (de Beer D, et al., "Direct measurement of chlorine penetration into biofilms during disinfection," Appl. Environ. Microbiol., 1994; 60: 4339-4344); antibiotic ciprofloxacin binds to the biofilm components (Suci P A, et al., "Investigation of ciprofloxacin penetration into *Pseudomonas aeruginosa* biofilms," Antimicrob Agents Chemother, 1994; 38: 2125-2133); *Pseudomonas aeruginosa* biofilm prevents diffusion of piperacillin (Hoyle B, et al., "*Pseudomonas aeruginosa* biofilm as a diffusion barrier to piperacillin," Antimicrob. Agents Chemother., 1992: 36: 2054-2056); positively charged aminoglycosides bind to negatively charged matrix polymers, such as β 1,4-glucosaminoglycan in *Staphylococcus epidermidis* biofilm and alginate in *Pseudomonas aeruginosa* biofilm (Lewis K, "Riddle of biofilm resistance," Antimicrob Agents Chemother., 2001; 45: 999-1007); (Walters M C, et al., "Contributions of antibiotic penetration, oxygen limitation, and low metabolic activity to tolerance of *Pseudomonas aeruginosa* biofilms to ciprofloxacin and tobramycin," Antimicrob. Agents Chemother., 2003; 47: 317-323); (Gordon C A, Hodges N A, Marriott C, "Antibiotic interaction and diffusion through alginate exopolysaccharide of Cystic fibrosis—derived *Pseudomonas aeruginosa*," J. Antimicrob. Chemother., 1988; 22: 667-674);

(Nichols W W, et al., "Inhibition of tobramycin diffusion by binding to alginate," Antimicrob. Agents Chemother., 1988; 32: 518-523); the additional matrix component colanic acid, produced by mucoid phenotype of *E. coli*, supports biofilm maturation and provides a thicker biofilm (Danese P N, et al., "Exopolysaccharide production is required for development of *Escherichia coli* K-12 biofilm architecture," J. Bacteriol., 2000; 182: 3593-3596); penetration of antifungal agent nystatin into the mycelium of *Aspergillus fumigatus* submerged in medium and covered by thin layer of exopolymer matrix is higher than into the aerial-grown colony covered by thick layer of extracellular matrix (Beauvais A, et al., "An extracellular matrix glues together the aerial-grown hyphae of *Aspergillus fumigatus*," Cellular Microbiology, 2007; 9 (6): 1588-1600); secreted IgG antibodies fail to penetrate biofilm because of matrix binding (de Beer D, et al., "Measurement of local diffusion coefficients in biofilms by micro-injection and confocal microscopy," Biotechnol. Bioeng., 1997; 53: 151-158); alginate produced by mucoid phenotype of *Pseudomonas aeruginosa* protects bacteria from phagocytosis by host leukocytes and INF-γ activated macrophages (Bayer A S, et al., "Functional role of mucoid exopolysaccharide (alginate) in antibiotic-induced and polymorphonuclear leukocyte-mediated killing of *Pseudomonas aeruginosa*," Infect. Immun., 1991; 59: 302-308); (Leid J G, Willson C J, Shirtliff M E, Hassett D J, Parsek M R, and Jeffers A K, "The exopolysaccharide alginate protects *Pseudomonas aeruginosa* biofilm bacteria from IFN-gamma-mediated macrophage killing." J Immunol, 2005; 175: 7512-7518).

Antimicrobials diffusion can also be inhibited or delayed by specific active substances produced by bacteria themselves: for example, enzyme catalase produced by *Pseudomonas aeruginosa* spp. degrades hydrogen peroxide on diffusion into thick biofilm (Stewart P S, et al., "Effect of catalase on hydrogen peroxide penetration into *Pseudomonas aeruginosa* biofilms," Appl. Environ. Microbiol., 2000; 66: 836-838); ampicillin is unable to penetrate biofilm of *Klebsiella pneumoniae* due to ampicillin-degrading enzyme Beta-lactamase (Anderi J N, et al., "Role of antibiotic penetration limitation in *Klebsiella pneumoniae* biofilm resistance to ampicillin and ciprofloxacin," Antimicrob. Agents Chemother., 2000; 44: 1818-1824); (Bagge N, Hentzer M, Andersen J B, Ciofu O, Givskov M, and Høiby N, "Dynamics and spatial distribution of beta-lactamase expression in *Pseudomonas aeruginosa* biofilms," Antimicrob Agents Chemother, 2004; 48: 1168-1174); extracellular slime derived from coagulase-negative *Staphylococci* reduces the effect of glycopeptide antibiotics (Konig C, et al., "Factors compromising antibiotic activity against biofilms of *Staphylococcus epidermidis*," Eur. J. Clin. Microbiol. Infect. Dis., 2001; 20: 20-26); (Souli M and Giamarellou H., "Effects of slime produced by clinical isolates of coagulase-negative *staphylococci* on activities of various antimicrobial agents," Antimicrob. Agents Chemother., 1998; 42: 939-941); a PMN toxin, rhamnolipid B, produced by *Pseudomonas aeruginosa* is known to kill neutrophils (Jensen P Ø, Bjarnsholt T, Phipps R, Rasmussen T B, Calum H, Christoffersen L, et al., "Rapid necrotic killing of polymorphonuclear leukocytes is caused by quorum-sensing-controlled production of rhamnolipid by *Pseudomonas aeruginosa*," Microbiology, 2007; 153: 1329-1338).

Delayed penetration of antimicrobials into the biofilm can provide enough time for bacteria to induce the expression of various genes regulating the stress response and mediating resistance to antimicrobials (Jefferson K K, Goldmann D A, and Pier G B, "Use of confocal microscopy to analyze the rate of vancomycin penetration through *Staphylococcus aureus* biofilms," Antimicrob Agents Chemother, 2005; 49: 2467-2473); (Anwar H, Strap J L, and Costerton J W, "Establishment of aging biofilms: a possible mechanism of bacterial resistance to antimicrobial therapy," Antimicrob Agents Chemother, 1992; 36: 1347-1351). The central regulator of a general stress response is the alternate sigma-factor RpoS induced by high cell density, and the presence of activated gene rpoS' mRNA was detected by RT-PCR in sputum from Cystic Fibrosis patients with chronic *Pseudomonas aeruginosa* biofilm infections (Foley I, et al., "General stress response master regulator rpoS is expressed in human infection: a possible role in chronicity," J. Antimicrob. Chemother., 1999; 43: 164-165). Also, it has been shown that an additional sigma-factor Alg acted in concert with RpoS to control general stress response in laboratory grown *Pseudomonas aeruginosa* during biofilm formation and maturation, and several other genes were upregulated as well, including algC (controlling phosphomannomutase, involved in exopolysaccharide alginate synthesis), algD, algU, and genes controlling polyphosphokinase synthesis (Davis D G and Geesey G G, "Regulation of the alginate biosynthesis gene algC in *Pseudomonas aeruginosa* during biofilm development in continuous culture," Appl. Environ. Microbiol., 1995; 61: 860-867). It has been demonstrated that as many as 45 genes differed in expression between sessile cells and their planktonic counterparts during the biofilm development in laboratory settings.

Biofilm-Based Medical Conditions and Diseases

Comprehensive review of the biofilm-based human infections as well as the biofilms on medical devices was published by Rodney M. Donlan and J. William Costerton (Donlan R M and Costerton J W, "Review. Biofilms: Survival mechanisms of clinically relevant microorganisms," Clinical Microbiology Reviews, April 2002; 167-193). Microbial biofilms are important factors in the pathogenesis of various human chronic infections, including native valve endocarditis (NVE), line sepsis, chronic otitis media, chronic sinusitis and rhinosinusitis, chronic bronchitis, cystic fibrosis *pseudomonas* pneumonia, chronic bacterial prostatitis, chronic urinary tract infections (UTIs), periodontal disease, chronic wound infections, osteomyelitis (Costerton J W, Stewart P, Greenberg E, "Bacterial biofilms: a common cause of persistent infections," Science, 1999; 284: 1318-1322); (Hall-Stoodley L and Stoodley P, "Evolving concepts in biofilm infections," Cellular Microbiology, 2009; 11 (7): 1034-1043). Microbial biofilms are detected on various medical devices (prosthetic heart valves, central venous catheters, urinary catheters, contact lenses, tympanostomy tubes, intrauterine devices), as well as on medical equipment (endoscopes, dialysis systems, nebulizers, dental unit water lines), and on a variety of surfaces in hospitals and other medical settings (Costeron J W and Stewart P S, "Biofilms and device-related infections," In: Nataro J. P., Blaser M. J., Cunningham-Rundles S., eds. Persistent bacterial infections. Washington, D.C.: ASM Press, 2000; 432-439); (Bryers J D, "Medical Biofilms," Biotechnology and Bioengineering, 2008; 100 (1) May 1). Due to their specific features, chronic biofilm-based infections require different interventional approaches for effective treatment (Stewart P S and Costerton J W., "Review. Antibiotic resistance of bacteria in biofilms," Lancet, 2001; 358: 135-138); (Donlan R M and Costerton J W, "Review. Biofilms: Survival mechanisms of clinically relevant microorganisms," Clinical Microbiology Reviews, April 2002; 167-193); (Costerton J W, Stewart P S, and Greenberg E P, "Bacterial biofilms: a common cause of persistent infections," Science, 1999; 284: 1318-1322);

(Costerton J W and Stewart P S, "Biofilms and device-related infections," In: Nataro J P, Blaser M J, Cunningham-Rundles S, eds. Persistent bacterial infections. Washington, D.C.: ASM Press, 2000; 432-439); (Wolcott R D, M.D. and Ehrlich G D, Ph.D., "Biofilms and chronic infections," JAMA, 2008, Vol. 299, No 22); (Costerton J W, Irvin R T, "The Bacteria Glycocalyx in Nature and Disease," Ann. Rev. Microbiol., 1981; 35: 299-324); (Costerton J W, et al., "The application of biofilm science to the study and control of chronic bacterial infections," J. Clin. Invest., 2003; 112: 1466-1477).

Native Valve Endocarditis

The development of Native Valve Endocarditis (NVE) results from the interaction between the endothelium of the heart (generally, of the mitral, aortic, tricuspid, and pulmonic valves) and microorganisms circulating in the bloodstream (Livornese L L and Korzeniowski O M, "Pathogenesis of infective endocarditis," pp. 19-35. In: Infective endocarditis, Kaye D. (ed.), 2-nd ed., 1992; Raven Press, New York, N.Y.). Microorganisms usually do not adhere to intact endothelium. There should be contributing factors that promote adherence, such as: damaged endothelium (as in vasculitis), formation of initial thrombotic lesions of heart valves (as in nonbacterial thrombotic endocarditis—NBTE), accumulation of fibronectin secreted by endothelial cells, platelets and fibroblasts in response to vascular injury, which can simultaneously bind to fibrin, collagen, human cells, and bacteria, specific fibronectin receptors in some bacteria (*Streptococcus sanguis, Staphylococcus aureus*), high-molecular weight dextrans produced by various *Streptococci* that promote adherence to the surface of the thrombus in NBTE (Lowrance J H, Baddour L M, and Simpson W A, "The role of fibronectin binding on the rate model of experimental endocarditis caused by *Streptococcus sanguis*," J. Clin. Investig. 86: 7-13); (Roberts R B, "Streptococcal endocarditis: the viridins and beta hemolytic *streptococci*," pp. 191-208. In: Infective endocarditis, Kaye D. (ed.), 2-nd ed., 1992; Raven Press, New York, N.Y.). The most metabolically active colonies were detected on the surface of the thrombus, forming initial biofilm there (Durack D T and Beeson P B, "Experimental bacterial endocarditis II. Survival of bacteria in endocardial vegetations," Br. J. Pathol., 1972, 53: 50-53). Clinical research of 2345 cases of NVE demonstrated a variety of microorganisms involved: *Streptococci* (including *Streptococcus viridans, Streptococcus bovis*), *Enterococci, Pneumococci* ~in 56% of cases; *Staphylococci* ~in 25% of cases (~19%—Coagulase positive and ~6%—Coagulase negative); Gram-negative bacteria ~in 11% of cases, and Fungi (*Candida* and *Aspergillus* spp.)~in 10% of cases; all these microorganisms gained access to the bloodstream primarily via the oropharynx, gastrointestinal tract, and genitourinary tract (Tunkel A R and Mandell G I, "Infecting microorganisms," pp. 85-97. In: Infective endocarditis, Kaye D. (ed.), 2-nd ed., 1992; Raven Press, New York, N.Y.).

Biofilm-Based Chronic Injections in the Respiratory Tract

In the upper respiratory tract, bacterial biofilms have been demonstrated in chronic tonsillitis, chronic adenoiditis, chronic sinusitis and chronic rhinosinusitis (CRS), chronic otitis media (OM), and cholesteatoma. In clinical specimens from patients with chronic and recurrent tonsillitis, both attached and aggregated biofilm-associated bacteria were detected in mucosal epithelium of tonsils removed for chronic tonsillitis (in 73% of cases) and in 75% of cases of tonsils removed due to hypertrophy alone (Chole R A and Faddis B T, "Anatomical evidence of microbial biofilms in tonsillar tissues: a possible mechanism to explain chronicity," Arch Otolaryngol Head Neck Surg, 2003; 129: 634-636). Microbial biofilms associated with epithelial lining with presence of a carbohydrate matrix in situ were demonstrated in clinical specimens of human adenoids removed for chronic adenoiditis (Kania R E, Lamers G E, Vonk M J, Dorpmans E, Struik J, Tran Ba Huy P, et al., "Characterization of mucosal biofilms on human adenoid tissues," Laryngoscope, 2008; 118: 128-134); (Nistico L, Gieseke A, Stoodley P, Hall-Stoodley L, Kerschner J E, and Ehrlich G D, "Fluorescence 'in situ' hybridization for the detection of biofilm in the middle ear and upper respiratory tract mucosa," Methods Mol Biol, 2009; 493: 191-213).

Chronic Rhinosinusitis

In Chronic Rhinosinusitis (CRS), mucosal changes with different degrees of denudation in epithelial cells result in a surface favorable for bacterial colonization and biofilm development (Biedlingmaier J, Trifillis A, "Comparison of CT scan and electron microscopic findings on endoscopically harvested middle turbinates," Otolaryngol Head Neck Surg, 1998; 118: 165-173). Biofilm formation, mainly with *Pseudomonas aeruginosa* infection, was confirmed in patients who had surgery and continued to have symptoms despite medical treatment (Cryer J, Schipor I, Perloff J R, Palmer J N, "Evidence of bacterial biofilms in human chronic sinusitis," ORL J Otolaryngol Relat Spec, 2004; 66: 155-158). In patients with CRS having surgery, mucosal biopsies demonstrated different stages of the biofilm by scanning electron microscopy (SEM) in five out of five patients, and all five patients showed aberrant findings of the mucosal surface with various degrees of severity: from disarrayed cilia to complete absence of cilia and goblet cells (Ramadan H H, Sanclement J A, Thomas J G, "Chronic rhinosinusitis and biofilms," Otolaryngol Head Neck Surg, 2005; 132: 414-417). In most cases of CRS and *Pseudomonas aeruginosa* biofilms, clinical symptoms were refractory to culture-directed antibiotics, topical steroids, and nasal lavages, and only surgery (mechanical debridement) resulted in significant improvement (Ferguson B J, Stolz D B, "Demonstration of biofilm in human bacterial chronic rhinosinusitis," Am J Rhinol, 2005; 19: 452-457).

Chronic Otitis Media

Chronic Otitis Media (OM) involves inflammation of the middle-ear mucoperiosteal lining and is caused by a variety of microorganisms, including: *Streptococcus pneumoniae, Haemophilus influenzae, Moraxella catarrhalis*, group A beta-hemolytic *streptococci*, enteric bacteria, *Staphylococcus aureus, Staphylococcus epidermidis, Pseudomonas aeruginosa*, and other organisms; mixed cultures can also be isolated (Feigin R D, Kline M W, Hyatt S R, and Ford III K L, "Otitis media," pp. 174-189. In: Textbook of pediatric infectious diseases, Feigin R D and Cherry J D (ed.), 3-rd ed., vol. 1, 1992, W. B. Saunders Co., Philadelphia, Pa.); (Giebink G S, Juhn S K, Weber M L, and Le C T, "The bacteriology and cytology of chronic otitis media with effusion," Pediatric Infect. Dis., 1982; 1: 98-103). Chronic OM as a biofilm-related infection was demonstrated in clinical specimens and in animal models. Scanning electron microscopy provided evidence of *Haemophilus influenzae* biofilm on the middle-ear mucosal surfaces of chinchillas that had been injected with a culture of this organism (Hayes J D, Veeh R, Wang X, Costerton J W, Post J C, and Ehrlich G D, Abstr. 186, Am. Soc. Microbiol. Biofilm, 2000; Conf. 2000); (Hong W, Mason K, Jurcisek J, Novotny L, Bakaletz L O, and Swords W E, "Phosphorylcholine decreases early inflammation and promotes the establishment of stable biofilm communities of nontypeable *Haemophilus influenzae* strain 86-028NP in a chinchilla model of otitis media,"

Infect Immun, 2007b; 75: 958-965). Biofilm aggregates of *Streptococcus pneumoniae, Haemophilus influenzae* and *Moraxella catarrhalis* were detected in biopsies of the middle-ear mucosal lining in children with chronic or recurrent OM undergoing TT placement for treatment, but not in the middle-ear mucosal biopsies from patients undergoing surgery for cochlear implantation (Hall-Stoodley L, Hu F Z, Gieseke A, Nistico L, Nguyen D, Hayes J, et al., "Direct detection of bacterial biofilms on the middle-ear mucosa of children with chronic otitis media," JAMA, 2006; 296: 202-211.)

In chronic OM with effusion, the presence of highly viscous fluid in the middle ear requires in many cases the implantation of tympanostomy tubes (TT) to alleviate pressure build-up and hearing loss. Tympanostomy tubes are subject to contamination, and biofilms build up on their inner surfaces. The investigation of colonization and biofilm development by *Pseudomonas aeruginosa, Staphylococcus aureus*, and *Staphylococcus epidermidis* on various tympanostomy tubes, provided evidence that all three organisms developed biofilms on the Armstrong silicone and the silver oxide-coated Armstrong-style silicone tubes; *Pseudomonas aeruginosa* also developed biofilms on the fluoroplastic tubes; only the ionized silicone tubes remained free of contamination and biofilms (Biedlingmaier J F, Samaranayake R, and Whelan P, "Resistance to biofilm formation on otologic implant materials," Otolaryngol Head Neck Surg, 1998; 118: 444-451). Silver oxide-impregnated silastic tubes lowered the incidence of postoperative otorrhea during the first postoperative week, possibly by preventing adherence and colonization of selected bacteria to the tube, but had no effect on the established infection in the middle ear (Gourin C G and Hubbell R N, "Otorrhea after insertion of silver oxide-impregnated silastic tympanostomy tubes," Arch. Otolaryngol Head Neck Surg, 1999; 125: 446-450). Bacterial biofilm was also detected on a human cochlear implant (Pawlowski K S, Wawro D, Roland P S, "Bacterial biofilm formation on a human cochlear implant," Otol Neurotol, 2005; 26: 972-975).

In the lower respiratory tract, microbial biofilms were associated with chronic bronchitis, chronic obstructive pulmonary disease, and pneumonia, especially in patients with cystic fibrosis. Scanning electron microscopy of clinical samples (sputum, bronchiolar lavage, lung and bronchial lining biopsies) demonstrated microbial biofilms either attached to mucosal linings or in the form of bacterial aggregates in mucus covering respiratory epithelium (Lam J, Chan R, Lam K, and Costerton J W, "Production of mucoid microcolonies by *Pseudomonas aeruginosa* within infected lungs in cystic fibrosis," Infect Immun, 1980; 28: 546-556); (Martinez-Solano L, Macia M D, Fajardo A, Oliver A, and Martinez J L, "Chronic *Pseudomonas aeruginosa* infection in chronic obstructive pulmonary disease," Clin Infect Dis, 2008; 47: 1526-1533); (Starner T D, Zhang N, Kim G, Apicella M A, and McCray P B Jr, "*Haemophilus influenzae* forms biofilms on airway epithelia: implications in cystic fibrosis," Am J Respir Crit Care Med, 2006; 174: 213-220); (Worlitzsch D, Tarran. R, Ulrich M, Schwab U, Cekici A, Meyer K C, et al., 2002, "Effects of reduced mucus oxygen concentration in airway *Pseudomonas* infections of cystic fibrosis patients," J Clin Invest, 2002; 109: 317-325); (Yang L, Haagensen J A, Jelsbak L, Johansen H K, Sternberg C, Høiby N, and Molin S, "In situ growth rates and biofilm development of *Pseudomonas aeruginosa* populations in chronic lung infections," J Bacteriol, 2008; 190: 2767-2776).

Cystic Fibrosis

Cystic fibrosis (CF), a chronic disease of the lower respiratory system, is the most common inherited disease: 70% of patients with CF are defective in the cystic fibrosis transmembrane conductance regulator protein (CFTR), which functions as a chloride ion channel protein, resulting in altered secretions in the secretory epithelia of the respiratory tract. In CF, there is a net deficiency of water, which hinders the upward flow of the mucus layer thus altering mucociliary clearance. Decreased secretion and increased absorption of electrolytes lead to dehydration and thickening of secretions covering the respiratory mucosa (Koch C and Høiby N, "Pathogenesis of cystic fibrosis," Lancet, 1993; 341: 1065-1069). The hyperviscous mucus is thought to increase the incidence of bacterial lung infections in CF patients. *Staphylococcus aureus* is usually the first pulmonary isolate from these patients, followed by *Haemophilus influenzae*. Both of these infections can be treated effectively with antibiotics, but on persistence, they usually form biofilm and predispose the CF-affected lung to colonization with *Pseudomonas aeruginosa* (colonization rate of ~80%) and *Burkholderia cepacia* with lethal consequences (Govan J R, and Deretic V, "Microbial pathogenesis in cystic fibrosis: mucoid *Pseudomonas aeruginosa* and *Burkholderia cepacia*," Microbiol. Rev., 1996; 60: 539-574). As was demonstrated in clinical studies, both organisms were non-mucoid during initial colonization, but on persistence in the lungs of patients with CF they ultimately undergo changes to mucoid phenotype within a period of time from months to years (Koch C and Høiby N, "Pathogenesis of cystic fibrosis," Lancet, 1993; 341: 1065-1069). The mucoid material, which was shown to be a polysaccharide substance, later identified as alginate, was transiently produced by laboratory strain of *P. aeruginosa*, following adherence to the surface (Hoyle B D, Williams L J, and Costerton J W, "Production of mucoid exopolysaccharide during development of *Pseudomonas aeruginosa* biofilms," Infect. Immun., 1993; 61: 777-780). It has been proposed that several in vitro conditions, such as nutrient limitation, the addition of surfactants, and suboptimal levels of antibiotics, may result in mucoidy due to increased production of alginate (May T B, Shinabarger D, Maharaj R, Kato J, Chu L, DeVault J D, Roychoudhury S, Zielinski N A, Berry A, Rothmel R K, Misra T K, and Chakrabarty A M, "Alginate synthesis by *Pseudomonas aeruginosa*: a key pathogenic factor in chronic pulmonary infections of cystic fibrosis patients," Clin. Microbiol. Rev., 1991; 4: 191-206). Early antimicrobial treatment with oral ciprofloxacin and inhaled colistin has been shown to postpone chronic infection with *Pseudomonas aeruginosa* for several years (Koch C and Høiby N, "Pathogenesis of cystic fibrosis," Lancet, 1993; 341: 1065-1069).

Periodontal Diseases

Periodontal diseases include infections of the supporting tissues of teeth, ranging from mild and reversible inflammation of the gums (gingiva) to chronic destruction of periodontal tissues (gingiva, periodontal ligament, and alveolar bone) and exfoliation of the teeth. The subgingival crevice (the channel between the tooth root and the gum) is the primary site of periodontal infection and will deepen into a periodontal pocket with the progression of the disease (Lamont R J and Jenkinson H F, "Life below gum line: pathogenic mechanisms of *Porphyromonas gingivalis*," Microbiol. Mol. Biol. Rev., 1998; 62: 1244-1263). Microorganisms isolated from patients with moderate periodontal disease include *Fusobacterium nucleatum, Peptostreptococcus micros, Eubacterium timidum, Eubacterium brachy, Lactobacillus* spp., *Actinomyces naeslundii, Pseudomonas*

*anaerobius, Eubacterium* sp. strain D8, *Bacteroides intermedius, Fusobacterium* spp., *Selenomonas sputigena, Eubacterium* sp. strain D6, *Bacteroides pneumosintes*, and *Haemophilus aphrophilus*, and these bacteria are not found in healthy patients (Moore W E C, Haldeman L V, Cato E P, Smilbert R M, Burmeister J A, and Ranney R R, "Bacteriology of moderate (chronic) periodontitis in mature adult humans," Infect. Immun., 1993; 42: 510-515). In adult patients with periodontitis, subgingival plaques harbor spirochetes and cocci, and the predominant microorganisms of active lesions in subgingival areas include *Fusobacterium nucleatum, Wolinella recta, Bacteroides intermedius, Bacteroides forsythus*, and *Bacteroides gingivalis* (*Porphyromonas gingivalis*) (Omar A A, Newman H N, and Osborn J, "Darkground microscopy of subgingival plaque from the top to the bottom of the periodontal pocket," J. Clin. Periodontol., 1990; 17: 364-370); (Dzink J I, Socransky S S, and Haffajee A D, "The predominant cultivable microbiota of active and inactive lesions of destructive periodontal diseases," J. Clin. Periodontol., 1988; 15: 316-323).

Proteinaceous conditioning films (called acquired pellicle), developed on the exposed surfaces of enamel almost immediately after cleaning of the tooth surface, comprises albumin, lysozyme, glycoproteins, phosphoproteins, lipids, and gingival crevice fluid. Within hours of pellicle formation, single cells of primarily gram-positive cocci and rod-shaped bacteria from the normal oral flora colonize these surfaces, binding directly to the pellicle through the production of extracellular glucans (Kolenbrander P E and London J, "Adhere today, here tomorrow: oral bacterial adherence," J. Bacteriol., 1993; 175: 3247-3252). After several days, actinomycetes predominate followed by co-aggregation of various microorganisms, resulting in the development of early biofilm with characteristic polysaccharide matrix and polymers of salivary origin, with subsequent (within 2 to 3 weeks) formation of the dental plaque if left undisturbed (Marsh P D, "Dental plaque," pp. 282-300. In: Microbial biofilms. 1995; Lappin-Scott H M and Costerton J W (ed.), Cambridge University Press, Cambridge, United Kingdom.). Plaque can be mineralized with calcium and phosphate ions (called calculus or tartar) and develop more extensively in protected areas (between the teeth, and between the tooth and gum). With the increase of the plaque mass in these protected areas, the beneficial buffering and antimicrobial properties of saliva decrease, leading to dental caries or periodontal disease. Clinical research data show that control of supragingival plaque by professional tooth cleaning and personal hygienic efforts can prevent gingival inflammation and adult periodontitis (Corbet E F and Davies W I R, "The role of supragingival plaque in the control of progressive periodontal disease," J. Clin. Periodontol., 1993; 20: 307-313).

Chronic Bacterial Prostatitis

The prostate gland may become infected by bacteria ascended from the urethra or by reflux of infected urine into the prostatic ducts emptying into the posterior urethra (Domingue G J and Hellstrom W J G, "Prostatitis," Clin. Microbiol. Rev., 1998; 11: 604-613). If bacteria were not eradicated with antibiotic therapy at the early stage of infection, they continue to persist and can form sporadic microcolonies and biofilms that adhere to the epithelial cells of the prostatic duct system, resulting in chronic bacterial prostatitis. The microorganisms involved in this process include: *E. coli* (most common isolate), *Klebsiella, Enterobacteria, Proteus, Serratia, Pseudomonas aeruginosa, Enterococcus fecalis, Bacteroides* spp., *Gardnerella* spp., *Corynebacterium* spp., and Coagulase-negative *Staphylococci* (CONS) (Nickel J C, Costerton J W, McLean R J C, and Olson M, "Bacterial biofilms: influence on the pathogenesis, diagnosis, and treatment of the urinary tract infections," J. Antimicrob. Chemother., 1994; 33 (Suppl. A): 31-41). The biopsies from patients with chronic bacterial prostatitis examined by either scanning electron microscopy or transmission electron microscopy, demonstrated bacteria present in glycocalyx-encased microcolonies, firmly adherent to the ductal and acinar mucosal layers (Nickel J C and Costerton J W, "Bacterial localization in antibiotic-refractory chronic bacterial prostatitis," Prostate, 1993; 23: 107-114). Sporadic microcolonies of CoNS in the intraductal space have been shown to be enveloped in a dehydrated slime matrix (Nickel J C and Costerton J W, "Coagulase-negative *staphylococcus* in chronic prostatitis," J. Urol., 1992; 147: 398-401). Treatment failures are common in chronic bacterial prostatitis due to the local environment and biofilm formation, with changes in bacterial metabolism and possible development of resistance to antimicrobials. In order to increase the effectiveness of the antimicrobial treatment, it has been proposed to deliver higher antibiotic concentrations directly to the biofilm within the prostatic ducts (Nickel J C, Costerton J W, Mclean R J C, and Olson M, "Bacterial biofilms: influence on the pathogenesis, diagnosis, and treatment of the urinary tract infections," J. Antimicrob. Chemother., 1994; 33 (Suppl. A): 31-41).

Biofilms on Medical Devices

Over the last 20 years, biofilms on various medical devices, including prosthetic heart valves, central venous catheters, urinary (Foley) catheters, contact lenses, intrauterine devices, and dental unit water lines, have been studied using viable bacterial culture techniques and scanning electron microscopy, and for certain devices (contact lenses and urinary catheters) additional evaluation of susceptibility of various materials to bacterial adhesion and biofilm formation have also been implemented (Costerton J W, Stewart P S, and Greenberg E P, "Bacterial biofilms: a common cause of persistent infections," Science, 1999; 284: 1318-1322); (Donlan R M and Costerton J W, "Review. Biofilms: Survival mechanisms of clinically relevant microorganisms," Clinical Microbiology Reviews, April 2002; 167-193).

Prosthetic Heart Valves

Prosthetic valve endocarditis (PVE) is a microbial infection of the valve and surrounding tissues of the heart, ranging between 0.5% and 4%, and is similar for both types of valves currently used—mechanical valves and bioprostheses (Douglas J L and Cobbs C G, "Prosthetic valve endocarditis," pp. 375-396. In: Infective endocarditis, Kaye D. (ed.), 2-nd ed., 1992; Raven Press LTD., New York, N.Y.). Tissue damage resulting from surgical implantation of the prosthetic valve, leads to accumulation of platelets and fibrin at the suture site and on the device, providing a favorable environment for bacterial colonization and biofilm development. PVE is predominantly caused by microbial colonization of the sewing cuff fabric. The microorganisms commonly invade the valve annulus, potentially promoting separation between the valve and the tissue resulting in leakage. Infectious microorganisms involved in PVE include *Staphylococcus epidermidis* (at the early stages), followed by *Streptococci*, CoNS, *Enterococci, Staphylococcus aureus*, gram-negative Coccobacilli, fungi, and *Streptococcus viridans* spp. (the most common microorganism isolated during late PVE) (Hancock E W, "Artificial valve disease," pp. 1539-1545. In: The heart arteries and veins; Schlant R C, Alexander R W, O'Rourke R A, Roberts R, and Sonnenblick E H (ed.), 8-th ed., 1994; vol. 2. McGraw-Hill, Inc., New York, N.Y.); (Illingworth B L, Twenden K, Schroeder R F, and Cameron J D, "In vivo efficacy of silver-coated (silzone) infection-resistant polyester fabric against a biofilm producing bacteria, *Staphylococcus epidermidis*, J. Heart Valve Dis., 1998; 7: 524-530); (Karchmer A W and Gibbons G W, "Infections of prosthetic heart valves and vascular grafts," pp. 213-249. In: Infections associated with indwelling medical devices; Bisno A L and Waldovogel F A (ed.), 1994, 2-nd ed. American Society for Microbiology, Washington, D.C.).

Central Venous Catheters

For Central Venous Catheters (CVCs), the device-related infection rate is 3% to 5%. Infectious biofilms are universally present on CVCs and can be associated with either the outside surface of the catheter or the inner lumen. Colonization and biofilm formation may occur within 3 days of catheterization. Short-term catheters (in place for less than 10 days) usually have more extensive biofilm formation on the external surfaces, and long-term catheters (up to 30 days) have more extensive biofilm on the internal lumen. (Raad I I, Costerton J W, Sabharwal, Sacilowski U M, Anaissie W, and Bodey G P, "Ultrastructural analysis of indwelling vascular catheters: a quantitative relationship between luminal colonization and duration of placement," J. Infect. Dis., 1993; 168: 400-407). Colonizing microorganisms originate either from the skin insertion site, migrating along the external surface of the device, or from the hub, due to manipulation by health care workers, migrating along the inner lumen (Elliott T S J, Moss H A, Tebbs S E, Wilson I C, Bonser R S, Graham T R, Burke L P, and Faroqui M H, "Novel approach to investigate a source of microbial contamination of central venous catheters," Eur. J. Clin. Microbiol. Infect. Dis., 1997; 16: 210-213). Because the device is in direct contact with the bloodstream, the surface becomes coated with platelets, plasma and tissue proteins such as albumin, fibrinogen, fibronectin, and laminin, forming conditioning films to which the bacteria are adherent: *Staphylococcus aureus* adheres to fibronectin, fibrinogen, and laminin, and *Staphylococcus epidermidis* adheres only to fibronectin. Organisms colonizing CVCs include CoNS, *Staphylococcus aureus, Pseudomonas aeruginosa, Klebsiella pneumoniae, Enterococcus fecalis*, and *Candida albicans* (Elliott T S J, Moss H A, Tebbs S E, Wilson I C, Bonser R S, Graham T R, Burke L P, and Faroqui M H, "Novel approach to investigate a source of microbial contamination of central venous catheters," Eur. J. Clin. Microbiol. Infect. Dis., 1997; 16: 210-213).

Urinary Catheters

Urinary catheters are subject to bacterial contamination regardless of the types of the catheter systems. In open systems, the catheter draining into an open collection container becomes contaminated quickly, and patients commonly develop Urinary Tract Infection (UTI) within 3 to 4 days. In closed systems, when the catheter empties in a securely fastened plastic collecting bag, the urine from the patient can remain sterile for 10 to 14 days in approximately half the patients (Kaye D and Hessen T, "Infections associated with foreign bodies in the urinary tract," pp. 291-307. In: Infections associated with indwelling medical devices; Bisno A L and Waldovogel F A (ed.), 1994; 2-nd ed., American Society for Microbiology, Washington, D.C.). Regardless of the type of the system, with short-term catheterization (up to 7 days), 10% to 50% of patients develop UTI, and with long-term catheterization (28 days and longer) essentially all patients develop UTI (Stickler D J, "Bacterial biofilms and the encrustation of urethral catheters," Biofouling, 1996; 94: 293-305). The risk of catheter-associated UTI increases by approximately 10% for each day the catheter is in place. Initially, catheters are colonized by a single microorganism, such as *Staphylococcus epidermidis, Enterococcus fetalis, E. coli, Proteus mirabilis*. Later, the number and diversity of bacteria increase, with mixed communities containing *Providencia stuartii, Pseudomonas aeruginosa, Proteus mirabilis, Klebsiella pneumoniae, Morganella morganii, Acinetobacter calcoaceticus*, and *Enterobacter aerogenes* (McLean R J C, Nickel J C, and Olson. M E, "Biofilm associated urinary tract infections," pp. 261-273. In: Microbial biofilms; 1995, Lappin-Scott H M and Costerton J W (ed.), Cambridge University Press, Cambridge, United Kingdom.).

Both in vivo and in vitro studies by scanning electron microscopy and transmission electron microscopy provide evidence for biofilm formation on catheters. The thickness of biofilm on silicone and silicone-coated Foley catheters from patients undergoing long-term catheterization ranges from 200 μm to 500 μm, with the thickest biofilms formed by *E. coli* and *Klebsiella pneumoniae* (up to 490 μm). The thinnest biofilms were formed by *Morganella morganii* and diphtheroids (the average ~10 μm), and these biofilms were also patchy (Ganderton L, Chawla J, Winters C, Wimpenny J, and Stickler D, "Scanning electron microscopy of bacterial biofilms on indwelling bladder catheters," Eur. J. Clin. Microbiol. Infect. Dis., 1992; 11: 789-796).

Urinary catheter biofilms are unique, because certain microorganisms produce enzyme urease which hydrolyzes the urea of the urine to form free ammonia, thus raising the local pH and allowing precipitation of minerals hydroxyapatite (calcium phosphate) and struvite (magnesium ammonium phosphate). These minerals become deposited in the catheter biofilms, forming a mineral encrustation which can completely block a urinary catheter within 3 to 5 days (Tunney M M, Jones D S, and Gorman S P, "Biofilm and biofilm-related encrustations of urinary tract devices," Methods Enzymol., 1999; 310: 558-566). The primary urease-producing organisms in urinary catheters are *Proteus mirabilis, Morganella morganii, Pseudomonas aeruginosa, Klebsiella pneumoniae*, and *Proteus vulgaris*. Mineral encrustations were observed only in catheters containing these bacteria Stickler D, Morris N, Moreno M C, and Sabbuba N, "Studies on the formation of crystalline bacterial biofilms on urethral catheters," Eur. J. Clin. Microbiol. Infect. Dis., 1998; 17: 649-652); (Stickler D, Ganderton L, King J, Nettleton J, and Winters C, "*Proteus mirabilis* biofilms and the encrustation of urethral catheters," Urol. Res., 1993; 21: 407-411).

Contact Lenses

Bacteria adhere readily to both types of contact lenses: soft contact lenses (made of either hydrogel or silicone) and hard contact lenses constructed of polymethylmethacrylate. Initial adhesion of *Pseudomonas aeruginosa* to hydrogel contact lenses, resulted within 2 hours in biofilm formation with characteristic extracellular matrix polymers observed by transmission electron microscopy and ruthenium red staining (Miller M J and Ahearn G, "Adherence of *Pseudomonas aeruginosa* to hydrophilic contact lenses and other substrata," J. Clin. Microbiol., 1987; 25: 1392-1397). The degree of attachment depended on various factors, including the nature of the substrate, pH, electrolyte concentration, ionic charge of the polymer, and bacterial strain tested.

Organisms that have been shown to adhere to contact lenses include: *Pseudomonas aeruginosa, Staphylococcus aureus, Staphylococcus epidermidis, Serratia* spp., *E. coli, Proteus* spp., and *Candida* spp. (Dart J K G, "Contact lens and prosthesis infections," pp. 1-30. In: Duane's foundations of clinical ophthalmology; Tasman W and Jaeger E A (ed.), 1996; Lippincott-Raven, Philadelphia, Pa.). An established biofilm was detected on the lens removed from a patient with *P. aeruginosa* keratitis, as well as from the patients with clinical diagnosis of microbial keratitis, in several cases containing multiple species of bacteria or bacteria and fungi (Stapleton F and Dart J, "*Pseudomonas* keratitis associated with biofilm formation on a disposable soft contact lens," Br. J. Ophthalmol., 1995; 79: 864-865); (McLaughlin-Borlace L, Stapleton F, Matheson M, and Dart J K G, "Bacterial biofilm on contact lenses and lens storage cases in wearers with microbial keratitis," J. Appl. Microbiol., 1998; 84: 827-838).

The lens case has been implicated as the primary source of microorganisms for contaminated lenses and lens disinfectant solutions, with contaminated storage cases in 80% of asymptomatic lens users (McLaughlin-Borlace L, Stapleton F, Matheson M, and Dart J K G, "Bacterial biofilm on contact lenses and lens storage cases in wearers with microbial keratitis," J. Appl. Microbiol., 1998; 84: 827-838). Also, the identical organisms were isolated from the lens cases and the corneas of infected patients. Additionally, protozoan Acanthamoeba has been shown to be a component of these biofilms (Dart J K G, "Contact lens and prosthesis infections," pp. 1-30. In: Duane's foundations of clinical ophthalmology; Tasman W and Jaeger E A (ed.), 1996; Lippincott-Raven, Philadelphia, Pa.); (McLaughlin-Borlace L, Stapleton F, Matheson M, and Dart J K G, "Bacterial biofilm on contact lenses and lens storage cases in wearers with microbial keratitis," J. Appl. Microbiol., 1998; 84: 827-838).

Dental Unit Water Lines

Dental procedures may expose both patients and dental professionals to opportunistic and pathogenic organisms originating from various components of the dental unit. Small-bore flexible plastic tubing supplies water (municipal or from separate reservoirs containing distilled, filtered, or sterile water) to different hand pieces (air-water syringe, the ultrasonic scaler, the high-speed hand piece), and elevated bacterial counts were detected in all these systems (Barbeau J, Tanguay R, Faucher E, Avezard C, Trudel L, Cote L, and Prevost A P, "Multiparametric analysis of waterline contamination in dental units," Appl. Environ. Microbiol., 1996; 62: 3954-3959); (Furuhashi M and Miyamae T, "Prevention of bacterial contamination of water in dental units," J. Hosp. Infect., 1985; 6: 81-88); (Mayo J A, Oertling K M, and Andrieu S C, "Bacterial biofilm: a source of contamination in dental air-water syringes," Clin. Prev. Dent., 1990; 12: 13-20); (Williams H N, Kelley J, Folineo D, Williams G C, Hawley C L, and Sibiski J, "Assessing microbial contamination in clean water dental units and compliance with disinfection protocol," JADA, 1994; 125: 1205-1211).

Organisms generally isolated from dental water units include *Pseudomonas* spp., *Flavobacterium* spp., *Acinetobacter* spp., *Moraxella* spp., *Achromobacter* spp., *Methylobacterium* spp., *Rhodotorula* spp., hyphomycetes (*Cladosporium* spp., *Aspergillus* spp., and *Penicillium* spp.), *Bacillus* spp., *Streptococcus* spp., CoNS, *Micrococcus* spp., *Corynebacterium* spp., and *Legionella pneumophila* (Tall B D, Williams H N, George K S, Gray R T, and Walch M, "Bacterial succession within a biofilm in water supply lines of dental air-water syringes," Can. J. Microbiol., 1995; 41: 647-654); (Whitehouse R L S, Peters E, Lizotte J, and Lilge C, "Influence of biofilms on microbial contamination in dental unit water," J. Dent., 1991; 19: 290-295); (Mills S E P, Lauderdale W, and Mayhew R B, "Reduction of microbial contamination in dental units with povidone-iodine 10%," JADA, 1986; 113: 280-284); (Atlas R M, Williams J F, and Huntington M K, "*Legionella* contamination of dental-unit waters," Appl. Environ. Microbiol., 1995; 61: 1208-1213); (Callacombe S J and Fernandes L L, "Detecting *Legionella pneumophila* in water systems: a comparison of various dental units," JADA, 1995; 126: 603-608); (Pankhurst C L, Philpott-Howard J N, Hewitt J H, and Casewell M W, "The efficacy of chlorination and filtration in the control and eradication of *Legionella* from dental chair water systems," J. Hosp. Infect., 1990; 16: 9-18). The variety of microorganisms observed, were embedded in an apparent polysaccharide matrix (Whitehouse R L S, Peters E, Lizotte J, and Lilge C, "Influence of biofilms on microbial contamination in dental unit water," J. Dent., 1991; 19: 290-295). Also, amebic trophozoites and cysts, and nematodes (in one biofilm sample) were also observed (Santiago J I, Huntington M K, Johnston A M, Quinn R S, and Williams J F, "Microbial contamination of dental unit waterlines: short- and long-term effects of flushing," Gen. Dent., 1994; 42: 528-535). A positive correlation was found between biofilm and water counts, and by 180 days of exposure, a thick, multiple layer of extracellular polymeric substances covered the entire surface of the dental unit water line (Tall B D, Williams H N, George K S, Gray R T, and Walch M, "Bacterial succession within a biofilm in water supply lines of dental air-water syringes," Can. J. Microbiol., 1995; 41: 647-654). Biofilms containing extensive extracellular polymer matrix and both mixed skin flora and aquatic bacteria, were also detected on the inner lumen of saliva ejectors (Barbeau J, ten Bocum L, Gauthier C, and Prevost A P, "Cross contamination potential of saliva ejectors used in dentistry," J. Hosp. Infect., 1998; 40: 303-311).

Methods of Treating Biofilms and Biofilm-Based Infections

Many biofilm control strategies have been proposed, applied mostly to biofilm formed on various medical devices, including long term antibiotics for patients using these devices, various antimicrobials to cover the surfaces of devices, various polymer materials, ultrasound, and low-strength electrical fields along with disinfectants.

For biofilm-based infections in the human body, a few approaches aimed to either eradicate or penetrate the extracellular polymeric substances have been offered: for example, a mixture of enzymes was effective in eradicating laboratory-grown biofilms of several different organisms (Johansen C P, Falholt P, and Gram L, "Enzymatic removal and disinfection of bacterial biofilm," Appl. Environ. Microbiol., 1997; 63: 3724-3728). Another more precise approach was identifying the polysaccharides for a specific organism in the biofilm and treating the biofilm with that enzyme: for example, the specific enzyme alginate lyase allowed more effective diffusion of gentamycin and tobramycin through alginate, the biofilm polysaccharide of mucoid *Pseudomonas aeruginosa* (Hatch R A, and Schiller N L, "Alginate lyase promotes diffusion of aminoglycosides through the extracellular polysaccharide of mucoid *Pseudomonas aeruginosa*," Antimicrob. Agents Chemother., 1998; 42: 974-977). In addition, for the management of biofilm infections, various antibiotics have been examined extensively in vitro and in vivo, including aminoglycosides, fluoroquinolones, macrolides, as well as the latest protein synthesis inhibitors (Linezolid and Quinupristin) clinically available and appear promising for treatment of in vivo biofilm infections (In: Biofilms, Infection, and Antimicrobial Therapy; Edited by Pace J L, Rupp M E, and Finch R G; Boca Raton, Fla.: CRC Press, 2006. Chapter 18, page 360).

A review of recent patent literature summarizes citations under six categories of current treatment approaches: 1)

antibiotics and small molecule inhibitors of new and established biofilms, 2) quorum sensing and signaling molecules inhibitors, 3) surface coating substances for inhibition of biofilm formation, 4) antibodies and vaccines for infectious biofilm treatment, 5) enzymes for degrading biofilms, and 6) bacteriophage treatment of infectious biofilms (Lynch A S and Abbanat D, "New antibiotic agents and approaches to treat biofilm-associated infections," Expert Opin. Ther. Patents, 2010; 20(10): 1373-1387).

Additional approaches involve the use of various natural substances and combined technologies. For example, naturally occurring impediments to biofilm adhesion have been proposed such as, oral-ficin, a cysteine protease derived from the *Ficus glabrata* tree, which prevents biofilm-forming bacteria from adhering to surfaces (Potera C, "A Potpourri of Probing and Treating Biofilms of the Oral Cavity," Microbe Magazine, October 2009). The ability of honey to prevent quorum sensing and thereby interfere with the formation or maintenance of biofilms suggests it can be a candidate substance for the management of infected wounds ("The role of biofilm in wounds," a thesis submitted to the University of Wales, Cardiff, UK, in candidature for Ph.D. by Okhiria O A, May 2010, Chapter 5: Antimicrobial effect of honey on biofilm and quorum sensing: 190-234).

An example of the use of combined technologies is the treatment of biofilm infections on implants using ultrasound in concert with antibiotics (Carmen J C, Roeder B L, Nelson J L, Robison Ogilvie R L, Robison R A, Schaalje G B, and Pitt W G, "Treatment of Biofilm Infections on Implants with Low-frequency Ultrasound and Antibiotics," Am J Infect Control. 2005, March; 33(2): 78-82).

Methods of Addressing Biofilm Contamination of Medical Equipment

Bacterial and fungal biofilms develop on the various types of medical equipment. This includes medical diagnostic devices, such as: stethoscopes, colposcopes, nasopharyngoscopes, angiography catheters, endoscopes, angioplasty balloon catheters; and various permanent, semi-permanent, and temporary indwelling devices, such as: contact lenses, intrauterine devices, dental implants, urinary tract prostheses and catheters, peritoneal dialysis catheters, indwelling catheters for hemodialysis and for chronic administration of chemotherapeutic agents (Hickman catheters), cardiac implants (pacemakers, prosthetic heart valves, ventricular assisting devices—VAD), synthetic vascular grafts and stents, prostheses, internal fixation devices, percutaneous sutures, tracheal and ventilator tubing, dispensing devices such as nebulizers, and cleaning devices such as sterilizers. Summarized herein are the current methods employed to diminish the presence of microbial biofilms and associated pathogens on medical equipment.

Implants

Biofilm infections associated with indwelling medical devices and implants are difficult to resolve using conventional antibiotics. Antibiotic treatment requires lengthy periods of administration, with combined antibiotics at high dose, or the temporary surgical removal of the device or associated tissue. Newer developments, aimed at interfering with the colonization process comprise, for example, new biomaterials, the co-application of acoustic energy or low-voltage electric currents with antibiotics and the development of specific anti-biofilm agents (Jass J, Surman S, and Walker J T, "Medical biofilms: detection, prevention, and control," Vol. 2, John Wiley, 2003: 261).

Central Venous Catheters

Several studies have examined the effect of various types of antimicrobial treatment in controlling biofilm formation on venous catheters. The methods and materials used include adding disinfectant to physiological flush of catheters for elimination of microbial colonization (Freeman R, Gould F K. "Infection and intravascular catheters," [letter]. J. Antimicrob. Chemother., 1985; 15: 258.), impregnation of catheters with polyantimicrobials (Darouiche R O et al., "A comparison of two antimicrobial-impregnated central venous catheters," N Engl J Med, 1999; 340: 1-8.), coating of catheters with surfactants to bond antibiotics to catheter surfaces (Kamal G. D., Pfaller M. A., Rempe L. E., Jebson P. J. R., "Reduced intravascular catheter infection by antibiotic bonding. A prospective, randomized, controlled trial", JAMA, 1991; 265: 2364-2368.), and the use of an attachable subcutaneous cuff containing silver ions inserted after local application of polyantibiotic (Flowers R. H., Schwenzer K. J., Kopel R. F., Fisch M. J., Tucker S. L, Farr B. M., "Efficacy of an attachable subcutaneous cuff for the prevention of intravascular catheter-related infection", JAMA, 1989; 261: 878-883).

Prosthetic Heart Valves

The pathogenesis of infection associated with implanted heart valves is related to the interface between the valve and surrounding tissue. Specifically, because implantation of a mechanical heart valve causes tissue damage at the site of its installation, microorganisms have an increased tendency to colonize such locations (Donlan R M, "Biofilms and Device-Associated Infections," Emerging Infectious Diseases Journal, March-April 2001; Vol. 7, No. 2: 277-281). Hence, biofilms resulting from such infections tend to favor development on the tissue surrounding the implant or the sewing cuff fabric used to attach the device to the tissue. Silver coating of the sewing cuff has been found to reduce such infections (Illingworth B L, Tweden K, Schroeder R F, Cameron J D, "In vivo efficacy of silver-coated (Silzone) infection-resistant polyester fabric against a biofilm-producing bacteria, *Staphylococcus epidermidis*", J Heart Valve Dis 1998; 7: 524. Abstract); (Carrel T, Nguyen T, Kipfer B, Althaus U, "Definitive cure of recurrent prosthetic endocarditis using silver-coated St. Jude medical heart valves: a preliminary case report," J Heart Valve Dis., 1998; 7: 531. Abstract.).

Urinary Catheters

Conventional approaches to the treatment of urinary catheter biofilms include: the use of antimicrobial ointments and lubricants, instillation or irrigation of the bladder with antimicrobials, use of the collection bags containing antimicrobial agents, catheter impregnation with antimicrobial agents, and the use of systemic antibiotics (Kaye D, Hessen M T, "Infections associated with foreign bodies in the urinary tract," In: Bisno A. L., Waldovogel F. A., editors. Infections associated with indwelling medical devices. 2nd ed. Washington: American Society for Microbiology; 1994; pp. 291-307). Such approaches have been found to have limited efficacy, although silver impregnation of catheters has been found to delay onset of bacteriuria (Donlan R M, "Biofilms and Device-Associated Infections," Emerging Infectious Diseases Journal, March-April 2001; Vol. 7, No. 2: 277-281). From various materials used for catheter construction, silicone catheters obstruct less often than latex, Teflon, or silicone-coated latex in patients prone to catheter encrustation (Sedor J and Mulholland S G, "Hospital-acquired urinary tract infections associated with indwelling catheter," Urol. Clin. N. Am., 1999; 26: 821-828).

A new product, the UroShield™ System, produced by NanoVibronix uses low cost disposable ultrasonic actuators which energize all surfaces of the catheter thereby interfering with the attachment of bacteria, the initial step in biofilm formation (Nagy K, Köves B, Jäckel M, Tenke P, "The effectiveness of acoustic energy induced by UroShield device in the prevention of bacteriuria and the reduction of patient's complaints related to long-term indwelling urinary catheters," Poster presentation at 26th Annual Congress of the European Association of Urology (EAU); Vienna, March 2011: No. 483. Abstract.).

Dialysis Systems

The development of biofilms throughout hemodialysis systems has been substantiated. In fact, some cases have been suspicious for the outbreak of infection within dialysis centers. Furthermore, the endotoxins and other cytokines in these biofilms can cross the dialysis membrane and trigger the inflammatory response in the patients (Vincent F C, Tibi A R, and Darbord J C. "A bacterial biofilm in a hemodialysis system. Assessment of disinfection and crossing of endotoxins," ASAIO Trans., 1989; 35: 310-313). In a study specific to the removal of biofilms from dialysis tubing, the efficacy of 21 different decontamination procedures was ascertained with the most effective treatment determined to be an acid pre-treatment, followed by use of a concentrated bleach solution; treatments performed at high temperature did not improve the removal of biofilm (Marion-Ferey K, et al., "Biofilm removal from silicone tubing: an assessment of the efficacy of dialysis machine decontamination procedures using an in vitro model," Journal of Hospital Infection, 2003; 53(1): 64-71).

Given the challenge of removing biofilms from the in-place water systems found in clinical environments, a multi-step cleaning (removal of organic material), descaling (removal of inorganic material), and disinfection (removal of microorganisms) process is suggested. The most common current protocols include the following: a) citric acid followed by bleach, b) bleach alone, c) peracetic acid with acetic acid and hydrogen peroxide (PAA), d) citric acid followed by autoclaving, e) citric acid at elevated temperature, f) glycolic acid at elevated temperature, g) hot water, and h) citric acid followed by PAA. All of these disinfection protocols appear to be highly efficient with respect to microbial killing, but were inefficient in reducing the amount of biofilm on affected surfaces.

No treatment thus far has shown complete biofilm removal (and consequently endotoxins) from silicone surfaces. Descaling by itself is inadequate, even at high temperature. Bleach appears to be a relatively good solitary agent for biofilm removal. Additionally, UV irradiation has been shown to have limited impact on biofilms; and ozone has demonstrated a higher removal efficacy, but limited biofilm killing. It has been postulated that destruction of both the bacteria and associated endotoxins may be possible if super-oxidative concentrations can be achieved ("The Role of Biofilms in Device-Related Infections," Ed. By Shirtliff M and Leid J G; Springer-Verlag, Berlin, 2009).

Endoscopes

In a comparative study of the efficiency of numerous detergents to remove endoscope biofilms, it was determined that "many commonly used enzymatic cleaners fail to reduce the viable bacterial load or remove the bacterial EPS" (Vickery K, Pajkos A, and Cossart Y," Removal of biofilm from endoscopes: evaluation of detergent efficiency, "Am J Infect Control. 2004, May; 32(3): 170-176). Only one cleaner containing no enzymes (produced by Whiteley Medical, Sydney, Australia) significantly reduced bacterial viability and residual bacterial exopolysaccharide matrix.

Noteworthy is U.S. Pat. No. 6,855,678, in which it is disclosed that through the use of scanning electron microscopy, it has been observed that biofilm consists of a number of layers and most importantly, there exists a thin layer of biofilm which is adjacent and attaches tightly to the surface of medical apparatus. The treatment formulation advocated herein includes in combination surfactants, solvents, co-solvents, nitrogen containing biocide, and organic chelating agents. This composition provides a simple non-corrosive, near neutral chemical detergent product that reliably cleans and disinfects endoscopes and other-medical apparatus. The hypothesized method of action is that a) the solvent and co-solvent (example solvents include low molecular weight polar water soluble solvents such as primary and secondary alcohols, glycols, esters, ketones, aromatic alcohols, and cyclic nitrogen solvents containing 8 or less carbon atoms, example co-solvents include low molecular weight amine, amide, and methyl and ethyl derivatives of amides) act to swell the biofilm, b) the organic chelating agent in combination with the surfactant increases the ability of the nitrogen containing biocide to penetrate the biofilm, and c) the organic chelating agent in combination with the nitrogen containing biocide act to work synergistically to dislodge the biofilm and/or kill the microorganisms therein.

Contact Lenses

Various cleaning solutions were tested against bacterial biofilms on contact lens storage cases, including quaternary ammonium compounds, chlorhexidine gluconate, and hydrogen peroxide 3%. Hydrogen peroxide 3% was most effective in inactivating 24 hr-old biofilms formed by *Pseudomonas aeruginosa, Staphylococcus epidermidis*, and *Streptococcus pyogenes*. Biofilm of *Candida albicans* was highly resistant to all of these treatments, and *Serratia marcescens* could grow in chlorhexidine disinfectant solutions (Wilson L A., Sawant A D, and Ahearn D G, "Comparative efficacies of soft contact lens disinfectant solutions against microbial films in lens cases," Arch. Ophthalmol., 1991; 109: 1155-1157); (Gandhi P A, Sawant A D, Wilson L A, and Ahearn D G, "Adaptation and growth of *Serratia marcescens* in contact lens disinfectant solutions containing chlorhexidine gluconate," Appl. Environ. Microbiol., 1993; 59: 183-188). It has been found that sodium salicylate decreased initial bacterial adherence to lenses and lens cases (Farber B F, His-Chia H, Donnenfield E D, Perry H D, Epstein A, and Wolff A, "A novel antibiofilm technology for contact lens solutions," Ophthalmology, 1995; 102: 831-836).

Dental Unit Water Lines

Dental unit water lines are ideal for colonization with aquatic bacteria and biofilm formation due to their small diameter, very high surface-to-volume ratio, and relatively low flow rates. Currently used flushing as treatment for reducing planktonic bacterial load that originates from the tubing biofilm, does not provide sufficient results, and flushing alone is ineffective (Santiago J I, Huntington M K, Johnston A M, Quinn R S, and Williams J F, "Microbial contamination of dental unit waterlines: short- and long-term effects of flushing," Gen. Dent., 1994; 42: 528-535). Added povidone-iodine reduced contamination between 4 and 5 log fewer bacteria per ml initially, but the levels returned to pretreatment within 22 days (Mills S E, Lauderdale P W, and Mayhew R B, "Reduction of microbial contamination in dental units with povidone-iodine 10%," JADA, 1986; 113: 280-284). Treatment with 0.5 to 1 ppm free chlorine for 10 min. each day reduced normal bacterial counts by 2 logs from pretreatment levels, but the counts increased again after chlorination was discontinued (Feigin R D and Henriksen K, "Methods of disinfection of the water system of dental units by water chlorination," J. Dent. Res., 1988; 67: 1499-1504). Chlorination with bleach (1:10 solution) of water systems already contaminated with bacterial biofilms was ineffective in removing them (Murdoch-Kinch C A, Andrews N A, Atwan S, Jude R, Gleason M J, and Molinari J A, "Comparison of dental water quality management procedures," JADA, 1997; 128: 1235-1243).

Biofilms in Industrial Applications (Pipelines, Marine Biofouling, Food Sanitation, and HVAC)

Industrial systems suffer a number of deleterious effects due to the presence of biofilms. For heating and cooling systems, as well as oil, water, and gas distributions systems, these effects include flow restrictions in pipelines, flow contamination, and corrosion. For marine systems such as ships, biofouling of hulls can lead to tremendous loss of ship fuel efficiency owing to increased drag of the hull.

Current Approaches for Treating Biofilms in Water, Oil and Gas Distribution Systems In industrial systems for the distribution of water, oil, and gas, biofilms can form heavy biomass that can reduce the effective diameter of a pipe or other conduit at a particular point or increase friction along the flow path in the conduit. This increases resistance to flow through the conduit, reduces the flow volume, increases pump power consumption, decreasing the efficiency of industrial operations. Further, this biomass can serve as a source of contamination to flowing water or oil. Additionally, most biofilms are heterogeneous in composition and structure which leads to the formation of cathodic and anodic sites within the underlying conduit metal thereby contributing to corrosion processes.

Currently, for pipeline treatment of biofilms, there is a trend to use strong oxidizing biocides such as chlorine dioxide in cooling systems and ozone in water distribution systems since low levels of chlorine have been found to be ineffective against biofilms. Also, a number of non-oxidizing biocides are available, which are effective but their long-term effects on the environment are still unclear. New techniques for biofilm control, such as ultrasound, electrical fields, hydrolysis of EPS and methods altering biofilm adhesion and cohesion are still in their infancy at the laboratory level and are yet to be successfully demonstrated in large industrial systems (Sriyutha Murthy P and Venkatesan R, "Industrial Biofilms and Their Control". In: Marine and Industrial Biofouling; Editors: Fleming H, Murthy P, Venkatesan R, and Cooksey K; Springer-Verlag, 2010).

One of the major economic losses faced by the oil and gas companies is due to pipeline corrosion. The internal corrosion of the pipelines is basically caused by sulfate reducing bacteria (SRB). SRB are anaerobic and responsible for most instances of accelerated corrosion damage. For biofilms created by SRB, some newer strategies include the use of: a) calcium or sodium nitrates which encourage more benign nitrate reducing bacteria to compete with SRB, b) molybdate as a metabolic inhibitor preventing sulfate reduction, c) anthraquinone which prohibits sulfide production and its incorporation into the biofilm, and d) dispersants such as filming amine technology which prevent biofilm adhesion. Also, since there is no continuous water phase in oil pipelines (under typical flow conditions) by which to dose bactericides, the use of water-oil emulsions have been suggested ("Petroleum Microbiology"; edited by Ollivier B and Magot M, ASM Press, 2005).

An example of the more recent biofilm altered adhesion concepts includes the disclosure of International Patent Application PCT/US2006/028353 describing a non-toxic, peptide-based biofilm inhibitor that prevents *Pseudomonas aeruginosa* colonization of stainless steel (and likely a wide variety of other metal surfaces) and non-metallic surfaces. The compositions and methods describe a very high affinity peptide ligand that binds specifically to stainless steel and other surfaces to prevent *Pseudomonas* biofilm formation. Another example of an inhibitor of biofilm adhesion is the technology being developed by Australian firm BioSignal Ltd. involving the use of furanones from the red seaweed Delisea pulchra, which effectively avoids a broad spectrum of bacterial infections without inciting any bacterial resistance to its defensive chemistry. Furanones produced by this seaweed, bind readily to the same specific protein-covered bacterial receptor sites that receive the bacterial signaling molecules (N-acyl homoserine lactone) which normally induce surface colonization. BioSignal Ltd. is targeting the use of synthetic furanones to block bacterial communication and thereby prevent bacteria from forming groups and biofilms in applications including pipelines, HVAC, and water lines treatment.

Methods of Decontamination of Food Processing, Storage, and Transport Systems in the Food Industry In addition to the more conventional means of decontamination discussed above for other industrial applications, recently, the food industry has embarked upon the use of enzyme-based schemes that have been carried over from the bio-processing of food stuffs. Specifically, efforts have been undertaken to find ways to enzymatically degrade the EPS itself and thereby contribute to the removal of biofilms. Largely, these efforts have been directed at destruction of the polysaccharide framework of the EPS. A premier example is found in the U. S. Patent Application 20110104141 to Novozyme which discloses the use of alpha-amylase as a primary enzyme for the breakdown of biofilm polysaccharides with the potential inclusion of additional enzymes such as aminopeptidase, amylase, carbohydrase, carboxypeptidase, catalase, cellulase, chitinase, cutinase, cyclodextrin glycosyltransferase, deoxyribonuclease, esterase, alpha-galactosidase, beta-galactosidase, glucoamylase, alpha-glucosidase, beta-glucosidase, haloperoxidase, invertase, laccase, lipase, mannosidase, oxidoreductases, pectinolytic enzyme, peptidoglutaminase, peroxidase, phytase, polyphenoloxidase, proteolytic enzyme, ribonuclease, transglutaminase, or xylanase. Products such as Biorem produced by Realco in coordination with Novozyme to target applications in the food and beverage industry exploit a two step cleaning process that invokes use of this kind of multienzyme mixture followed by application of a biocide.

In this industrial sector also, ultrasound has been found a useful tool; for sanitary control, it was found that the combination of chelating agents with ultrasound has been useful for removing selected biofilm-producing pathogens from metal surfaces (Oulahal N, Martial-Gros A, Bonneau M and Blum L J, "Combined effect of chelating agents and ultrasound on biofilm removal from stainless steel surfaces. Application to "*Escherichia coli* milk" and "*Staphylococcus aureus* milk" biofilms", Biofilms, 2004; 1: 65-73, Cambridge University Press.). The efficacy of such ensonification has been shown to exhibit dependency on the frequency and duty cycle of the energy (Nishikawa T, et al., "A study of the efficacy of ultrasonic waves in removing biofilms," Gerontology, September 2010; Vol 27, Issue 3: 199-206).

Current Methods for Treating Marine Biofouling

Biofouling occurs worldwide in various industries and one of the most common biofouling sites is on the hulls of ships, where barnacles are often found. A significant problem associated with biofilms on ships is the eventual corrosion of the hull, leading to the ship's deterioration. However, before corrosion occurs, organic growth can increase the roughness of the hull, which will decrease the vessel's maneuverability and increase hydrodynamic drag. Ultimately, biofouling can increase a ship's fuel consumption by as much as 30%. Parts of a ship other than the hull are affected as well: heat exchangers, water-cooling pipes, propellers, even the ballast water. Fishing and fish farming are also affected, with mesh cages and trawls harboring fouling organisms. In Australia, biofouling accounts for about 80% of the pearling industry's costs (Stanczak M, "Biofouling: It's Not Just Barnacles Anymore," CSA Discovery Guide, 2004; http://www.csa.com/discoveryguides/biofoul/overview.php.).

The traditional method of control is to coat exposed surfaces with an anti-fouling compounds. Most of these compounds rely on copper and tin salts that gradually leach from the coating and contaminate the surrounding environment. One of the most widely used coatings to date has been tributyl tin (TBT) which is highly toxic to marine organisms. Since it has been found to have unwanted side-effects on non-target organisms, a world-wide ban on its use was instituted in 2008. The race is on for an environmentally sound alternative (Scottish Association for Marine Science, http://www.sams.ac.uk/research/departments/microbial-molecular/mmb-project-themes/algal-biofilms.).

Hence, in maritime applications such as shipping, there is an unmet need for viable, cost-effective biofilm remediation.

Current Methods for Treating Biofilms in Heating, Ventilation and Air-Conditioning (HVAC) And Refrigeration Systems HVAC and refrigeration systems encounter problems associated with biofilms formed on cooling coils, drain pans, and in duct work subjected to water condensation. Biofilm formation on cooling coils diminishes heat exchange efficiency; its growth on other surfaces, including drain pans and duct work, is a source of contamination in the air stream. Conventional methods of addressing biofilms in these applications include maintenance cleaning of coils, duct work and drain pans, use of anticorrosion and antimicrobial coatings on system surfaces, and the exposure of system surfaces to C-band ultraviolet light to break down biofilms and kill pathogens.

Remediation of Biofilm Contamination in Household Applications

The household products industry is vitally concerned with disinfection of household surfaces, water and plumbing systems, and human hygienic needs. Difficulties associated with killing bacteria attached to these diverse surfaces are well known in this industrial sector and considerable research currently is directed at developing products which kill or remove biofilms.

An innovation in this sector is probiotic-based cleaning. Some versions of these products lay down layers of benign bacteria that successfully compete with pathogenic bacteria for resources on kitchen and bathroom surfaces. Other such products combine enzymes with probiotic bacteria to digest biofilms and dead pathogens. A leading example of this class of products is PIP produced by Chrisal Probiotics of the Netherlands.

The conventional approaches to treatment of biofilm discussed for both medical and industrial applications variously have been unproven, of limited effectiveness, time consuming, costly in cases where large surface areas are involved or surfaces require repeated treatment, and newer concepts have yet to demonstrate effectiveness and scalability to field applications. Hence, there remains an urgent need for more effective and less costly methods to treat biofilms. The present compositions and method offer the prospect of a new standalone approach to biofilm treatment with higher efficacy and lower cost, with additional potential for augmenting certain conventional treatments while reducing the costs of such treatments.

SUMMARY

Trehalose (a universal general stress response metabolite and an osmoprotectant) can play an important role in the formation and development of microbial biofilm and the specific interactions of trehalose with water can be considered to be one of the most important mechanisms of biofilm formation. The present compositions and methods have been conceived to target trehalose degradation as a key step in degrading biofilm.

In various embodiments of the compositions and methods, compounds that prevent, degrade, and/or inhibit the formation of biofilms, compositions comprising these compounds, devices exploiting these compounds, and methods of using the same are disclosed.

Because trehalose serves to manipulate hydrogen bonds among water molecules and bacterial cells in the process of forming the biofilm gel, the degradation of trehalose ultimately should result in degradation of the biofilm gel. A class of compounds that degrade trehalose with high specificity, thereby degrading the biofilm matrix gel is disclosed. Specifically, the naturally occurring enzyme trehalase will hydrolyze a molecule of trehalose into two molecules of glucose. The small amount of enzyme trehalase produced in the human body must be augmented with the administration of much larger amounts to treat in vivo biofilm-based infections. Various treatment formulations that incorporate trehalase enzymes and associated delivery mechanisms are detailed for specific types of infections; these include systemic and local treatment protocols. Additionally, trehalase-containing mixtures and associated processes are disclosed to degrade biofilms present on medical instruments and to mitigate biofilm fouling and biofilm-based biocorrosion for industrial applications. For degrading biofilms on medical equipment, trehalase-containing mixtures can be used in concert with other processes, such as ultrasound and ultrasound-assisted enzymatic activity to degrade biofilms. Biofilm prevention approaches comprise the use of trehalase enzymes in surface coatings.

Following is a lexicon of terms and phrases that more particularly define the compositions and methods and support the meaning of the claims:

Time-delayed release—in the context of the present compositions and methods, time-delayed release refers specifically to trehalase (or other compounds) release that occurs at a predetermined approximate time after the trehalase (and in some embodiments, other compounds) in pill, capsule, tablet or other form is ingested orally. Typically, for the present compositions and methods, the time delay means that the initial release of trehalase (or other compounds) will occur in the small intestine, to avoid degradation by naturally occurring proteolytic enzymes in the upper GI tract. Various pre-programmed temporal profiles for release in the small intestine are within the scope of the compositions and methods, such as, for example, linearly increasing or decreasing rates of release with time, or a constant rate of release.

Sustained release—in the context of the present compositions and methods, it refers to the release of trehalase (or other compounds) for applications external to the body. This is a continuous release of trehalase (or other compounds) that is not time-delayed, but is initiated at first opportunity for the purpose of continuous, ongoing exposure of medical device and industrial surfaces to treatment enzymes.

Sufficient for efficacy—pertains to treatment composition amounts and treatment exposure durations adequate to breakdown the gel structure of biofilm for its dispersal and further penetration by antimicrobial agents to treat the target infectious pathogens.

Trehalase—refers to any enzyme selected from the category of trehalase isoenzymes. There are two types of trehalase enzymes found in microorganisms: neutral trehalase (NT) typically found in the cytosol and acid trehalase (AT) found in the vacuoles of the cytosol, either of which type may find application in the present compositions and methods. Further, the number of candidate enzymes is large; as many as 541 model variants (isoenzymes) of trehalase can be found in the Protein Model Portal (http://www.proteinmodelportal.org), each exhibiting varying potencies in the hydrolysis of trehalose into glucose. The present compositions and methods anticipate a selection from among these isoenzymes that is optimized for the specific biofilm application. For example, the ability to sufficiently purify a given isoenzyme for internal bodily use may favor its selection for this purpose over another isoenzyme that exhibits higher enzymatic activity, but which would be relegated to industrial applications.

Digestive enzymes—are enzymes that break down polymeric macromolecules of ingested food into their smaller building blocks, in order to facilitate their absorption by the body. In the present icompositions and methods, treatment formulations comprising trehalase (or other compounds) are disclosed which should: a) avoid degradation by the digestive enzymes naturally occurring in the upper GI tract and b) be combined in time-delayed release form with digestive enzyme supplements to avoid degradation by proteolytic enzymes in such supplements.

Medical devices—comprise devices that are installed either temporarily or permanently in the body and medical instruments that may or may not contact the body, but at least contact tissue or bodily fluids. Examples of temporarily installed medical devices include catheters, endoscopes, and surgical devices. Permanent devices examples include devices such as orthopedic implants, stents, and surgical mesh. Examples of devices used external to the body include stethoscopes, dialysis machines, and blood and urinary analysis instruments. Each of the aforementioned devices exhibit surfaces that are vulnerable to biofilm formation and therefore can benefit from treatment by specific embodiments of the presently disclosed compositions and methods.

Antimicrobials—are substances that kill or inhibit the growth of microorganisms such as bacteria, fungi, or protozoans. Antimicrobials either kill microbes (microbiocidal) or prevent the growth of microbes (microbiostatic). Disinfectants are antimicrobial substances used on non-living objects or outside the body.

Other saccharidases (enzymes hydrolyzing saccharides)—include various di-, oligo-, and polysaccharidases.

Living organisms—pertains to the spectrum of living entities from microbes to animals and humans.

GI tract—refers to the gastrointestinal tract; the upper GI tract comprising the mouth, esophagus, stomach, and duodenum, and the lower GI tract comprising the small and large intestines.

Administering via the GI tract—relates to three main alternative treatment delivery methods: first is oral administration in which the treatment compounds are administered via the mouth; for the patients that may not be able to receive treatment by mouth, the second method available is by the naso-gastric tube; and a third method includes delivery by colonic irrigation.

Administering via systemic use—relates to administration of treatment compounds by percutaneous injection, intra-muscular injection, intra-venous injection, and venous catheter administration.

Other aspects, advantages, and features of the present disclosure will become apparent after review of the entire application, including the following sections: Brief Description of the Drawings, Detailed Description, and the Claims.

BRIEF DESCRIPTION OF THE DRAWINGS

FIG. 3 is a summary chart showing the biofilm produced by P. *Aeruginosa* PAO1 in accordance with a non-limiting example.

FIG. 4 is a summary chart of the biofilm produced by S. *Aureus* ATCC25923 in accordance with a non-limiting example.

FIG. 5 is another summary chart of the biofilm produced by S. *Aureus* ATCC25923 in accordance with a non-limiting example.

FIG. 6 is another summary chart of the biofilm produced by P. *Aeruginosa* PAO1 in accordance with a non-limiting example.

FIG. 7 is a summary chart for the results of the MIC determination with selected S. *Aureus* strains in accordance with a non-limiting example.

FIGS. 9A through 9C are charts for the results of the Trehalase testing on clinical isolates where the biomass has crystal violet staining in accordance with a non-limiting example.

FIGS. 10A through 10C are charts for the results of the Trehalase testing on clinical isolates for cell viability with resazurin staining in accordance with a non-limiting example.

FIGS. 11A through 11C are charts for the results showing the effectiveness of Trehalase added during biofilm growth on a catheter segment up to 24 hours in accordance with a non-limiting example.

FIGS. 12A through 12C are charts for the results of the Trehalase added after 24 hours biofilm growth on a catheter segment in accordance with a non-limiting example.

DETAILED DESCRIPTION

Figure 1A:
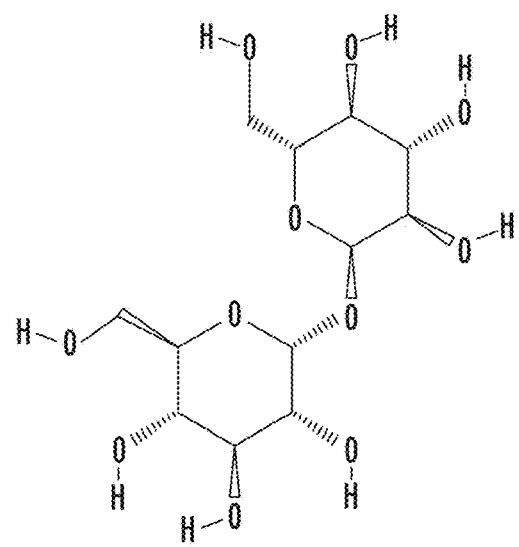
FIG. 1A is diagram of the chemical structure of the dissacharide trehalase.

Since any bacterial biofilm can be defined as a living dynamic structure with spatial and temporal heterogeneity for both components of microbial biofilm (the exopolymer gel matrix and the microcolonies of infectious microorganisms embedded in this gel matrix), the treatment approaches for biofilm-based chronic infections should be aimed simultaneously at both components of microbial biofilm: prevention of formation, inhibition of growth and degradation of biofilm gel matrix, and killing the infectious pathogens embedded in the biofilm gel matrix. In this context, trehalase should be included into existing approaches for prevention and treatment of microbial biofilms, being used in combination with existing natural and synthetic antimicrobials and anti-biofilm substances and methods of their use to increase their effectiveness. A review of recent patent literature summarizes citations under six categories of current treatment approaches: 1) antibiotics and small molecule inhibitors of new and established biofilms and biofilm-forming infectious pathogens, 2) quorum sensing and signaling molecules inhibitors, 3) surface coating substances for inhibition of biofilm formation on medical devices and equipment, 4) antibodies and vaccines for infectious biofilm treatment, 5) enzymes for degrading biofilms, and 6) bacteriophage treatment of infectious biofilms (Lynch A S and Abbanat D, "New antibiotic agents and approaches to treat biofilm-associated infections," Expert Opin. Ther. Patents, 2010; 20(10): 1373-1387).

All microorganisms in their natural environments encounter a multitude of stresses, including osmotic stress, oxidative stress, membrane and cell envelope stress, ribosomal stress, nutrient and oxygen limitations, temperature stress, and many other stresses as characteristics of various specific environmental conditions. Infectious pathogens encounter the same stresses in their environment—the internal milieu of their host (including human body). The infectious process of biofilm-based infections in the human body should be considered as a constant battle between infectious microorganism (for its adaptation, survival and proliferation in the milieu of a human body) and a host who uses all its natural defense mechanisms to kill the pathogen and eliminate it from the body, restore normal homeostasis, and repair damaged body tissues. The exposure to various stresses, impact bacterial susceptibility to a variety of antimicrobials through their initiation of stress responses that recruit various resistance determinants or promote physiological changes that compromise antimicrobial activity (Keith Poole, "Bacterial stress responses as determinants of antimicrobial resistance", J Antimicrob Chemother 2012; 67: 2069-2089). One of the most important survival mechanisms for any bacteria in any environment is the general stress response (ubiquitous in nature) triggered by various environmental stresses and their interactivities via genetic regulation. In general stress response, the increased production of trehalose (as a general stress response metabolite and an osmoprotectant) plays an important role in adaptation and survival of infectious pathogen in the host body, and plays an important role in antimicrobial resistance as well.

Trehalose is a disaccharide that is ubiquitous in the biosphere and present in almost all forms of life except mammals. In various bacteria and fungi, it is one of the most important storage carbohydrates, serving as a source of energy and as a carbon source for synthesis of cellular components; it can play a transport role and control certain metabolic pathways; it functions as a protectant for cell membranes and cell proteins against the adverse effects of various stresses, including the osmotic stress, heat, cold, desiccation, dehydration, deprivation of nutrients, oxidation, and anoxia (Elbein A D, "The metabolism of α,α-trehalose," Adv. Carbohyd. Chem. Biochem., 1974; 30: 227-256); (Crowe J, Crowe L, and Chapman D, "Preservation of membranes in anhydrobiotic organisms. The role of trehalose," Science, 1984; 223: 209-217); (Takayama K and Armstrong E L, "Isolation, characterization and function of 6-mycolyl-6'acetyltrehalose in the H37Rv strain of *Mycobacterium tuberculosis*," Biochemistry, 1976; 15: 441-446); (Christopher Askew, Adnane Sellam, Ellias Epp, Herve Hogues, Alaka Mullick, Andre Nantel, Malcolm Whiteway, "Transcriptional regulation of carbohydrate metabolism in the human pathogen *Candida albicans*", PLoS Pathogens 2009-10-01); (Joke Serneels, Helene Tournu, Patrick Van Dijck, "Tight control of trehalose content is required for efficient heat-induced cell elongation in *Candida albicans*", Journal of Biological Chemistry, 2012-10-26).

Trehalose may be partially responsible for the virulence and antimicrobial resistance properties in various opportunistic and pathogenic microorganisms, including those known to cause chronic infections with biofilm formation in the human body, including: *Pseudomonas* spp., *Bacillus* spp., *Staphylococci* spp., *Streptococci* spp, *Haemophilus influenza*, *Klebsiella pneumoniae*, *Proteus* spp., *Mycobacteria* spp., *Corynebacteria* spp., *Enterococci* spp., enteropathogenic *E. coli*, various human pathogenic yeasts and fungi (*Candida* spp., *Cryptococcus neoformans*, *Aspergillus* spp.). As demonstrated in some strains of *Candida albicans*, interference with the production of trehalose strongly reduces their virulence. Specifically, *C. albicans* mutants with deleted gene TSP2, which encodes trehalose-6-phosphate phosphatase, one of two enzymes involved in trehalose synthesis, exhibited diminished virulence in in vivo mouse model of systemic infection and, being grown within in vitro biofilm systems, displayed significantly less biofilm formation than selected non-mutant strains (Coeney T, Nailis H, Tournu H, Van Dick P, and Nelis H, "Biofilm Formation and Stress Response in *Candida Albicans* TSP2 Mutant," ASM Conference on *Candida* and Candidiasis, Edition 8, Denver, Colo.; Mar. 12-17, 2006). The in vivo studies in the pathobiology of *Cryptococcus neoformans*, identified the presence of a functioning trehalose pathway during experimental infection in the mouse and rabbit models and suggested its importance for *C. neoformans* survival in the host; using created null-mutants of the trehalose-6-phosphate (T6P) synthase (TPS1), trehalose-6-phosphate phosphatase (TPS2), and neutral trehalase (NTH1) genes, it was demonstrated that both TPS1 and TPS2 are required for high-temperature (37° C.) growth and glycolysis, but the block at TPS2 results in the apparent toxic accumulation of T6P, which makes the enzyme trehalose-6-phosphate phosphatase a fungicidal target (Elizabeth Wills Petzold, Uwe Himmelreich, Eleftherios Mylonakis, Thomas Rude, Dena Toffaletti, Gary M. Cox, Jackie L. Miller, and John R. Perfect, "Characterization and Regulation of the Trehalose Synthesis Pathway and Its Importance in the Pathogenicity of *Cryptococcus neoformans*", Infection and Immunity, October 2006, p. 5877-5887).

All microorganisms can synthesize trehalose intracellularly and/or take it from the environment using various synthesis and degradation pathways for trehalose metabolism. The specific use of these pathways by various microorganisms depends on their genetic program for trehalose utilization and availability of substrates for trehalose biosynthesis in their environment.

Many microorganisms, including human pathogenic bacteria and fungi, synthesize trehalose intracellularly mostly via pathways that utilize various nucleoside diphosphate glucose derivatives as glucosyl donors (ADP-D-glucose, CDP-D-glucose, GDP-D-glucose, TDP-D-glucose and UDP-D-glucose) and a-D-glucose-6-phosphate in a two-step reaction: in the first step—formation of intermediate metabolite trehalose 6-phosphate (T6P) by the action of enzyme trehalose-6-phosphate synthase (TPS), and in the second step—formation of final product trehalose (a,a-trehalose), by the action of enzyme trehalose-6-phosphate phosphatase (TPP) (Styrvold O B and Strom A R, "Synthesis, accumulation, and excretion of trehalose in osmotically stressed *Escherichia coli* K-12 strains: influence of amber suppressors and function of the periplasmic trehalase," J. Bacteriol, 1991; 173(3): 1187-1192. PMID: 1825082). It should be mentioned that some *mycobacteria*, such as *Mycobacterium smegmatis* and *Mycobacterium tuberculosis*, possessing unusual trehalose-6-phosphate synthases, are capable of utilizing all five nucleoside diphosphate glucose derivatives as glucosyl donors (Lapp D, Patterson B W, Elbein A D, "Properties of a trehalose phosphate synthetase from *Mycobacterium smegmatis*. Activation of the enzyme by polynucleotides and other polyanions," J. Biol. Chem., 1971; 246 (14): 4567-4579).

Also, many microorganisms, can synthesize trehalose directly from disaccharide maltose (degradation product of glycogen and starch) independently of the presence of phosphate compounds trehalose-6-phosphate and glucose-6-phosphate. This pathway involves the intramolecular rearrangement of maltose (glucosyl-alpha1,4-glucopyranoside) to convert the 1,4-linkage into the 1,1-linkage of trehalose by the action of enzyme trehalose synthase (TS), forming free trehalose (a,a-trehalose) as the initial product. It is postulated that in *Corynebacterium glutamicum* this pathway may work in the opposite direction, compensating for the absence of a trehalase enzyme, by converting excess trehalose back into maltose, for reuse as a carbon source (De Smet K A, Weston A, Brown I N, Young D B, Robertson B D, "Three pathways for trehalose biosynthesis in *mycobacteria*," Microbiology, 2000; 146 (Pt 1): 199-208. PMID: 10658666); (Wolf A, Cramer R, Morbach S, "Three pathways for trehalose metabolism in *Corynebacterium glutamicum* ATCC 13032 and their significance in response to osmotic stress," Mol Microbial, 2003; 49(4): 1119-1134. PMID: 12890033).

In an additional pathway, trehalose can be formed from polysaccharides (such as glycogen or starch) in multi-step process by the action of several enzymes: in the first step—the enzyme isoamylase hydrolyzes the α-1,6-glucosidic linkage in glycogen or the a-1,4-glucosidic linkages in other polysaccharides (such as starch from plants), to produce a maltodextrin (oligosaccharide); in the next step—the enzyme maltoolgosyl-trehalose synthase (MTS) converts maltodextrin to maltooligosyl-trehalose by forming an α,α-1,1-glucosidic linkage via intermolecular transglucosylation; and in the third step—the enzyme maltooligosyl-trehalose trehalohydrolase (MTTH) hydrolyzes the product, forming free trehalose (a,a-trehalose) and a maltodextrin which becomes shorter by two glucosyl residues. In *Corynebacterium glutamicum*, which possess three different pathways for trehalose biosynthesis, this is the main route for trehalose biosynthesis (Maruta K, Mitsuzumi H, Nakada T, Kubota M, Chaen H, Fukuda S, Sugumoto T, Kurimoto M, "Cloning and sequencing of a cluster of genes encoding novel enzymes of trehalose biosynthesis from thermophilic archaebacterium *Sulfolobus acidocaldarius*," Biochim Biophys Acta, 1996; 129 (3): 177-181. PMID: 8980629).

For degradation of trehalose, various microorganisms, including human pathogenic bacteria and fungi, can utilize several alternative pathways. Unmodified trehalose (a, a-trehalose) may be degraded by a hydrolyzing enzyme trehalase (a,a-trehalohydrolase), yielding two β-D-glucose molecules, or it may be split by the action of the enzyme trehalose phosphorylase (TP), yielding β-D-glucose-6-phosphate as the end product. Trehalose phosphorylase (TP), can also catalyze the reversible synthesis and degradation of trehalose from/to a β-D-glucose-1-phosphate and β-D-glucose, or α-D-glucose-1-phosphate and α-D-glucose. Phosphorylated form, trehalose-6-phosphate, can be either hydrolyzed by trehalose-6-phosphate hydrolase, yielding β-D-glucose and β-D-glucose-6-phosphate, or degraded by trehalose-6-phosphate phosphorylase, yielding β-D-glucose-1-phosphate and β-D-glucose-6-phosphate. All end products of the degradation pathways can be metabolized via glycolysis. All end products of trehalose degradation pathways can be metabolized via glycolysis. (Helfert C, Gotsche S, Dahl M K, "Cleavage of trehalose-phosphate in *Bacillus subtilis* is catalyzed by a phospho-alpha-(1-1)-glucosidase encoded by the TreA gene," Mol Microbiol, 1995; 16(1): 111-120. PMID: 7651129); (Levander F, Andersson U, Radstrom P, "Physiological role of beta-phosphoglucomutase in *Lactococcus lactis*," Appl Environ Microbiol, 2001; 67(10): 4546-4553. PMID: 11571154).

For survival in the live environment of a human body, the pathogenic microorganisms must continuously adapt to temporal and spatial fluctuations in osmolarity of body fluids. In osmoadaptation, bacteria constitutively use the universal mechanism of uptake and release of osmotically active compounds (osmolytes). Bacteria adapt to the conditions of increased external osmolarity by importing charged ions from the environment, and importing or synthesizing compatible solutes. Upon a shift to a low-osmolarity media, the excretion of osmolytes is required to restore normal turgor and prevent the cells from bursting. The pathways for import and efflux of compatible solutes include PTS system, ABC transporters, mechanosensitive channels, and porins (Berner C M, Besnard M, Ajouz B, Coulombe A, and Ghazi A, "Multiple mechanosensitive ion channels from *Escherichia coli*, activated at different thresholds of applied pressure," J. Membr. Biol., 1996; 151: 175-187); (Bremer R and Kraemer R, "Coping with osmotic challenges: osmoregulation through accumulation and release of compatible solutes in bacteria," pp. 79-97. In G. Storz and R. Hengge-Aronis (ed.), Bacterial stress responses. 2000; ASM Press, Washington, D.C.); (Chang G, Spencer R, Lee A T, Barclay M T, and Rees D C, "Structure of the MscL homolog from *Mycobacterium tuberculosis*: a gated mechanosensitive ion channel," Science, 1998; 282: 2220-2225); (Morbach S and Kraemer R, "Body shaping under water stress: osmosensing and osmoregulation of solute transport in bacteria," ChemBioChem, 2002; 3: 384-397).

Compatible solutes are small, zwitterionic, highly soluble organic molecules, which include diverse substances, such as amino acids (proline,glutamate), amino acid derivatives (glycine betaine, ectoine), and sugars (trehalose and sucrose), that are thought to stabilize proteins and lead to the hydration of the cell (Steator R D and Hill C, "Bacterial osmoadaptation: the role of osmolytes in bacterial stress and virulence," FEMS Mocrobiol. Rev., 2002; 26: 49-71). Various bacteria may prefer different osmolytes taken from the environment, but all of them constitutively utilize trehalose (taken from the environment or synthesized intracellularly) as a universal osmoprotectant. For example, *E. coli* and *Vibrio Cholerae* in human GI tract prefer glycine betaine, but its synthesis relies on an external supply of proline, betaines, or choline which may not be readily available in the environment or significantly reduced in the deeper layers of microbial biofilm. When these compounds are not available, a microbial cell can achieve a moderate level of osmotic tolerance by accumulation of glutamate and trehalose (Styrvold O B, Strom A R, "Synthesis, accumulation, and excretion of trehalose in osmotically stressed *Escherichia coli* K-12 strains: influence of amber suppressors and function of periplasmic trehalase," J Bacteriol, 1991; 173 (3): 1187-1192. PMID: 1825082); (Kapfhammer D, Karatan E, Pflughoeft K J, and Watnik P I, "Role for Glycine Betaine Transport in *Vibrio cholera* Osmoadaptation and Biofilm Formation within Microbial Communities," Applied and Environmental Microbiology, July 2005: 3840-3847).

As demonstrated in laboratory-grown bacteria, the first adaptive response to osmotic stress comprises both the increased uptake rate and the amount of cytosolic potassium, followed by the accumulation of glutamate and synthesis of trehalose (Dinnbier U, Limpinsel E, Schmid R, and Bakker E P, "Transient accumulation of potassium glutamate and its replacement by trehalose during adaptation of growing cells of *Escherichia coli* K-12 to elevated sodium chloride concentrations," Arch. Microbiol., 1988; 150: 348-357); (McLaggan D, Naprstek J, Buurman E T, and Epstein W, "Interdependence of $K^+$ and glutamate accumulation during osmotic adaptation of *Escherichia coli*," J. Biol. Chem., 1994; 269: 1911-1917); (Strom A R and Kaasen I, "Trehalose metabolism in *Escherichia coli*: stress protection and stress regulation of gene expression," Mol. Microbiol., 1993; 8: 205-210). The time-dependent (10 to 60 minutes) alterations in the proteome of *E. coli* (grown under aerobic conditions) in response to osmotic stress, demonstrated upregulated genes for synthesis of both trehalose and cytosolic trehalase (trehalose-degrading enzyme with regulatory properties) in the middle phase (10 to 30 minutes) and in the long phase (30 to 60 minutes) of bacterial adaptation to hyperosmotic stress, with the trehalase synthesis genes (TreF) upregulated in the early phase of adaptation (0 to 10 minutes) (Weber A, Kögl S A, and Jung K, "Time-Dependent Proteome Alterations under Osmotic Stress during Aerobic and Anaerobic Growth in *Escherichia coli*," Journal of Bacteriology, October 2006: 7165-7175. doi: 10.1128/JB.00508-06).

Trehalose is a stable dissaccharide with glycosidic bond [O-α-D-Glucopyranosyl-(1-1)-α-D-glucopyranoside] formed from a condensation between the hydroxyl groups of the anomeric carbons of two molecules of glucose, preventing them from interacting with other molecules and thereby rendering trehalose among the most chemically inert sugars (Birch G G, "Trehaloses," Adv. Carbohydr. Chem. Biochem., 1963; 18: 201-225); (Elbein A D, "The metabolism of alpha, alpha-trehalose," Adv. Carbohydr. Chem. Biochem., 1974; 30: 227-256). The flexible glycosidic bond, together with the absence of internal hydrogen bonds, yields a supple molecule, but this glycosidic bond does not break easily: the 1 kcal/mol linkage is highly resilient, enabling the trehalose molecule to withstand a wide range of temperature and pH conditions (Pava C L and Panek A D, "Biotechnological applications of the disaccharide trehalose," Biotechnol. Annu. Rev., 1996; 2: 293-314). Because of the unusual glycosidic bond between the anomeric carbons (1-1), there are no more accessible carbons for further polymerization, so that trehalose exists only as a disaccharide, being rather distributed as disaccharide molecules in the gel-like matrix of biofilm, influencing its density via interaction between trehalose and water molecules. Intermolecular hydrogen bonds (H bonds), the strongest of intermolecular forces, are central to trehalose interaction with water. Specifically, such bonds modify the structure of water surrounding trehalose molecules and account for the self-aggregation phenomena of trehalose molecules observed in molecular dynamic simulations and supported by experimental studies.

Figure 1B:
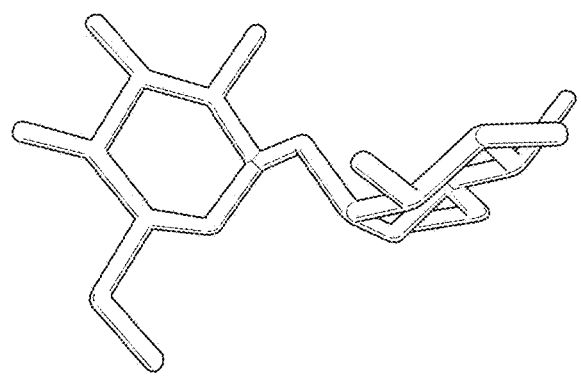
FIG. 1B is a pictorial diagram of the backbone structure of trehalase.
Figure 2A:
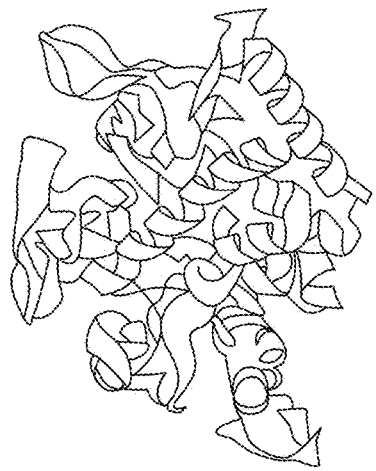
FIG. 2A is a ribbon model pictorial diagram of an enzyme of trehalase derived from *Sacharomyces cerevisiae*.
Figure 2B:
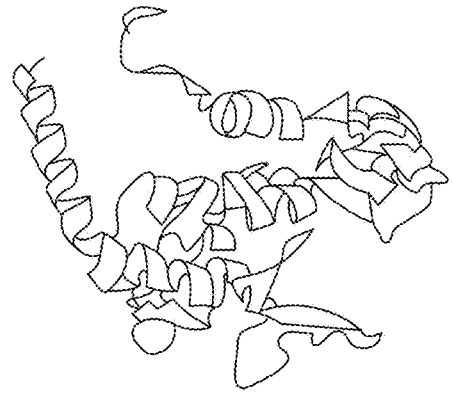
FIG. 2B is a ribbon model pictorial diagram of an enzyme of trehalase derived from *Penicillium marneffei*.
Figure 2C:
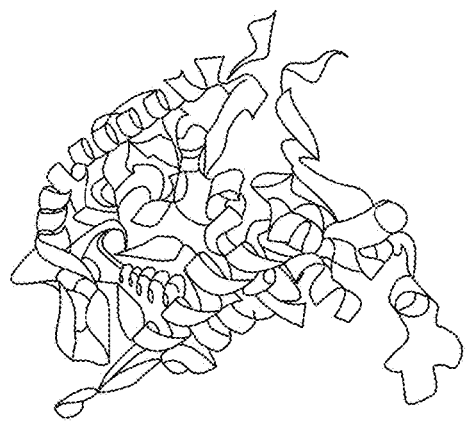
FIG. 2C is a ribbon model pictorial diagram of an enzyme of trehalase derived from *Homo sapiens*.
Figure 2D:
FIG. 2D is a ribbon model pictorial diagram of an enzyme of trehalase derived from *Candida albicans*.

The chemical structure of trehalose is depicted in FIG. 1*a* indicating an alpha-linked disaccharide formed by an α,α-1,1-glucosidic bond between two α-glucose units. The backbone structure of this enzyme is shown in FIG. 1*b* depicting the two planes established by the glucose units.

Trehalose has a unique ability to capture water through extensive solvation. Water molecules are arranged in a solvation complex around trehalose molecules, with water associating with trehalose functional groups through H bond formation; at infinite dilution, the solvation number approaches 15 (the highest among all disaccharides). Trehalose is able to restructure water even at minimum aqueous concentrations, supporting the gelation phenomena in these conditions. With respect to water restructuring behavior, trehalose enhances the hydrogen bonding between water molecules by approximately 2%. This is sufficient to destructure the pure water tetrahedral network in conformity with a restructuring imposed by trehalose clusters. Stronger, more linear, and better optimized H bonds are formed between water molecules, while weaker bonds are relegated to trehalose-water interactions (Sapir L and Harries D, "Linking Trehalose Self-Association with Binary Aqueous Solution Equation of State," J. Phys. Chem. B, 2011; 115: 624-634).

Trehalose self-associates in aqueous solutions in a concentration dependent manner to form clusters of increasing size, until finally forming percolating, infinitely connected, clustering networks (at concentrations of 1.75 M and higher), affecting the dynamic properties of the solution. The lack of intramolecular hydrogen bonds in trehalose, compared with other disaccharides (sucrose, maltose, isomaltose), accounts for its higher tendency to aggregate, thereby already affecting the dynamic properties of water at lower trehalose concentrations (Lebret A, Bordat P, Affouard F, Descamps M, Migliardo F J, Phys. Chem. B, 2005; 109: 11046); (Lebret A, Affouard F, Bordat P, Hedoux A, Guinet Y, and Descamps M, Chem. Phys., 2008; 345:267); (Peric-Hassler L, Hansen H S, Baron R, and Hunenberger P H, "Conformational properties of glucose-based disaccharides investigated using molecular dynamics simulations with local elevation umbrella sampling," Carbohydr. Res., 2010; 345: 1781.)

In a ternary mixture of protein (lysozyme), sugar, and water, at a moderate concentration of 0.5 M, trehalose can cluster around the protein, thereby trapping a thin layer of water molecules with modified solvation properties, playing the role of a "dynamic reducer" for solvent water molecules in the hydration shell around the protein. A remarkable conformational rigidity of the trehalose molecule due to anisotropic hydration (very little hydration adjacent to the glycosidic oxygen of trehalose), provides stable interactions with hydrogen-bonded water molecules; trehalose makes an average of 2.8 long-lived hydrogen bonds per each step of molecular dynamic simulation compared with the average of 2.1 for the other sugars (Lins R D, Pereira C S, and Hunenberger P H, "Protein-Trehalose Interactions in Aqueous Solution," Proteins, 2004; 55: 177); (Choi Y, Cho K W, Jeong K, and Jung S, "Molecular dynamic simulations of trehalose as a 'dynamic reducer' for solvent water molecules in the hydration shell," Carbohydr Res., Jun. 12, 2006; 341(8): 1020-1028).

In a simulated ternary mixture of lipid membranes, composed of DPPC (dipalmitoylphosphatidylcholine), with aqueous solution of trehalose, the trehalose molecules cluster near membrane interfaces, forming hydrogen bonds both between trehalose molecules and with the lipid headgroups (Pereira C S, Hunenberger P H, "The effect of trehalose on a phospholipid membrane under mechanical stress," Biophys. J., 2008; 95: 3525); (Sum A K, Faller R, and de Pablo J J, "Molecular simulation study of phospholipid bilayers and insights of the interactions with disaccharides," Biophys. J., 2003; 85: 2830). Trehalose may compete with water binding to both carbonyls and phosphates in cell membranes, forming the OH bridges that are stronger than the H-bonds of water with those groups, and the displacement of water is compensated with the insertion of sugar. Trehalose, a dimer of glucose with the ability to form at least 10 hydrogen bonds, inserts in a lipid interface nearly normal to the lipid bilayer plane and can decrease water activity in the cell membrane up to 70% at a concentration of trehalose as low as 0.1 mM. The insertion of trehalose, replacing water simultaneously at the carbonyls and the phosphates, does not cause the surface defects in the cell membrane with respect to hydrated lipids (Pereira C S and Hunenberger P H, "The effect of trehalose on a phospholipid membrane under mechanical stress," Biophys. J., 2008; 95:3525); (Sum A K, Faller R, and de Pablo J J, "Molecular simulation study of phospholipid bilayers and insights of the interactions with disaccharides," Biophys. J., 2003; 85: 2830); (Villareal M, Diaz S B, Disalvo E A, Montich G, Langmuir, 2004; 20: 7844). We hypothesize that disaccharide trehalose, being inserted into the phospholipid bilayer(s) of bacterial cell membrane(s) for protection of their integrity, can affect the fluidity of the cell membranes (via its specific interactions with water, carbonyls and phosphates), and cause conformational changes in trans-membrane proteins (including ion channels, efflux pumps and porins), resulting in changes of their functional properties.

As a result of water displacement, trehalose may affect the cell surface potential and hence microbial cell aggregation and attachment to surfaces. There can be at least two mechanisms for these phenomena. First, the magnitude of cell surface potential can be modulated by trehalose displacement of water in its attachment to cell membrane phospholipids and carbonyl compounds. Second, this same displacement of water (in a non-uniform manner) can lead to heterogeneity of surface potential, also imparting the adhesion properties of microorganism. (Poortinga A T, Bos R, Norde W, and Busscher H J, "Electric double layer interactions in bacterial adhesion to surfaces," Surface Science Reports, 2002; 47: 1-31); (Disalvo E A, Lairion F, Martini F, Almaleck H, Diaz S, and Gordillo G, "Water in Biological Membranes at Interfaces: Does it Play a Functional Role?," An. Asoc. Quim. Argent., 2004; V. 92 n. 4-6 Buenos Aires ago./dic.).

Trehalose and Biofilm Formation

Based on the unique properties of trehalose as a universal general stress response metabolite and an osmoprotectant, and the specific features of its interactions with water (which comprises up to 95% of biofilm matrix), trehalose can be one of the most important components of microbial biofilm, and its specific interactions with water can be considered to be one of the most important mechanisms of biofilm formation.

Since the formation of microbial biofilm can be seen as a continuous process of adaptation of a microorganism to its environment, trehalose and its interactions with water can play an important role in all stages of microbial biofilm development (the early stage of initial biofilm formation, maturation of the biofilm, and dispersal of the biofilm).

From the first moment, when a microorganism enters the human body in a planktonic form, it is subjected to various stresses (first of all, osmotic stress) and undergoes the general stress response with the production of trehalose, which in its initial interactions with water begins the process of microbial biofilm formation. In this initial stage, trehalose facilitates adhesion of planktonic bacteria to surfaces by various means: as a result of its interaction with water and the lipid headgroups at the cell membrane interfaces, it decreases the microbial cell surface potential and enhances the bacterial cell aggregation, initial adsorption and attachment to the surfaces, both biotic and abiotic. Also, trehalose favors the bacterial cell aggregation and attachment to various surfaces by forming a hydration layer with modified solvation properties around the bacterial cell and reducing the dynamic properties of water in this layer (and up to the 3-rd and 4-th hydration layers), thus slowing down the bacterial cell movement. In addition, trehalose self-associates in aqueous solution in a concentration dependent manner to form clustering networks, affecting the dynamic properties of the solution. Through extensive solvation, trehalose has a potent ability to restructure water in the solution and enhance the hydrogen bonding between water molecules, thus contributing to the gelation phenomena and the biofilm formation.

During the next stage of the biofilm development (the formation of bacterial colonies and the maturation of biofilm), the bacteria will continuously produce trehalose as a general stress response metabolite and an osmoprotectant in response to constantly varying environmental conditions, such as increased cell density, nutrients limitations, and waste products accumulation in the biofilm. Then, the continuous trehalose-water interactions, with attraction of new water molecules and further restructuring of water, will result in formation of new layers of the biofilm and gradually increased biofilm volume. During this stage, bacteria will release into the biofilm matrix various extracellular substances, including specific proteins (adhesins, matrix interacting factors), compatible solutes, signaling molecules, metabolic end- or by-products, such as polysaccharides, lipids, phospholipids, and the detritus from aging and lysed cells, which will contribute to the formation of the tertiary structure of the biofilm, stabilization of the biofilm architecture, thickening of the biofilm matrix, and increased density of the biofilm.

During the late stage (the dispersal stage of microbial biofilm), as the biofilm ages, the amount of trehalose in the superficial layers of the biofilm will gradually decrease due to higher accumulation of trehalose in the deeper layers adjacent to the microbial cells, so that the trehalose restructuring effect on water, the strengthening effect on the hydrogen bonds between water molecules, and the aggregation forces between the microbial cells will gradually diminish and favor the sloughing off of the superficial layers of the biofilm, containing the pathogenic microorganisms that already have been exposed to the host defense factors and various antimicrobial substances (if used). These microorganisms, disseminating from the sloughing off superficial layers of the "parenting biofilm", will be covered by the thin layer of their "parenting" matrix gel, or just covered by superficial water layer(s) formed by their own trehalose for protection from osmotic stress during their move through the body tissues and fluids. These disseminating microorganisms may express higher resistance to the host defense factors and antimicrobials (due to their previous exposure to higher concentrations of antimicrobials in the superficial layers of "parenting biofilm") and potentially increased virulence, so that the newly formed disseminated biofilm sites, containing these pathogenic microorganisms, will contribute to further increase in antimicrobial resistance and virulence in the initial microorganisms forming the "initial biofilms".

At any stage of the biofilm development, the microorganisms embedded in the biofilm matrix will respond to any environmental assault on the biofilm, including the use of various harmful substances (i.e. antimicrobials, disinfectants, and various other anti-biofilm compounds) by additional production of trehalose as a general stress response metabolite and an osmoprotectant, that will result in further increase in the biofilm gel matrix volume and density, thus preventing the penetration of harmful substances into the biofilm and protecting the microorganisms from killing.

Trehalose was detected along with other sugars, di-, oligo-, and polysaccharides in the laboratory-grown microbial biofilms, in the research studies mostly aimed at either evaluating the effect of various nutrients on microbial biofilm formation, or analyzing the content of the biofilm exopolymer matrix.

For example, trehalose was detected in a small amount (3%), along with glycerol (5%), mannitol (18%), and glucose (74%), in the monosaccharide-polyol fraction of the aerial-grown hyphae of the *Aspergillus fumigatus* biofilm; all hexoses and polyols were found intracellularly in the same proportion as extracellularly (Beauvais A, Schmidt C, Guadagnini S, Roux P, Perret E, Henry C, Paris S, Mallet A, Prevost M, and Latge J P, "An extracellular matrix glues together the aerial-grown hyphae of *Aspergillus* fumigates," Cellular Microbiology, 2007; 9(6): 1588-1600). In another example, biofilm development on stainless steel by *Listeria monocytogenes* (the most common biofilm-producing pathogen in the food industry), was enhanced by the presence of mannose or trehalose as nutrients in the growth media, with trehalose being superior to mannose in constant biofilm production during 12 days of incubation at 21 degrees C. (Kim K Y and Frank J F, "Effect of nutrients on biofilm formation by *Listeria monocytogenes* on stainless steel," Journal of food protection, 1995; 58(1): 24-28). In another study, the formation of a structurally and metabolically distinctive biofilm by *Streptococcus mutans* (the most common pathogen in dental biofilms), was enhanced by the combination of sucrose and starch, compared with sucrose alone, in the presence of surface-adsorbed salivary a-amylase and bacterial glucosyltransferases, with upregulation of genes associated with maltose uptake/transport and fermentation/glycolysis (Klein M I, DeBaz L, Agidi S, Lee H, Xie G, Lin A H, Hamaker B R, Lemos J A, and Koo H, "Dynamics of *Streptococcus mutans* Transcriptome in Response to Starch and Sucrose during Biofilm Development," PLoS ONE, 2010; 5(10): 1-13). In the next study, the yeasts from hydrocarbon-polluted alpine habitats (*Cryptococcus terreus*—strain PB4, and *Rhodotorula creatinivora*—strains PB7 and PB12) synthesized and accumulated glycogen (both acid- and alkali-soluble) and trehalose during growth in culture media, containing either glucose or phenol as a sole carbon and energy source, with higher biofilm formation by both strains of *Rhodotorula creatinivora* (Krallish I, Gonta S, Savenkova L, Bergauer P, and Margesin R, "Phenol degradation by immobilized cold-adapted yeast strains of *Cryptococcus terreus* and *Rhodotorula creatinivora*," Extremophiles, 2006; 10(5): 441-449).

In contrast to the previous results, the laboratory-grown wild type *Enterococcus faecalis* formed strong biofilm in the presence of maltose or glucose in the growth media, and formed very little amount of biofilm in medium containing trehalose (Creti R, Koch S, Fabretti F, Baldassarri L, and Johannes H, "Enterococcal colonization of the gastro-intestinal tract: role of biofilm and environmental oligosaccharides," BMC Microbiology, 2006; 6: 660-668).

Since trehalose is the most abundant disaccharide in yeasts and fungi, the biofilm matrix of any biofilm-based yeast or fungal infections, and/or multispecies biofilms which include yeasts and/or fungi, can be more resistant to penetration by antimicrobials.

Enzyme Trehalase ($\alpha,\alpha$-Trehalase; $\alpha,\alpha$-Trehalose-1-C-Glucohydrolase, EC 3.2.1.28)

Enzyme trehalase (a,a-trehalase), highly specific for the non-reducing disaccharide trehalose, directly degrades trehalose into two molecules of glucose on hydrolysis, being this the only trehalose degradation pathway reported up to today. Trehalase phylogeny unveiled three major branches comprising those from bacteria, plant and animals, and those from fungal origin. Crystallographic study of bacterial trehalase indicated that this enzyme's structures are highly conserved in spite of the marked differences found at the sequence level, suggesting a bacterial origin for the trehalases in contrast to an eukaryotic origin, as previously proposed (Barraza A, Sanchez F. "Trehalases: A neglected carbon metabolism regulator?", Plant Signal Behva 2013; 8: e24778). Trehalose degradation by trehalase appears to be important, perhaps essential, in the life functions of various lower organisms, including yeasts, fungi, bacteria, insects, and invertebrates (Nwaka S and Holzer H, "Molecular biology of trehalose and trehalases in the yeast, *Saccharomyces cerevisiae*," Prog. Nucleic Acid Res. Mol. Biol., 1998; 58: 197-237). Enzyme trehalase also has been reported to be present in many macroorganisms (including mammals—animals and humans) and vascular plants, but the functions and properties of this enzyme were not fully elucidated (Elbein A D, "The metabolism of $\alpha,\alpha$-trehalose," Adv. Carbohyd. Chem. Biochem., 1974; 30: 227-256); (Elbein A D, Pan Y T, Pastuszak I, and Carroll D, "New insights on trehalose: a multifunctional molecule," Glycobiology, 2003; Vol. 13, No 4: 17R-27R.).

As many as 541 model variants of trehalase can be found in the Protein Model Portal (http://www.proteinmodelportal.org/). A few of these models corresponding to different enzyme variants (isoenzymes) are shown in FIGS. 2a through 2d.

In lower forms of life (yeasts, fungi, bacteria), there are two main types of trehalase enzyme: neutral trehalase (NTH) and acid trehalase (ATH), which are encoded by two different genes. Most of the trehalase activity in these microorganisms, comes from the neutral trehalase, located in the cytosol, with the pH optimum of about 7, highly specific for trehalose as the substrate, and inactive on cellobiose, maltose, lactose, sucrose, raffinose, and mellibiose; this enzyme has also a specific regulatory function (App H and Holzer H, "Purification and characterization of neutral trehalase from the yeast ABYS1 mutant," J. Biol. Chem., 1989; 264: 17583-17588). The acid or vacuolar trehalase has a pH optimum of 4.5 and is also very specific for trehalose as the substrate, showing no activity with cellobiose, maltose, lactose, sucrose, and mellibiose; this enzyme acts in the periplasmic space where it binds exogenous trehalose to internalize it for further cleavage it in the vacuoles to produce free glucose (Mittenbuhler K and Holzer H, "Purification and characterization of acid trehalases from the yeast SUC2 mutant," J. Biol. Chem., 1988; 263: 8537-8543); (Stambuk B U, de Araujo P S, Panek A D, and Serrano R, "Kinetics and energetics of trehalose transport in *Saccharomyces cerevisiae*," Eur. J. Biochem., 1996; 237: 876-881).

The activities of both trehalases (NTH and ATH) are low in yeast cells growing exponentially, but high during stationary phase growth after glucose has been depleted (Winkler K, Kienle I, Burgert M, Wagner J C, and Holzer H, "Metabolic regulation of the trehalose content of vegetative yeast," FEBS Lett., 1991; 291: 262-272). ATH1 deletion mutant of the yeast *S. cerevisiae* cannot grow in the medium with trehalose as the carbon source, but a *Candida* utils mutant strain is able to utilize extracellular trehalose as carbon source despite of the lack of ATH activity. Various bacteria, such as *E. coli*, have trehalases that also may supply exogenous trehalose and glucose via the phosphotransferrase system (PTS) (Horlacher R, Uhland K, Klein W, Erhmann M, and Boos W, "Characterization of a cytoplasmic trehalase of *Escherichia coli*," J. Bacteriol., 1996; 178: 625-627).

In the plant kingdom, enzyme trehalase is ubiquitous, being involved in carbon metabolism in both lower and higher plants. Although sugar trehalose is rare in higher (vascular) plants, it has been demonstrated that trehalase in these plants could take a part in the degradation of trehalose derived from the plant-associated bacteria in symbiotic interactions; it has been also suggested that trehalase in higher plants could play additional role in the defense against parasites and other pathogenic organisms (in plant-pathogen interactions) (Muller J, Wiemken A, and Aeschbacher R, "Trehalose metabolism in sugar sensing and plant development," Plant Sci., 1999; 147: 37-47); (Muller J, Aeschbacher R A, Wingler A, Boller T, and Wiemken A, "Trehalose and trehalase in *Arabidopsis*," Plant Physiol., 2001; 125: 1086-1093).

Though disaccharide trehalose is not produced in mammals, the enzyme trehalase exists in mammals (including humans) in the kidney brush border membranes and in the intestinal villi membranes; the role of trehalase in kidney is still not clear, but in the intestine its function is to hydrolyze ingested trehalose (Dahlqvist A, "Assay of intestinal disaccharidases," Anal. Biochem., 1968; 22: 99-107); (Ruf J, Wacker H, James P, Maffia M, Seiler P, Galand G, Kiekebusch A, Semenza G, and Mantei N, "Rabbit small intestine trehalase. Purification, cDNA cloning, expression and verification of GPI-anchoring," J. Biol. Chem, 1990; 265: 15034-15040); (Yonemaya Y and Lever J E, "Apical trehalase expression associated with cell patterning after inducer treatment of LLC-PK monolayers," J. Cell. Physiol., 1987; 131: 330-341). Only one type of trehalse (α,α-trehalase, highly specific enzyme for direct degradation of trehalose into two molecules of glucose) is present in humans. Trehalase produced by the glands of Lieberkuhni in the small intestine is a constituent of the intestinal juice along with other specific saccharidases, such as maltase, sucrase-isomaltase complex, and Beta-glycosidase-lactase (Mayes P A, "Carbohydrates of physiologic significance," In: Harper's Biochemistry, 25th ed, 2000, pp. 149-159, Appleton & Lange, Stamford, Conn.); (Rodwell V W and Kennelly P J, "Enzymes: General Properties; Enzymes: Kinetics," In: Harper's Biochemistry, 25th ed, 2000, pp. 74-102, Appleton & Lange, Stamford, Conn.). As with all other disaccharidases, trehalase remains attached to the brush border of the enterocyte in the intestinal lumen while the catalytic domain is free to react with the substrate. There is little free trehalase activity in the intestinal lumen; most activity is associated with small "knobs" on the brush border of the intestinal epithelial cells. A small fraction (approximately 0.5%) may be absorbed by passive diffusion, as shown for other disaccharides, in patients with trehalase deficiency (van Elburg R M, Uil J J, Kokke F T M, Mulder A M, van dr Broek W G M, Mulder C J J, and Heymans "Repeatability of the sugar-absorption test, using lactulose and mannitol, for measuring intestinal permeability for sugars," J. Pediatr. Gastroenterol. Nutr., 1995; 20: 184-188). Trehalase activity have been found also in the renal cortex, plasma, urine, liver and bile, although function of the enzyme in these locations is not clear yet; it is likely that trehalase in the urine and bile can be incidental to its presence in the kidney and liver (Eze L C, "Plasma trehalase activity and diabetes mellitus," Biochem Gen., 1989; 27: 487-495). A complete cDNA clone encoding human trehalase (a protein of 583 amino acids with calculated molecular weight of 66 595 kDa), a glycoprotein of brush-border membranes, has been isolated from a human kidney library; the deduced amino acid sequence of the human trehalase enzyme showed similarity to sequences of the enzyme trehalase from rabbit (81%), silk worm, *Tenebrio molitor* (43%), *Escherichia coil* (33%); human trehalase also resembled yeast acidic trehalase—ATH (25% identity) and neutral trehalase—NTH (26.5% identity); by homology with mammalian trehalase from other species, human enzyme is an ectoenzyme whose hydrophobic region at the carboxyl terminus is linked to the plasma membrane by GPI anchor (Reiko Ishihara, Shigeru Taketani, Misa Sasai-Takedatsu, Minoru Kino, Rikio Tokunaga, Yohnosuke Lobayashi, "Molecular cloning, sequencing and expression of cDNA encoding human trehalase", Cene 202 (1997) 69-74). The research data showed that mammalian trehalase is encoded by a single gene and is probably expressed as one form in various tissues (Ruf, J., et. al., 1990, "Rabbit small intestinal trehalase: purification, cDNA cloning, expression, and verification of glucosylphosphatidylinositol anchoring", J. Biol. Chem. 265, 15034-15039; Reiko Ishihara, et. al., "Molecular cloning, sequencing and expression of cDNA encoding human trehalase", Gene 202 (1997) 69-74.

Biochemical Properties of the Human Enzyme α,α-Trehalase Include:

high specificity for the substrate (disaccharide trehalose—a,a-trehalose)

method of activation—direct contact with the substrate (trehalose)

optimal conditions for activity—in the range of pH between 5.0 and 7.0 (similar to the other disaccharidases)

end product of action—2 molecules of D-glucose heat sensitivity—as a glycosylated protein is probably similar to the other disaccharidases catalytic efficiency—high due to the high specificity for the substrate trehalose coenzymes or metal ions for activity—not needed co-variants of enzyme—unknown The main function of human α,α-trehalase is to hydrolyze ingested disaccharide trehalose into glucose. Trehalase deficiency is a known metabolic condition in humans, when the body is not able to degrade disaccharide trehalose into two molecules of glucose and digest it. People with enzyme trehalase deficiency experience vomiting, abdominal discomfort and diarrhea after eating mushrooms (rich in trehalose) of any other food containing trehalose. Trehalase enzyme deficiency in most cases appear to be inherited in an autosomal recessive manner (Kleinman R E, Goulet O, Mieli-Vergani G, Sherman P M, In: Walker's Pediatric Gastrointestinal Disease: Physiology, Diagnosis, Management, 5-th edition, 2008); (Semenza, G., Auricchio, S., and Mantei, N. In: The Metabolic & Molecular Bases of Inherited Disease; 8-th ed., 2001; Chapter 75: Small Intestinal Disaccharidoses. McGraw-Hill, New York.). Isolated intestinal trehalase deficiency is found in approximately 8% of Greenlanders; it is not infrequent among Finns, but is believed to be rare elsewhere. The low (2%) incidence of isolated trehalase enzyme deficiency was described in the populations from the USA, UK, and mainland Europe (Bergoz R, Valloton M C, and Loizeau E, "Trehalase deficiency," Ann. Nutr. Metab., 1982; 26: 191-195). In the UK, from 400 patients investigated for suspected malabsorption, 369 (92%) had normal intestinal histology on biopsy, with the normal range of trehalase at 4, 79-37, 12 U/g protein; 31 (8%) patients with villous atrophy had a diagnosis of coeliac disease and significantly reduced activity of disaccharidases, including trehalase, with recovered function of all enzymes (except lactase) after treatment with a gluten-free diet; the authors concluded that there is no basis for routine determination of trehalase activity in the population of the UK (Murray I A, Coupland K, Smith J A, Ansell I D, Long R G, "Intestinal trehalase in a UK population: Establishing a normal range and the effect of disease," Br. J. Nutr., 2000; 83(3): 241-245). In Belgium, in intestinal biopsy samples from 200 patients with abdominal symptoms and diarrhea, total ααα-trehalase deficiency (0-12 U/g mucosa) was detected in 18 (9%) cases, partial deficiency (3-12 U/g mucosa)—in 39 (19.5%) cases, and only 4 patients (2%) presented selective ααα-trehalase deficiency with otherwise normal other disaccharidases; these data suggested that ααα-trehalase deficiency can be more common than it is believed (Buts J P, Stilmant C, Bernasconi P, Neirinck C, De Keyser N, "Characterization of alpha, alpha-trehalase released in the intestinal lumen by the probiotic *Saccharomyces boulardii*," Scandinavian Journal of Gastroenterology, 2008; 43 (12): 1489-1496).

The importance of enzyme trehalase was demonstrated in certain pathologic conditions, including birth defects and genetic abnormalities: low or absent intestinal trehalase was detected in the sample of amniotic fluid from a fetus with anal imperforation, whereas a higher than normal level of renal trehalase activity was found in amniotic fluid from a fetus with polycystic kidney disease (Elsliger M A, Dallaire L, Potier M, "Fetal intestinal and renal origins of trehalase activity in human amniotic fluid," Clin Chim Acta, Jul. 16, 1993; 216(1-2): 91-102). Also, low intestinal trehalase enzyme level was detected in amniotic fluid on amniocentesis in 14 pregnant women at 1 in 4 risk for a child with cystic fibrosis, screened at the 18-th week of gestation; and in two terminated at the 19-th week cases, histochemical lesions characteristic of cystic fibrosis were seen in exocrine glands, including the pancreas and intestinal mucosa of both fetuses, and the total protein content in the meconium of these fetuses was also significantly higher than in the controls (Szabo M, Teichmann F, Szeifert G T, Toth M, Toth Z, Torok O, Papp Z, "Prenatal diagnosis of cystic fibrosis by trehalase enzyme assay in amniotic fluid," Article first published online: 23 Apr. 2008; DOI: 10.1111/j. 1300-0004. 1985.tb01211.x.). The trehalase enzyme assay in amniotic fluid was recommended as a genetic test for prenatal diagnosis of cystic fibrosis. The latest genetic studies in 2942 full-heritage Pima Indians and 3897 "mixed" heritage Native Americans with Diabetes type 2 (T2D), found strong correlation with trehalase enzyme activity in plasma of people with T2D; four single nucleotide polymorphisms (SNPs) were detected in their trehalase gene (TREH) that were associated with T2D (Yunhua L Muller, Robert L Hanson, William C Knowler, Jamie Fleming, Jayita Goswani, Ke Huang, Michael Traurig, Jeff Sutherland, Chris Wiedrich, Kim Wiedrich, Darin Mahkee, Vicky Ossowski, Sayuko Kobes, Clifton Bogardus, Leslie J Baier, "Identification of genetic variation that determines human trehalase activity and its association with type 2 diabetes", Humangenetik 2013-06-01). The Chinese research studies on genetic risk factors for glioma (one of the most aggressive human tumors), indicated that more than 100 single nucleotide polymorphism (SNPs) are associated with the risk of glioma, including the SNPs in trehalase (TREH) gene, and provided evidence for three glioma susceptibility genes—TREH, IL4, and CCDC26 (Shangu Li, Tianbo Jin, Jiayi Zhang, Huiling Lou, Bo Yang, Yang Li, Chao Chen, Yongsheng Zhang, Shanqu Li, Tianbo Jin, Jiayi Zhang, Huiling Lou, Bo Yang, Yang Li, Chao Chen, Yongsheng Zhang, "Polymorphisms of TREH, IL4 and CCDC26 genes associated with risk of glioma", Cancer Epidemiology 2012-06-01). The correlation between intestinal histology and trehalase activities during intestinal injury has been shown in clinical studies in patients with intestinal ischemia-reperfusion injury (Stefan Toth, Timea Pekarova, Jan Varga, Vladimira Tomeckova, Stephan Toth, Lucia Lakyova, Jarmila Vesela, "Trehalase as a possible marker of intestinal ischemia-reperfusion injury", Acta Biochimica Polonica 2013-01-01).

Since ingestion of large quantities of foods containing trehalose is not common worldwide, the real frequency of trehalase deficiency in various populations around the world is mostly unknown. However, it should be noted, that over the last two decades, in addition to natural sources of trehalose in the food (mostly, mushrooms, algae, baker's yeasts), it has been approved in some countries, including the USA, as an additive in the preparation of dried, frozen, and processed food, and as a moisture retainer in various products (including ice cream, and baked goods), with no requirements for labeling of this constituent in prepared food or other products (Abbott P J and Chen J, WHO Food Additives Series 46: Trehalose. International Programme on Chemical Safety. Accessed Feb. 4, 2010, available at: http://www.inchem.org/documents/jecfa/jecmono/v46je05.htm.).

The amount of enzyme trehalase normally produced for digestion and utilization of exogenous trehalose is appropriate for healthy people, but is far less than what is needed for people with biofilm-based chronic infections, especially for individuals with trehalase enzyme deficiency. Therefore, the use of enzyme trehalase, along with other enzyme formulations and antimicrobials (including antibiotics), can greatly enhance the effectiveness of various treatment protocols for biofilm-based chronic infections.

Therefore, at least one basis for the presently disclosed compositions and methods is the addition of enzyme trehalase, highly specific to the hydrolysis of the trehalose constituent of microbial biofilms, to treatment protocols for biofilm-based chronic infections in order to increase the effectiveness of existing treatment modalities.

To avoid possible immunogenicity and/or toxicity of any other sources of trehalose (animal-derived or microbial-derived enzymes) while used in humans, the best source of trehalose for use in humans can be a human genetic recombinant enzyme (human trehalase gene script expressed in rice genetically modified for human enzyme production); this manufacturing method will be analogous to production of synthetic human enzyme Lysosyme ("Lysobac") produced by Sigma-Aldrich, USA. Also, plant-derived trehalase (sugar cane trehalase—a,a-trehalase, that is located in the cytosol of the plant cells), can be used in humans; in anecdotal cases of using natural row sugar cane sticks for chewing as a sweet treat (substitute for chewing gum and candy) and using a raw (non-processed) fresh pressed sugar cane juice for food (as sugar substitute), it was demonstrated that the adult and children population in remote regions of Central America had healthy teeth, absence of dental caries and periodontal diseases, and healthy condition of the epithelial lining of the oral cavity (personal observations, not published research data). So that, the enzyme trehalase in the raw sugar cane juice (sugar cane trehalase—a,a-trehalase,) seems to be safe for use in humans, and can be used in combination with antimicrobials for prevention and treatment of microbial biofilm in the oral cavity. Also, the process of manufacturing of sugar cane trehalase can be cost-efficient regarding its possible wide use in medical and health care fields. Trehalse can be manufactured in various forms (powder, liquid, gel, tablets, and capsules) that can be tailored to specific applications in humans and delivered to any specific location in the body where biofilm is the issue (mostly mucosal linings of the oral cavity, GI tract, respiratory tract, and urinary tract, and skin lesions and wounds); trehalase can be used in combination with other saccharidase enzymes (dextranase and lyase), included in existing formulations of digestive enzymes, included in various existing formulations of vitamins, used in combination with various natural substances (anti-inflammatory and immune-modulating compounds and anti-oxidants), and can be used in combination with various antibiotics and natural antimicrobials (antimicrobial peptides of human- or plant-origin) to treat biofilm-based infections in a human body and to control biofilms on medical devices, medical equipment, and various medical implants. For industrial applications (water, gas, and oil pipelines, HV/AC systems), trehalase can be obtained from natural sources (plants, algae, fungi) using known manufacturing methods (for example, the U.S. Pat. No. 5,593,869 Jan. 14, 1997 "Method of manufacturing sugars by trehalase" includes the description of manufacturing novel enzyme trehalase from green algae of Lobosphaera, Chlorellaceae, Chlorofyceae, Chlorophyta families); in another example—method of extraction of trehalase from Sugar Cane is described in PH Dissertation of Susan Bosch, 2005, "Trehalose and Carbon Partitioning in Sugar Cane, Chapter 5, pp. 123-146, University of Stellenbosch, South Africa). However, to date, no available medical/health scientific information shows evidence of enzyme Trehalase as a component of any prescription drugs, natural antimicrobials preparation and their combinations, OTC products, nutritional supplements, vitamins combinations, digestive enzymes formulations and/or enzymatic formulations used for local treatment of microbial biofilms on skin and mucosal lining surfaces of humans, or as a component of systemic enzymes formulations, or as a component of compositions and methods for biofilm treatment on medical devices, implants, and equipment, or being a component of various disinfecting combinations for prevention and treatment of microbial biofilm on various surfaces in hospitals (including surgical units), medical offices and other medical/health settings, and public places. Also, there is no available information about the enzyme trehalase being a component of any existing anti-biofilm formulations and/or any methods for microbial biofilm prevention and treatment in industrial fluid conduits (water, gas, oil pipelines), and various industrial and household equipment.

Embodiments for the Treatment of Biofilm-Based Infections

To increase effectiveness of existing treatment modalities and protocols for biofilm-based chronic infections in the human body, combination of trehalase with antimicrobials can be used alone or in combination with other enzymes and substances (antioxidants, anti-inflammatory and immune-modulating), being included in various formulations and methods of their use, for direct application to the sites of infectious biofilm (directly accessible mucosal linings of the respiratory tract, GI-tract, genito-urinary tract, eyes, skin, open wounds, etc.) and/or for systemic use to treat biofilm-based infections in directly inaccessible (or hardly accessible) sites of infection and in the bloodstream. Simultaneously, trehalase can be used in combination with natural substances (natural antimicrobials, human antimicrobial peptides, anti-oxidants, anti-inflammatory and immune-modulating substances) to support and/or enhance body's own abilities to prevent microbial biofilm formation or degrade formed biofilm, to kill invading pathogens and eliminate them from the body, to restore normal homeostasis and immune system function, and to repair any tissue damages resulted from biofilm-based infections.

In direct application to the sites of microbial biofilm in a human body, trehalase enzyme could be used as a component of formulations of hydrolytic enzymes (including dextranase and alginate-lyase) and antimicrobials, applied in a single step to the site of infectious biofilm; or trehalase can be included in anti-biofilm combinations of enzymes and antimicrobials used in a multi-step procedure, starting as the first (pretreatment) step with application of combination of hydrolytic enzymes (trehalase, dextranase, alginate-lyase) with an exposition time sufficient to initiate degradation of the biofilm matrix, followed by the second step with application of combination of proteolytic, fibrinolytic, and lipolytic enzymes over a corresponding appropriate exposition time to further degrade the biofilm matrix, followed in a third step by application of antimicrobials (or their combinations) specific for the infection(s) involved, or polymicrobial antibiotics, in combination with trehalase for prolonged use. In this 3-step method, the initial degrading effect on biofilm matrix (provided by trehalase in combination with other hydrolytic enzymes), will ease and potentiate the action of proteolytic, fibrinolytic, and lipolytic enzymes to further degrade the biofilm matrix and provide access to microbial cells for antimicrobial substances combined with trehalase to gradually kill infectious pathogens and prevent the Biofilm Induction Response (BIR) to sub-MIC doses of antimicrobials at the initiation of treatment course. The BIR is a well-known phenomenon that is of concern in clinical practice, when killing concentration of antibiotics gradually increases at the site of microbial biofilm on initiation of treatment, allowing bacteria to initiate BIR at the very initial time of treatment (within minutes to a few hours). In addition, at the end of treatment course, some dormant microorganisms (so called persister cells) who survived antimicrobial treatment, will come back to active growing state from dormancy and will form biofilm as BIR, being exposed to the decreasing dose of antimicrobials (down to sub-MIC dose) (Jeffrey B. Kaplan, "Antibiotic-Induced Biofilm Formation. Review; Int J Artif Organs 2011; 34(9): 737-751). Therefore, the presence of trehalase in combination with antimicrobials during full treatment course, will increase the effectiveness of used antimicrobials and possibly reduce antimicrobial resistance in biofilm-forming infectious pathogens.

As a systemic enzyme, trehalase in combination with other saccharidases should be used as a time-delayed release substance(s), or being included in multi-enzyme formulations with time-delayed release of constituent(s) to avoid early degradation of trehalase and other hydrolytic enzymes (dextranase and alginate-lyase) by proteolytic enzymes in the upper GI tract (stomach and duodenum) and/or by proteolytic enzymes in administered formulations, and finally being released in the small intestine for further absorption. In this way, trehalase can be supplied for direct absorption and distribution via the bloodstream to hardly accessible "niches" of biofilm-based infections, for example, on the inner lining of the blood vessels, in bones, joints, on medical devices and implants).

The length of the time for delayed release can be established for trehalase in combination with other hydrolytic enzymes (dextranase and alginate-lyase), so that the release of these enzymes combination will occur in the small intestine, being protected from proteolytic enzymes in the upper GI tract (stomach and duodenum). Also, differential time delays can be established for combination of trehalase with other hydrolytic enzymes (dextranase and alginate-lyase) and any co-administered proteolytic enzymes (having different pH for their proteolytic activities) or a combination of these proteolytic enzymes, to avoid deleterious action of proteolytic compounds on trehalase and other hydrolytic enzymes (dextranase and alginate-lyase). In conventional digestive or systemic enzyme formulations currently on the market, the contained hydrolytic enzymes (di-, oligo-, and polysaccharidases) typically are not protected from deleterious action of various proteolytic enzymes included in existing formulations.

Upper Respiratory Tract

The major biofilm-forming species of pathogens affecting the upper respiratory tract include *Haemophilus influenzae, Klebsiella pneumoniae, Pneumococcus, Streptococcus* spp., *Staphylococcus* spp., *Pseudomonas aeruginosa, Candida* spp., and *Aspergillus* spp. For local treatment of biofilm-based infections in the upper respiratory tract (chronic sinusitis, rhinosinusitis, tonsillitis, pharyngitis, and otitis media), trehalase enzyme can be used in combination with other enzymes, antimicrobials specific to the present pathogens or polymicrobial antibiotics, or natural antimicrobials, and anti-inflammatory and immune-modulating substances in direct application to the sites of infectious biofilm on mucosal lining, in liquid form as a saline-based solution for instillations, irrigations, and sprays, as well as in gel, ointment, and powder forms.

In direct application to the sites of infectious biofilm on mucosal lining of the upper respiratory tract, trehalase enzyme could be used as a component of formulations of hydrolytic enzymes (di-, oligo-, and polysaccharidases, including dextranase and alginate-lyase as most frequently used hydrolytic enzymes) and antimicrobials, applied in a single step to the site of infectious biofilm; or trehalase can be included in anti-biofilm combinations of various enzymes, antimicrobials, anti-inflammatory and immune-modulating substances, and used in a multi-step procedure, starting as the first (pretreatment) step with application of combination of hydrolytic enzymes (trehalase, dextranase, alginate-lyase) with an exposition time sufficient to initiate degradation of the biofilm matrix, followed by the second step with application of combination of proteolytic, fibrinolytic, and lipolytic enzymes over a corresponding appropriate exposition time to further degrade the biofilm matrix, followed in a third step by application of antimicrobials (or their combinations) specific for the infection(s) involved, or polymicrobial antibiotics, in combination with trehalase, anti-inflammatory and immune-modulating substances for prolonged use. Local treatment can be reinforced by systemic use (introduced via GI tract for absorption and distribution via blood stream to the sites of infectious biofilm) of multi-enzyme formulations (including trehalase in a time-delayed release form), anti-inflammatory and immune-modulating substances, along with systemic use of antibiotics preferably with polymicrobial activity.

For local treatment of *Pseudomonas aeruginosa* infectious biofilm on mucosal lining of the upper respiratory tract, the enzyme alginate-lyase (highly specific for degradation of the polysaccharide alginate—an important constituent of *Pseudomonas aeruginosa* biofilm), should be also added to combination of trehalase with antibiotics, anti-inflammatory and immune-modulating substances for prolonged use as the third step of local application. For *Streptococcus* spp. infections, the enzyme dextranase (highly specific for degradation of the dextrans-oligosaccharides produced by *Streptococcus* spp., which facilitate microbial adhesion to the mucosal surfaces and biofilm formation, should also be added to combination of trehalase with antibiotics, anti-inflammatory and immune-modulating substances for prolonged use as the third step of treatment in local application to treat microbial biofilm in the upper respiratory tract.

Otitis Media

For otitis media with or without effusion, treatment should include a systemic enzymes formulation (including trehalase in combination with other saccharidases in time-delayed release form) along with systemic antibiotics. The systemic treatment can be reinforced with local treatment applied to the lining of the nasal cavity to address possible spread of infection to the middle ear from the nasal and sinus cavities; this local treatment should include combination of trehalase with anti-inflammatory and immune-modulating substances, and polymicrobial antibiotics or natural antimicrobial substances with wide range of anti-infectious activity (for example, colloidal silver spray). For specific treatment of *Pseudomonas aeruginosa* and/or Streptococcal biofilms, the enzymes alginate-lyase and dextranase should be added to combination of trehalase with antimicrobials. Delivery of the local treatment to the inner ear can be done by a nasal instillation with a pathway through the Eustachian tube into the middle ear.

For otitis media with effusion and installed tympanic tubes, the abovementioned systemic and local treatments should be reinforced by an additional step: the installed tympanic tubes can be covered inside with trehalase in combination with polymicrobial antibiotics or natural antimicrobials with wide range of antimicrobial activities.

Lower Respiratory Tract

Treatment of biofilm-based infections in the lower respiratory tract, should include: a) the use of systemic enzymes (with trehalase and other saccharidases in time-delayed release form) along with systemic antibiotics; b) local treatment using bronchi-alveolar or whole lung lavage in a multi-step procedure, including as the first step—the use of trehalase in combination with other saccharidases (alginate-lyase, dextranase) in a saline-based solution, followed by proteolytic, fibrinolytic, and lipolytic enzymes in a saline-based solution as the second step, and antibiotics in combination with trehalase in a saline-based solution as the third step; c) nasal instillation of trehalase in combination with anti-inflammatory and immune-modulating substances, and polymicrobial antibiotics or natural antimicrobial substances with wide range of antimicrobial activities.

Additional contributing factors to chronic biofilm-based infectious conditions are: genetic trehalase enzyme deficiency (a rare genetic disease listed by NIH Genetic and Rare Diseases Information Center), genetic trehalase enzyme deficiency in individuals with cystic fibrosis, and artificial trehalase deficiency due to widespread use of trehalose in the food industry as an approved additive in the preparation of dried and frozen foods, and as a moisture conservant, in various foods, such as an ice cream and baked goods.

Taking into account genetic trehalase deficiency in cystic fibrosis patients, uncontrolled consumption of trehalose in food is a favorable factor for thick biofilm formation on the mucosal lining of the upper and lower respiratory tracts in such individuals. *Pseudomonas aeruginosa*, in symbiosis with other bacteria and fungi, exploits this environment, creating thick polymicrobial biofilm which is almost impossible to eradicate with long-term antibiotic therapy alone (although such therapy can support the patient). Including the enzyme trehalase in combinations with antibiotics, antioxidants, anti-inflammatory and immune-modulating substances in various protocols for local and systemic treatments of biofilm-based chronic infections in patients with cystic fibrosis, will significantly increase positive outcomes of such treatment protocols and improve patients' quality of life. To address this thick polymicrobial biofilm at any stages of its development, treatment should include: a) the use of systemic enzymes (with trehalase and other saccharidases in time-delayed release form), along with systemic antibiotics; b) local treatment using bronchi-alveolar or whole lung lavage in a multi-step procedure, including as the first step—the use of trehalase in combination with other saccharidases (alginate-lyase, dextranase) in a saline-based solution, followed by proteolytic, fibrinolytic, and lipolytic enzymes in a saline-based solution as the second step, and antibiotics in combination with trehalase in a saline-based solution as the third step; c) using special enzyme "Pulmozyme" to thin the mucus in the airways of CF patients. This treatment can be reinforced by using nasal instillation of trehalase in combination with anti-inflammatory and immune-modulating substances, and polymicrobial antibiotics or natural antimicrobials with wide range of antimicrobial activities.

Native Valve Endocarditis (NVE), Infectious Endocarditis, and Line Sepsis

A preferred treatment protocol for NVE, Infectious Endocarditis, and Line Sepsis as blood stream infections, should include use of systemic enzyme formulations, with included trehalase and other saccharidases (preferably, specific to present pathogens) in time-delayed release form; and trehalase in combination with antibiotics directed to specific infectious agents, or polymicrobial antibiotics. The typical organisms involved in these biofilm-mediated infections include *Streptococci* spp, *Enterococci* spp., *Pneumococcus*, *Staphylococci* spp. (both coagulase positive and negative), gut bacteria, and fungi (most often, *Candida albicans* and *Aspergillus* spp.). Because all these pathogens gain access to the bloodstream primarily via the oropharynx, GI-tract, and genito-urinary tract, systemic treatment of NVE, Infectious Endocarditis, and Line Sepsis should be reinforced by local treatment of those infections at the sites of origin, including the previously described multi-step procedure (with application of trehalase, other enzymes, and antimicrobials) if the sites of origin represent biofilm-based infections.

Chronic Bacterial Prostatitis (CBP) and Urinary Tract Infections (UTI)

Use of systemic enzymes with included trehalase and other saccharidases in time-delayed release form, and anti-microbials in combination with trehalase will address the presence of biofilm-based chronic infections in both CBP and UTI. For local treatment of UTI via bladder instillation, a method after the fashion of a single-step procedure or the multi-step procedure disclosed above for treating biofilm on mucosal linings, should be employed: trehalase in combination with other hydrolytic enzymes (dextranase, alginate-lyase), and trehalase in combination with polymicrobial antibiotics and/or natural antimicrobials, can be applied in a single step to the site of infectious biofilm; or trehalase can be included in anti-biofilm combinations of enzymes and antimicrobials used in a multi-step procedure, starting as the first (pretreatment) step with application of combination of trehalase with other hydrolytic enzymes (dextranase, alginate-lyase) with an exposition time sufficient to initiate degradation of the biofilm matrix, followed by the next step—application of combination of proteolytic, fibrinolytic, and lipolytic enzymes over a corresponding appropriate exposition time to further degrade the biofilm matrix, and in the next step—application of trehalase in combination with antibiotics (or their combinations) specific for the present infection(s) involved, or polymicrobial antibiotics, and/or natural antimicrobials for prolonged use. For local treatment of CBP, again, trehalase can be used in combination with other enzymes and antimicrobials in a single-step application or used in multi-step procedure, but with higher concentrations of polymicrobial antibiotics and/or natural antimicrobials delivered directly to the biofilm location within the prostatic ducts by instillation means (via a medical device such as a catheter).

GI Tract Infections

GI tract infections are characterized by polymicrobial biofilm communities along with chronic parasitic and helmintic infections (nematodes are known to produce and accumulate trehalose). For treating microbial biofilms in the upper GI tract, trehalase can be included in combinations of digestive enzymes for fast release, along with use of trehalase in combination with antibiotics specific for present infection(s) and/or natural antimicrobials. For treatment of biofilm-based infections in the lower GI tract, the formulations of digestive enzymes should include trehalase with other saccharidases in time-delayed release form to avoid early degradation by proteolytic enzymes in the upper GI tract or by proteolytic enzymes in the same formulations. Digestive enzymes formulations that include trehalase in a time-delayed release form, shouls be used along with trehalase combined with antibiotics (specific for pathogenic microorganism involved or polymicrobial antibiotics, anti-parasitic, anti-helmintic and anti-protozoa drugs) and/or natural antimicrobials active against the pathogens involved. Also, optionally, trehalase can be included in combinations of digestive enzymes and specific antibiotics and/or natural antimicrobials for colonic irrigation treatment method in single-step or multi-step treatment procedures (as described for biofilm treatment on mucosal linings in the previous paragraphs).

Dental and Periodontal Diseases

The two groups of bacteria responsible for initiating dental caries, including *Streptococcus mutans* and *Lactobacillus* (known to possess multiple pathways for biosynthesis of trehalose), have direct access to high concentrations of orally ingested simple sugars and other saccharides, as well as those produced by the action of salivary amylase on ingested carbohydrates (polysaccharides), that favors the increased synthesis of trehalose and formation of microbial biofilm. Enzyme trehalase in combination with antimicrobials (ex. Chlorhexidine Gluconate), and/or with other saccharidases (ex. Dextranase) can be used for prevention of dental caries by inhibiting the formation of bacterial biofilms on the teeth and surrounding tissue surfaces.

Periodontal disease is a classic biofilm-mediated condition that is refractory to treatment by antimicrobials alone. Applied treatments, which include combination of trehalase with antimicrobials (ex. Chlorhexidine Cluconate) and added other saccharidases (ex. Dextranase), can be both preventive and curative. Combination of trehalase with antimicrobials (alone or with other saccharidases) can be used in oral application for treatment of periodontal diseases and/or during a professional dental cleaning procedure.

Also, the multi-step local treatment, including the application of trehalase in combination with antimicrobials (alone or with other saccharidases), followed by the application of proteolytic, fibrinolytic, and lipolytic enzymes, and finally by the application of trehalase in combination with antimicrobials, as disclosed above for treating infectious biofilm on mucosal linings, can be used as a curative method for periodontal biofilm-based infections. Since the bacterial biofilm is the essence of the dental plaque, the use of trehalase in combination with antimicrobials (alone or with other saccharidases) in the mouthwash or gel form can diminish the formation of the dental plaque, and in prolonged use of trehalase in combination with antimicrobials can gradually degrade and eliminate the existing bacterial biofilms.

For dental surgery, the use of combination of trehalase with antimicrobials in prepared formulations can serve as prophylaxis against biofilm-based infections. Trehalase in combination with antimicrobials (ex. Chlorhexidine Gluconate) can be used in pre- and post-operative dental surgery procedure. Additionally, it can be combined with the other materials commonly used to treat teeth in endodontics, such as dental cements.

A prophylactic application of trehalase in combination with antimicrobials (including natural antimicrobials, such as medicinal plant-derived essential oils or their active compounds) in dental hygiene includes its use in mouthwashes, toothpastes, dental floss, and chewing gum. Trehalase in combination with antimicrobials can be included into conventional non-alcohol-containing mouthwashes (to avoid alcohol-induced denaturation of the enzyme); such compositions also typically include menthol, thymol, methyl salicylate, and eucalyptol. Inclusion of trehalase in combination with antimicrobials in toothpaste is straightforward, without chemical interaction with components of conventional toothpaste; typical toothpaste formulations comprise: abrasive 10-40%, humectant 20-70%, water 5-30%, binder 1-2%, detergent 1-3%, flavor 1-2%, preservative 0.05-0.5% and therapeutic agent 0.1-0.5%. Impregnation of dental floss fibers with trehalase in combination with antimicrobials is analogous to inclusion of flavorings used in dental floss materials such as silk, polyamide, or Teflon. Finally, trehalase in combination with antimicrobials (alone or with other saccharidases) can be included in chewing gum compositions to prevent the formation of dental plaques and bacterial biofilms, as well as to treat oral biofilm-based infections in treatment protocols with antimicrobials.

Mitigation of Ingestion of Excess Trehalose by Susceptible Individuals

Owing to its unique chemical structure and properties, trehalose remains stable under low pH conditions, even at elevated temperatures, and has the ability to protect proteins in a wide range of temperature changes, including deep freezing, that makes it an attractive substance for use as a stabilizer and conservant for various products in medical and food industries. Over the last two decades, the agro-food industry has introduced the use of trehalose in many foodstuffs as a food stabilizer, sweetener, and a moisture retainer, since the high stability of trehalose enables the original product characteristics to be retained even after heat processing, freezing, and prolonged storage. Usually, the product labeling does not indicate the presence or amount of this food additive. Patients exhibiting biofilm-based infections, especially those with genetic trehalase enzyme deficiency, can be at increased risk upon consumption of the dietary trehalose, as the excess of this sugar can be used by the gut bacteria for local GI tract biofilm formation. For mitigation of these negative events, enzyme trehalase can be added in a time-delayed release form to existing formulations of digestive and systemic enzymes, to avoid negative consequences upon consumption of excess amount of dietary trehalose.

Embodiments for the Treatment of Biofilm-Based Infections on Medical Devices and Medical Equipment The methods for treatment of biofilm-based infections on medical devices and medical equipment exposed to bodily fluids and tissues comprise two categories: preventive and curative. The preventive methods of the present compositions and methods rely on altering the device and equipment surfaces by using trehalase in combination with antimicrobials, whereas curative methods exploit temporary exposure of such surfaces to treatment compositions of trehalase with antimicrobials and other compounds in various treatment protocols.

Preventive Methods

To prevent microbial biofilm growth on medical devices and equipment surfaces, trehalase in combination with antimicrobials can be used in coatings (both delayed-release and non-delayed release) and for immobilization on the surfaces of such devices and equipment. Simple (non-delayed release) coatings, comprising trehalase with antimicrobials, can be applied to metal and polymer surfaces, and fabric materials to provide a brief initial exposure of biofilm and biofilm-forming pathogens to treatment combinations. Delayed-release coatings can release trehalase and antimicrobials into the surrounding environment over time to gradually degrade biofilm and kill the embedded pathogens, ultimately depleting the initial amount of coating contained enzyme and antimicrobials. In contrast to these coatings, when combinations of trehalase with antimicrobials are immobilized on a surface of medical devices and equipment, the enzyme can act as a permanent, reusable catalyst, providing the potential for ongoing degradation of biofilm and providing antimicrobials with continuous direct access to biofilm-embedded pathogens.

Treatment coatings, containing trehalase in combination with antimicrobials, can be applied to non-porous surfaces (metal and polymer surfaces of medical devices and equipment) and porous surfaces, such as those of fabric and fabric-based surgical sewing material, surgical mesh used for hernia repair, surgical wounds, burns and skin lesions dressing materials. A foremost example is a method to prevent biofilm formation and growth on prosthetic heart valves by impregnating the fabric sewing cuff with trehalase in combination with antimicrobials before attachment of the cuff to the heart valve assembly; additionally, the heart valve assembly can be covered with an immobilized coating comprising trehalase in combination with antimicrobials. Delayed-release coatings that discharge trehalase in combination with antimicrobials over time offer the prospect of prophylactic action against the formation of microbial biofilms on the biofilm-vulnerable surfaces of medical devices and on temporary and permanent bodily implants. The delayed-release coatings can include combination of trehalase with antimicrobials embedded in surface porosity either pre-existing or specially-created at the surface, surface-attached microencapsulated trehalase with antimicrobials, and dissolvable coatings overlaying the combination of trehalase with antimicrobials on the surface. The methods of adhesion to the device or implant surfaces, and the mechanisms of time release of agents of interest are well known in the prior art and can be modified to exploit the use of trehalase in combination with antimicrobials in the present compositions and methods.

Trehalase in combination with antimicrobials can be immobilized (as discussed below in greater detail with respect to curative methods) on the biofilm-vulnerable surfaces of medical devices and equipment. The methods of enzyme immobilization on polymer and metal surfaces is described in detail by Drevon G F ("Enzyme Immobilization into Polymers and Coatings," PhD Dissertation, University of Pittsburgh, 2002). Immobilization of trehalase with antimicrobials on the surface of medical devices and equipment can be combined with other materials of antimicrobial nature, such as medical silver and medical copper, and/or with biofilm attachment preventives like Bacticent™ KB. Combination of trehalase with antimicrobials can be immobilized on a compound that serves as a support structure, and this support structure compound can be bound to device surfaces. This method insures that trehalase enzymatic activity is preserved by avoiding possible direct interaction of trehalase with the device surfaces. From among the numerous candidate support structure compounds, a choice can be optimized with respect to maintaining the enzymatic activity of trehalase while achieving high binding affinity to the device surfaces.

Combination of trehalase with antimicrobials, as treatment coatings both delayed-release and non-delayed release, as well as immobilized trehalase in combination with antimicrobials, can be used on the interior and exterior surfaces of central venous catheters and urinary catheters, and on the biofilm-vulnerable surfaces of endoscopes and implants of various types, including orthopedic implants.

The surfaces of implantable and bodily-inserted devices are targets of both the immune response and bacterial colonization, a so-called "race for the surface" (Gristina A, "Biomedical-centered infection: microbial adhesion versus tissue integration," Clinical Orthopedics and Related Research, 2004, No. 427, pp. 4-12). In the case of the immune response acting first, the macromolecule adhesion and general inflammatory action can lead ultimately to the enclosure of the device surface by a nonvascular fibrous capsule which further can support bacterial colonization and biofilm formation. If bacterial colonization occurs before overt immune response, biofilm can form immediately adjacent to the device surface. Since both the accumulation of host cells at the device surface and bacterial colonization of the surface have initial macromolecule adhesion in common, defeat of such adhesion in vivo is synergistic with use of trehalase in combination with antimicrobials to impede biofilm formation.

For this purpose, trehalase in combination with antimicrobials can be combined with new coatings that offer the promise of deterring macromolecule adhesion to synthetic surfaces. Among examples are Semprus Sustain™ technology, a polymeric approach to harnessing water molecules at device surfaces to impede macromolecule attachment, Optichem® antifouling coating with microporosity excluding macromolecule contact with the protected device surface, and zwitterionic coatings (Brault N D, Gao C, Xue H, Piliarik M, Homola J, Jiang S, Yu Q, "Ultra-low fouling and functionalizable zwitterionic coatings grafted onto SiO2 via a biomimetic adhesive group for sensing and detection in complex media," Biosens Bioelectron., 2010 Jun. 15, 25(10): 2276-2282.) that suggest the prospect of defeating protein adhesion through the exploitation of periodic reversal of polarity in the surface coating. Delayed-release coatings which include trehalase in combination with antimicrobials, can be used in concert with macromolecule-repellant coatings in various modes. For example, the combination of trehalase with antimicrobials time release sites can be established with adequate density within the confines of a macromolecule-repellant coating. Alternatively, disparate coatings can be interleaved in various geometries both parallel and perpendicular to the device surface.

Curative Methods

Methods of the present compositions and methods that address degradation and removal of biofilms and associated pathogens from surfaces involve various soak (immersion) and rinse protocols. Solutions of trehalase in combination with antimicrobials and other compounds, such as other enzymes, chelating agents, and stabilizers are anticipated. In a preferred embodiment of a soak solution, the present inventive use of trehalase enzyme to degrade the biofilm gel matrix can be viewed as an important addition to enzyme mixtures found in such products as the aforementioned Biorem. Immersive exposure to trehalase-based soak solutions can be followed by exposure to various biocidal treatments, as are well known in the prior art, for elimination of biofilm-forming pathogens. Rinse and soak solutions containing trehalase should be maintained at the temperature of maximum enzyme activity. Also, soak and immersion durations should be made sufficient for effectiveness.

A preferred method of solution-based treatment comprises the following multi-step procedure:

1—creating a first treatment solution taken from the group comprising trehalase with antimicrobials and saccharidases in aqueous or saline solution, 2—creating a second treatment solution taken from the group comprising: a) proteolytic enzymes in aqueous or saline solution, b) fibrinolytic enzymes in aqueous or saline solution, and c) lipolytic enzymes in aqueous or saline solution, 3—creating a third treatment solution taken from the group comprising: a) biocides in aqueous or saline solution, b) antibiotics, specific to the infectious agents present in aqueous or saline solution, or c) polymicrobial antibiotics in aqueous or saline solution, d) natural antimicrobials of wide range of action in aqueous or saline solution, 4—flushing or rinsing the surface under treatment with these solutions (or immersing such surface in these solutions) in the sequence given.

The exposure time for the treated surface should be sufficient for effectiveness, and such solution treatments should take place in a manner that avoids exposure of trehalase with antimicrobials and other saccharidases to proteolytic enzymes.

This multi-step procedure can be applied to treatment of central venous and urinary catheters, endoscopes, contact lenses and lens cases, dialysis system components, dental unit water lines, and other medical devices that can be subjected to immersion, rinse, or fluid injection. In the case of dialysis systems, various surfaces that contact biological fluids must be disinfected: some surfaces can be immersed in treatment solutions with the option of ultrasound-assisted cleaning, other surfaces are not immersible and simply must be soaked and flushed with treatment solutions. Also, for dialysis system components and dental unit water line treatment, the aforementioned third solution additionally can contain chelating agents and enzyme stabilizers.

An alternative avenue of delivery of trehalase in combination with antimicrobials involves immobilization of such combination by attachment to a support structure compound of some kind. In contrast to immobilization on device surfaces, as discussed above, the combination of trehalase with antimicrobials can be immobilized on a support structure compound that is in liquid suspension for use as a treatment liquid. Such immobilization of trehalase in combination with antimicrobials can permit its extended presence and repeated use in catalysis. Additionally, it can increase the enzyme's catalytic efficiency and thermal stability based on the specifics of its attachment to the support structure. There are five general categories of such immobilization: a) adsorption, b) covalent binding, c) entrapment, d) encapsulation, and e) cross-linking (Walker J M, Rapley R, and Bickerstaff G F, "Immobilization of Biocatalysts" in Molecular Biology and Biotechnology, 4th edition, edited by J. M. Walker and R. Rapley, RSC Publishing, 2007). All such mechanisms are within the scope of the present compositions and methods. In the delivery of trehalase in combination with antimicrobials to biofilm, some immediate implementations of immobilization are envisioned herein. For example, trehalase in combination with antimicrobials can be covalently bound to microspheres, as discussed below, or encapsulated in liposomes after the fashion of U.S. Pat. No. 7,824,557 (which discloses the use of antimicrobial-containing liposomes to treat industrial water delivery systems). These delivery mechanisms can be incorporated by uptake into the biofilm matrix to provide sustained exposure to trehalase in combination with antimicrobials.

The feasibility of immobilization of trehalase in combination with antimicrobials is underscored by examples of trehalase immobilization for various non-treatment purposes that can be found in the recent research literature. For analytical purposes, Bachinski et al. demonstrated the immobilization of trehalase on aminopropyl glass particles by covalent coupling that allowed the enzyme to retain its catalytic activity (N. Bachinski, A. S. Martins, V. M. Paschoalin, A. D. Panek, and C. L. Paiva, "Trehalase immobilization on aminopropyl glass for analytical use," Biotechnol Bioeng., 1997 Apr. 5, 54(1): 33-39). For reactor reuse, trehalase has been immobilized on chitin as well (A. S. Martinsa, D. N. Peixotoa, L. M. C. Paivaa, A. D. Paneka and C. L. A. Paivab, "A simple method for obtaining reusable reactors containing immobilized trehalase: Characterization of a crude trehalase preparation immobilized on chitin particles," Enzyme and Microbial Technology, February 2006, Volume 38, Issues 3-4, Pages 486-492). The present compositions and methods include immobilization of enzyme trehalase in combination with antimicrobials on support structures that have particular affinity for biofilms. U. S. Patent Application No. 20060121019 discloses the covalent and non-covalent attachment of biofilm degrading enzymes to "anchor" molecules that have an affinity for the biofilm; moieties cited as having a known affinity for biofilms included Concanavalin A, Wheat Germ Agglutinin, Other Lectins, Heparin Binding Domains, enzyme Elastase, Amylose Binding Protein, *Ricinus communis* agglutinin I, *Dilichos biflorus* agglutinin, and *Ulex europaeus* agglutinin I.

A preferred method of using immobilized trehalase in combination with antimicrobials in liquid treatment comprises the same solution-based multi-step procedure outlined above, but using immobilized trehalase in aqueous or saline suspension. Likewise, the method is similarly applicable to treatment of the same categories of medical devices disclosed above.

As mentioned earlier, ensonification of the surface to be treated can be employed to augment the removal of microbial biofilm concomitantly with soak and rinse solutions. Apart from the traditional use of ultrasound for biofilm removal, an additional modality that is within the scope of the present compositions and methods is the use of ultrasound to assist enzymatic activity. The introduction of a low energy, uniform ultrasound field into various enzyme—containing solutions can greatly improve their effectiveness by significantly increasing their reaction rate. The process is tuned so that cavitation does not result in reduction of the enzyme activity, but rather results in its significant increase.

It has been established that the following specific features of combined enzyme/ultrasound action are critically important: a) the effect of cavitation is several hundred times greater in heterogeneous systems (solid-liquid) than in homogeneous, b) in water, maximum effects of cavitation occur at ~50° C., which is the optimum temperature for many industrial enzymes, c) cavitation effects caused by ultrasound greatly enhance the transport of enzyme macromolecules toward substrate surface and, d) mechanical impacts, produced by collapse of cavitation bubbles, provide an important benefit of "opening up" the surface of substrates to the action of enzymes (Yachmenev V, Condon B, Lambert A, "Technical Aspects of Use of Ultrasound for Intensification of Enzymatic Bio-Processing: New Path to "Green Chemistry", "Proceedings of the International Congress on Acoustics, 2007). Enzyme reaction rates can be increased by more than an order of magnitude. In an example of specific enzyme application, alpha-amylase reaction rates were increased with the use of ultrasound (Zhang Y, Lin Q, Wei J N, and Zhu H J, "Study on enzyme-assisted extraction of polysaccharides from Dioscorea opposite," Zhongguo Zhong Yao Za Zhi. 2008 February, 33(4): 374-377). For ultrasound-assisted enzyme-based treatment, the solution-based multi-step treatment previously disclosed, can be modified to include ensonification of enzyme-containing treatment solutions and surfaces under treatment.

Embodiments to Address Industrial Biofilms.

There are numerous industrial biofilm treatment approaches that can be enabled by the use of trehalase enzyme in combination with antimicrobials. These approaches involve both creation of appropriate mixtures of trehalase with antimicrobials and other compounds, and development of methods for delivery of these mixtures to the sites of biofilm presence.

With respect to treatment mixtures, the combination of trehalase with antimicrobials can be used alone in aqueous or saline solution or can be added to compounds that maintain the optimum pH range (buffer compositions), and metallic ion concentrations that can maximize the hydrolysis rate of trehalose. Additionally, one or more combinations of trehalase with antimicrobials can be added to compositions of dispersants, surfactants, detergents, other enzymes, and biocides that are delivered to the biofilm in order to achieve synergistic effects. Also, trehalase in combination with antimicrobials can be used as a pretreatment step in various protocols involving other biofilm treatment compounds and/or methods.

Also, combination of trehalase with antimicrobials can be immobilized on substrate compounds in liquid suspensions, as discussed above, for use in industrial treatments, where the substrate compound may have an affinity for the target of treatment.

For oil pipelines, an oil-water emulsion containing trehalase in combination with antimicrobials will provide a dosing opportunity to treatment of the biofilms within the pipeline. These emulsion-borne mixtures can include combination of trehalase with antimicrobials alone, or with additional conventional treatment compounds such as other biocides, surfactants, detergents, and dispersants as are well known in the prior art.

A specific treatment embodiment for pipelines involves the exploitation of annular liquid flow geometries. The annular flow pattern of two immiscible liquids having very different viscosities in a horizontal pipe (also known as "core-annular flow") has been proposed as an attractive means for the pipeline transportation of heavy oils since the oil tends to occupy the center of the tube, surrounded by a thin annulus of a lubricant fluid (usually water) (Bannwar A C, "Modeling aspects of oil-water core-annular flows," Journal of Petroleum Science and Engineering Volume 32, Issues 2-4, 29 Dec. 2001, Pages 127-143). A thin water film can be introduced between the oil and the pipe wall to act as a lubricant, giving a pressure gradient reduction. In 8-inch diameter pipes, it has been shown that, under certain conditions, it is possible to use very thin water films. For crude oils with viscosities exceeding 2000 mPas, stable operation has proved feasible with as little as 2% water (Oliemans R V A, Ooms G, Wu H L, Duijvestijn A, "Core-Annular Oil/Water Flow: The Turbulent-Lubricating-Film Model and Measurements in a 2-in. Pipe Loop," Middle East Oil Technical Conference and Exhibition, 11-14 Mar. 1985, Bahrain.). In an embodiment of the present compositions and methods to address delivery of trehalase with antimicrobials-containing solutions to the interior of oil pipelines, the thin water film is replaced by a trehalase with antimicrobials in aqueous solution. This combination of trehalase with antimicrobials in aqueous solution will be a flowing annular layer immediately adjacent to the inner surface of the pipeline.

Another embodiment of the compositions and methods, addressing microbial biofilm in the oil pipelines, comprises the exploitation of magnetic force to deliver trehalase in combination with antimicrobials to the target treatment sites within pipelines. Specifically, combination of trehalase with antimicrobials can be immobilized on a support structure compound that exhibits either magnetic or preferably ferromagnetic properties. When this immobilized combination of trehalase with antimicrobials is released into pipeline flow, a magnetic field exterior to the pipeline can be used to guide and retain the immobilized combination of trehalase with antimicrobials in the target vicinity on the interior of the pipeline. The magnetic field can be generated by magnetic or electromagnetic means well known in the prior art. Optimization of this embodiment could include spatial and temporal variation of the generated magnetic field to achieve appropriate concentration of trehalase in combination with antimicrobials at treatment sites in the presence of fluid flow. Residual magnetism induced in the pipeline wall can be diminished by methods well known in the prior art.

Dry dock removal of hull biofouling material, including biofilms, can use aqueous solutions containing trehalase in combination with antimicrobials in rinse and/or soak protocols. Application of hydrogel containing trehalase in combination with antimicrobials to ships' hull is another means of ensuring sustained exposure of the biofilm for hydrolysis of the trehalose component of the biofilm matrix and initial elimination of biofilm-embedded microorganisms. This can be done prior to or at the time of additional biocide application. Further, the biofilm preventive coatings, containing combination of trehalase with antimicrobials, can be immobilized on marine surfaces. The solution-based, multi-step treatment that includes trehalase in combination with antimicrobials discussed for medical device treatment can be used in the marine surface applications, or it can be modified to use gel delivery of treatment compounds instead of aqueous or saline solutions.

For HVAC systems the solution-based multi-step treatment method that includes combination of trehalase with antimicrobials and other compounds, can be used as stated for certain components such as cooling coils and drain pans, or modified so that treatment compounds can be fed into HVAC ductwork in the form of aerosols.

Candidate industrial biocides for use along with trehalase in combination with antimicrobials include popular industrial biocide products on the market such as Ultra Kleen™ manufactured by Sterilex Corp., Hunt Valley, Md., the active ingredients of which comprise:

n-Alkyl(C14 60%, C16 30%, C12 5%, C18 5%) dimethylbenzylammonium chloride; and n-Alkyl(C12 68%, C14 32%) dimethylethylbenzylammonium chloride.

Another example is SWG Biocide manufactured by Albermarle Corp., Baton Rouge, La., the active ingredients of which comprise sodium bromosulfamate and sodium chlorosulfamate. Candidates may also be found among the wider generic categories of industrial biocides comprising: glutaraldehyde, quaternary ammonium compounds (QACs), blends of Gut and QACs, Amine salts, Polymeric biguanide, benzisothiazolone, blend of methyl isothiazolones, and acrolein (Handbook of Biocide and Preservative Use, Edited by H. W. Rossmoore, Chapman and Hall, 1995).

For treatment of biofilms associated with food processing, storage, and transport systems, conventional enzyme treatments can be augmented with the use of trehalase in combination with antimicrobials. This can be done in the context of the solution-based multi-step procedure. In addition, the present compositions and methods include the use of trehalase in combination with antimicrobials and other enzymes in one-step procedure, given that added enzymes are not proteolytic. Also, ultrasound-assisted enzyme-based cleaning is applicable with the use of trehalase in combination with antimicrobials.

Biofilms are found in the household environment on many surfaces including the inside surfaces of plumbing and drainpipes, on the surfaces of sinks, bathtubs, tiling, shower curtains, shower heads, cleaning sponges, glassware, toothbrushes, and toilets. Aqueous- or saline-based solutions containing trehalase in combination with antimicrobials can be used alone or in proper combination with other biofilm treatment products tailored to the applicable surfaces in cleaning procedure. For example, certain compounds used for plumbing treatment would be inadmissible for treating toothbrushes. The aforementioned solution-based multi-step procedure easily can be applied to many household surfaces with the exception of the internal surfaces of plumbing.

Test Results.

There now follows a summary of various in vitro test results using Trehalase to determine Trehalase potential in gram-positive and gram-negative bacteria and determine the effect of Trehalase in combination with the antibiotics ceftazidime (CAZ), gentamicin (GENT) and tobramycin (TOB) both with grown biofilms, added at the beginning of experiments, and added to an early 24-hour grown and late 48-hour grown preformed biofilms during a 24-hour exposition. The effect of Trehalase in gram-positive bacteria (MRSA and MSSA) *S. aureus* and in gram-negative bacteria *P. aeruginosa* is also summarized. Following this summary is a more detailed explanation of the experimental process with supporting graphs and charts for the results. The tests were conducted and summarized by the Drug Discovery and Development Pharmaceutical Services Company Aptuit, LLC in Verona, Italy.

It is well known that Gram-positive and Gram-negative bacteria use a ubiquitous multifunctional sugar, i.e., disaccharide trehalose, as a general stress response metabolite and osmoprotectant, to form biofilm as a protective cover against harmful environmental factors, and to preserve integrity of the bacterial cells for survival in a hazardous environment (including the milieu of the human body). The results from the testing show that the enzyme Trehalase, highly specific for degrading disaccharide trehalose (one substrate-one enzyme), can be effectively used for prevention and treatment of microbial biofilms, overcome bacterial resistance to antimicrobials, and increase the effectiveness of existing treatment modalities. Due to structural differences of Gram-positive and Gram-negative bacteria, the effect of applied enzyme Trehalase can have some special features in both types of bacteria.

Because Trehalose is a structural element in the cell wall of Gram-positive bacteria, the use of the external enzyme Trehalase can affect not only biofilm formation, but also can exert certain effects on the bacterial cell wall and cell membrane, increasing their permeability to antibiotics, and possibly decreasing antimicrobial resistance. Gram-negative bacteria has the intrinsic enzyme Trehalase present in the outer membrane space (acidic Trehalase) that degrades trehalose released from the cytosol for recycling, and metabolizes trehalose taken from outside the cell for intracellular utilization. In Gram-negative bacteria, the application of external enzyme Trehalase may require more time for addressing the biofilm formation, and taking longer to exert an effect on the cell membranes, but still influencing their permeability to antibiotics and decreasing antimicrobial resistance in many cases.

The results of in vitro studies performed by Aptuit, LLC demonstrated some differences in the effect of the enzyme Trehalase (alone and in combination with antibiotics) on microbial biofilms produced by Gram-positive and Gram-negative bacteria. The enzyme tested in the study was an enzyme of mammalian origin, i.e., pig kidney Trehalase, produced by "Sigma-Aldrich" (USA), which in some tests was later purified by a dialysis procedure developed by Aptuit/Verona S.r.l. as will be explained briefly below.

Various parameters that were evaluated in each part of the analysis include: 1) Biofilm mass formation (% inhibition—by Crystal Violet staining method); 2) Bacterial cell viability (% inhibition—by Resazurin assay); and 3) Bacterial cell growth (by Colony Counting—CFU/ml plating).

One in vitro test was an exploration of the Trehalase potential in gram-negative bacteria and an exploration of Trehalase Potential in Gram-Negative Bacteria (*P. aeruginosa* PAO1-reference strain), and which showed an effect of Trehalase alone added to the media (TSB) at the beginning of a 72 hour experiment. Trehalase alone inhibited biofilm mass formation in a dose-dependent manner. From various doses (0.023, 0.046, and 0.092 U/well) the highest effect was seen with 0.092 U/well. The "U" corresponds to the International Units for the enzyme in each testing well. This dose was further used in subsequent experiments. Compared to a control, Trehalase alone inhibited the biofilm mass formation during 72 hours of biofilm growth, with the most significant inhibition noted at the initial (4 hour) stage of biofilm development at 83.3%. In an early (24 hour) mature biofilm inhibition was 82.4%, and in fully mature (48 hour) biofilm inhibition was at 91.0%. In an old stage (72 hour of growth), the biofilm formation was still inhibited by about 50.0%. It appears that Trehalase alone did not affect the bacterial cell viability and growth at various stages of the biofilm development (4 hours, 24 hours, and 48 hours), as confirmed by Resazurin assessment and bacterial counting (CFU/ml), i.e., colony-forming unit per milliliter. At the same stages of biofilm development (4 hours, 24 hours, and 48 hours), no effect on biofilm formation and cell viability was seen with solvent present in the Sigma Trehalase preparation (Glycerol/water 50/50 solution and 1% Triton-X100) used in the testing.

A next series of tests explored the effect of Trehalase in combination with the antibiotics Ceftazidime (CAZ) and Tobramycin (TOB) in ¼ and ⅛ sub-MIC (Minimum Inhibitory Concentration) doses in 24 hour to 48 hour grown biofilms that were added at the beginning of the experiments. Trehalase alone demonstrated continuing inhibitory effect on the biofilm mass formation with longer exposition time (about 65% inhibition in a 48 hour grown biofilm) with no effect on bacterial cell viability and growth in both 24 hour and 48 hour grown biofilms. Both antibiotics (CAZ and TOB) in sub-MIC doses (⅛ and ¼ MIC), introduced to the media at the beginning of experiment, triggered the Biofilm Induction Response (BIR) in 24 hour grown and in 48 hour grown biofilm, increasing biofilm mass formation by 1.2 to 1.3 (CAZ) and 1.3 to 1.7 fold (TOB) compared to the Control level, i.e., the level of biofilm mass formed by *P. aeruginosa* PAO1 in the absence of antibiotics. When Trehalase was added to antibiotics, it abrogated the biofilm induction response "BIR" to both antibiotics (CAZ and TOB) in the 24 hour grown biofilm down to the Control level, with an additional reduction (about 30%) in the biofilm mass formation only for the Trehalase/TOB combination. With a longer exposition time in the 48 hour grown biofilm, Trehalase added to antibiotics, demonstrated higher effect, abrogating biofilm induction response "BIR" to both antibiotics down to the Control level, with an additional reduction of biofilm mass formation by about 65% for the Trehalase/CAZ combination and by about 70% for the Trehalase/TOB combination ($p<0.001$; $p<0.001$ compared to the Control). Tobramycin alone (at a dose of ¼ MIC) inhibited cell viability (by Resazurin assay) by about 25% in both the 24 hour and 48 hour grown biofilms. The Tobramycin/Trehalase combination enhanced this inhibitory effect up to 45% only in the 24 hour grown biofilm. Ceftazidime alone at a dose of ⅛ and ¼ MIC inhibited cell viability (Resazurin assay) by about 25% to 50% only with the longer exposition, i.e., in the 48 hour grown biofilm. The CAZ/Trehalase combination did not enhance this effect.

A next series of tests explored the effect of Trehalase alone and in combination with the antibiotics Ceftazidime (T+CAZ) and Tobramycin (T+TOB) in ¼ MIC doses, added to the early (24 hour grown) preformed biofilm during the 24 hours of further exposition. When added to the early (24 hour grown) pre-formed biofilm, Trehalase alone inhibited further biofilm mass formation by about 30% ($p=0.08$) (during the 24 hour exposition). Both antibiotics (CAZ and TOB) in sub-MIC doses (¼ MIC) added to the early (24 hour grown) preformed biofilm, triggered "BIR", increasing biofilm mass formation by about 1.6 (CAZ) and about 1.4 (TOB) compared to the Control level (i.e. the level of biofilm mass formed by *P. aeruginosa* PAO1 in the absence of antibiotics). Trehalase in combination with antibiotics, added to 24 hour preformed biofilm, abrogated "BIR" to both antibiotics, and additionally slightly reduced biofilm mass formation by about 10% (T+CAZ) and about 37% (T+TOB) compared to the Control level. Trehalase alone and in combination with both antibiotics (T+CAZ and T+TOB) as added to a 24 hour preformed biofilm did not inhibit bacterial cell viability and growth by Resazurin assay and Colony counting (CFU/ml).

For the Gram-negative pathogen *P. aeruginosa* PAO1, trehalase alone added at the beginning of the experiment significantly inhibited the biofilm mass formation during the 72 hours of biofilm growth, with the highest inhibition noted at the initial (4 hour) stage of biofilm development at 83.3%. In the early (24 hour) mature biofilm, the inhibition was 82.4%. In the fully mature (48 hour) biofilm, the inhibition was 91.0%. In the old stage of growth (72 hour), the biofilm formation was still inhibited by about 50.0%. Trehalase alone did not appear to affect bacterial cell viability and growth at various stages of the biofilm development (4 hour, 24 hour, 48 hour, and 72 hour), as confirmed by Resazurin assay and Bacterial Cell Counting (CFU/ml). Trehalase in combination with the antibiotics cephalosporin Ceftazidime and aminoglycoside Tobramycin in sub-MIC doses (⅛ and ¼ MIC), was effective in the 24 hour to 48 hour grown biofilms, first by abrogating the Biofilm Induction Response (BIR) to both antibiotics, and second by continuing inhibition of biofilm mass formation with longer exposition time, with the additional reduction of biofilm mass by about 65% (T+CAZ) and about 70% (T+TOB) ($p<0.001$; $p<0.001$ compared to the Control), which occurred in the 48 hour grown biofilm. Trehalase slightly potentiated the inhibitory effect of Tobramycin on biofilm cell viability (by Resasurin assessment) in the 24 hour grown biofilm by about 45% inhibition for the Trehalase/Tobramycin combination, compared to about 25% inhibition for the Tobramycin alone.

These tests show positive results for the use of Trehalase as an adjuvant to antibiotics for the prevention and treatment of biofilm-based chronic infections caused by Gram-negative pathogens, including drug-resistant bacteria. The Biofilm Induction Response "BIR" to sub-MIC doses of antibiotics is a known phenomenon and is considered to be the first step in antimicrobial resistance in Gram-positive and Gram-negative bacteria, and is important in clinical practice during the "adjustment" period of antibiotic use, both at the beginning and the end of the treatment course.

In all of these tests, a Trehalase product from Sigma-Alrich was used as derived from porcine kidney with a buffered aqueous glycerol solution of greater than or equal to 1.0 units/milligram protein. An example product can be acquired from Sigma-Alrich as:
Product Number: T8778
CAS Number: 9025-52-9
MDL: MFCD00132462

| TEST | SPECIFICATION |
| --- | --- |
| Appearance (color) | Colorless to light yellow |
| Appearance (form) | Liquid |
| Appearance (turbidity) | Clear to slightly hazy |
| units/mg protein - one unit will convert 1.0 micromole of Trehalose to 2.0 micromoles of glucose per minute at pH 5.7 and at 37° C. (liberated glucose determined at pH 7.5) | ≥1.0 |
| alpha-Galactosidase | ≤1% |
| alpha-Glucosidase | ≤1% |
| β-Glucosidase | ≤5% |
| Invertase | ≤1% |
| Amylase | ≤2% |
| mg protein/ml (BCA) | 0.5-10.0 |

There now follows greater details about tests that show the effect of Trehalase in gram-positive bacteria (MRSA and MSSA *S. aureus*). A first test showed the effect of Trehalase on initial biofilm formation by MRSA *S. aureus* ATCC 25923 (lab strain). Trehalase alone (at a dose of 0.092 U/well) was added to the media as a Trypticase soy broth (TSB) at the beginning of the experiment, and inhibited the initial biofilm mass growth ($p<0.001$ compared to the Control), most significantly (about 85% to about 90%) at the very early stages (3 hour and 7 hour) of biofilm formation, and about 67% in the early (28 hour) mature biofilm. It inhibited viability of bacterial cells in the biofilm (about 84%, about 81%, and about 63% correspondingly by Resazurin assay), and reduced the bacterial cell growth in the 24 hour biofilm (about 1.5 log by CFU/ml compared to the Control). Trehalase did not affect bacterial cell viability and growth in the population of planktonic cells in the supernatant removed after 24 hours of biofilm growth.

A second test showed the effect of Trehalase in combination with the antibiotics Ceftazidime (CAZ) and Gentamicin (GENT) in sub-MIC doses (¼ and ⅛ MIC) in early (24 hour grown) biofilm formed by MRSA *S. aureus* ATCC 25923 [MIC Ceftazidime on *S. aureus* ATCC 25923=8 ng/mL by CLSI guidelines]; [MIC Gentamicin on *S. aureus* ATCC 25923=2 µg/mL (by CLSI guidelines]. When Trehalase (at a dose 0.092 U/well) in combination with both antibiotics (CAZ and GENT) in sub-MIC (⅛ and ¼ MIC) concentrations, was added to the media (TSB) at the beginning of experiment, it demonstrated a synergistic effect on all parameters in the study in the 24 hour grown biofilm.

There was a synergistic effect of the Trehalase in combination with Ceftazidime. Biofilm mass formation was inhibited by about 48% (T), by about 15% to 20% (CAZ), and about 60% (T+CAZ). Biofilm cell viability (by Resazurin assay) was inhibited by about 62% (T), by about 13% (CAZ in both sub-MIC doses), and by about 88% to 90% (T+CAZ in both sub-MIC doses). Biofilm cell growth (CFU/mL) was reduced by about 1.67 log-1.77 log by T+CAZ in both sub-MIC doses ($p<0.001$, $p<0.001$, $p<0.001$ compared to the Control, Trehalase alone and Ceftazidime alone correspondingly). There was no effect on planktonic cells from supernatant removed after 24 hours of incubation was recorded.

There was a synergistic effect of Trehalase in combination with Gentamicin. The synergistic effect of Trehalase in combination with Gentamicin (T+GENT) in both sub-MIC doses ⅛ and ¼ MIC) in 24 hour grown biofilm was significantly higher than in combination with. Ceftazidime, demonstrating. The inhibition of biofilm mass formation by about 90% to 92% ($p<0.001$, compared to the Control) and the full (100%) inhibition of bacterial cell viability (by Resazurin assay). It also completely abrogated bacterial cell growth in both populations of the cells by about 3.73 log in biofilm cells, and by about 3.31 log in planktonic cells from supernatant removed after 24 hour of incubation (down to the "limit of detection," i.e., mean—12500 CFU/mL) ($p<0.001$, $p<0.001$, compared to Control).

A series of tests were conducted to show the effect of Trehalase in combination with the antibiotics Ceftazidime (CAZ) and Gentamicin (GENT) on early (24 hour grown) and late (48 hour grown) preformed biofilms formed by MRSA *S. aureus* ATCC 25923 [Antibiotic concentrations used in the experiment: Ceftazidime 2 µg/mL=¼ MIC; Gentamicin—0.5 µg/mL=¼ MIC]. Trehalase (at a dose 0.092 U/well) in combination with both antibiotics (CAZ and GENT) in sub-MIC (¼ MIC) doses, added to the early (24 hour grown) and late (48 hour grown) preformed biofilms, demonstrated synergistic effect on all parameters in the study during the next 24 hour of exposition, with the higher effect on the late preformed biofilm. The combination of trehalase with a sub-MIC dose (¼ MIC) of Gentamicin (GENT) appeared to be the most efficacious.

Trehalase alone (T) and in combination with both antibiotics, added to the early (24 hour) preformed biofilm, significantly inhibited further biofilm growth (during 24 hour exposition) by about 48% (T), by about 56% (T+CAZ), and by about 54% (T+GENT) [p<0.001, p<0.001, p<0.001, compared to the Control and antibiotics alone]. The inhibitory effect was higher in the late (48 hour) preformed biofilm: about 80% (T), about 70% (T+CAZ), and about 83% (T+GENT) [p<0.001, p<0.001, p<0.001, compared to the Control and antibiotics alone].

Trehalase alone, added to the early (24 hour) and late (48 hour) preformed biofilms, inhibited bacterial cells viability (by Resazurin assay) approximately to the same extent of about 48% (T). Trehalase in combination with both antibiotics showed a robust inhibition of cell viability approximately to the same extent in both early and late preformed biofilms: by about 70% to 80% (T+CAZ) and about 70% to 76% (T+GENT). Trehalase alone slightly inhibited biofilm cell growth in the early preformed biofilm (about 0.96 log), and showed higher inhibition in the late preformed biofilm (about 1.6 log, p<0.05 compared to the Control).

Trehalase in combination with Ceftazidime (T+CAZ) inhibited biofilm cell growth in both early and late preformed biofilms (p<0.001), with some higher effect of combination T+CAZ in the early preformed biofilm (about 1.96 log) than in the late preformed biofilm (about 1.64 log) [p<0.01, compared to control], and by about 1.53 log [p<0.01] compared with CAZ alone in early preformed biofilm. Trehalase in combination with Gentamicin (T+GENT) significantly inhibited biofilm cell growth in both early and late preformed biofilms (by about 3.06 log and about 3.49 log correspondingly, p<0.001, p<0.001 compared to the Control). It also significantly inhibited biofilm cell growth compared to inhibition by Gentamicin alone, i.e., by about 2.61 log (p<0.01) in the early preformed biofilm, and by about 3.26 log (p<0.001) in the late preformed biofilm.

A next series of tests evaluated a purified (dialyzed) Trehalase on bacterial growth, cell viability and biofilm mass formation in early biofilm (24 hour grown) and early preformed biofilm (preformed for 24 hours) produced by S. aureus ATCC 25923 [experimental dialysis of Sigma Trehalase using "Amicon-R Ultra—15 Centrifugal Filter Devices" (Sigma-Aldrich), method modified by Aptuit].

In the early (24 hour grown) biofilm, dialyzed Trehalase (at a dose 0.092 U/well) added at the beginning of experiment, inhibited the biofilm mass formation by about 72% (p<0.001, compared to Control), with no effect on biofilm cell viability (by Resazurin assay) and growth (by colony counting—CFU/mL). No inhibitory effect on biofilm mass formation, biofilm cell viability and growth was detected with solvent (potassium phosphate buffer) in dialyzed Trehalase. Dialyzed Trehalase (at a dose of 0.092 U/well) added to 24 hour preformed biofilm, inhibited bacterial cell growth (by colony counting): T—1.36E+08 CFU/mL (p<0.001, compared to the Control—1.06E+09 CFU/mL). Potassium phosphate buffer (solvent in dialyzed Trehalase) did not show any inhibitory effect on bacterial cell growth in 24 hour preformed biofilm.

These series of tests show that the dialyzed porcine kidney Trehalase (prepared with potassium phosphate buffer as a solvent) was confirmed to be at least as active as the Sigma Trehalase enzyme (prepared with its solvent containing: 50% glycerol/water solution+1% Triton-X100 and 25 mM potassium phosphate, pH 6.5). The performed dialysis reduced to the minimum the possibility of the inhibitory effect of Sigma Trehalase solvent on biofilm formation and viability of the bacterial cells.

Tests were conducted to show the effect of dialyzed Trehalase on biofilm formed by Gram-positive Bacteria (lab strains and clinical isolates: MRSA S. aureus ATCC25923, S. aureus ATCC33591, 3—Belgium, and VRE/VSE E. faecalis ATCC29212; IH851165; E. cocco 14) in 24 hour grown biofilm. Due to some negative effect of potassium phosphate buffer on VRE/VSE E. faecalis ATCC29212, IH851165, E. cocco 14, the following studies were performed only on MRSA and MSSA S. aureus laboratory strains and clinical isolates.

Results showed the effect of Trehalase alone and in combination with the antibiotics Gentamicin and Vancomycin in sub-MIC doses (¼ MIC) in the early (24 hour grown) biofilms formed by the lab strains and clinical isolates of S. aureus, regarded as the good (high), medium, and poor (low) biofilm producers. All strains had the same sensitivity (MIC) to Vancomycin, but a different sensitivity to Gentamicin.

The test showed the effect of Trehalase alone and in combination with antibiotics Gentamicin and Vancomycin in sub-MIC doses (¼ MIC) in the early (24 hour grown) biofilm produced by MRSA S. aureus ATCC25923, which is a lab strain known as a "good (strong) biofilm producer" (Gentamicin: MIC=0.125 µg/ml; Vancomycin: MIC=2.0 µgimp. There is strong reproducibility of the data generated with S. aureus ATCC25923 (similar activity among different experiments). In a 24 hour grown biofilm, Trehalase alone, at a dose of 0.092 UI/well, significantly inhibited biofilm mass formation by about 90% (p<0.001, compared to Control) and decreased biofilm cell viability by about 40% (by Resazurin assay). Both antibiotics Gentamicin (GENT) and Vancomycin (VAN) in sub-MIC doses (¼ MIC) triggered the biofilm induction response (BIR), that resulted in increased biofilm mass by two-fold (GENT) and 1.8-fold (VAN) (p<0.001, p<0.001, compared to the Negative Control), with no effect on cell viability and growth. Trehalase in combination with antibiotics, the abrogated biofilm induction response to both antibiotics and further significantly decreased biofilm mass formation to the same degree as Trehalase alone did: by about 90% (for both combinations T+GENT and T+VAN, p<0.001, p<0.001, compared to the Control), and also inhibited biofilm cell viability by about 50% (T+GENT) and by about 30% (T+VAN) (by Resazurin assay).

Tests also showed the effect of Trehalase alone and in combination with the antibiotics Gentamicin and Vancomycin in sub-MIC doses (¼ MIC) in the early (24 hour grown) biofilm produced by MSSA S. aureus ATCC33591, known as a "medium biofilm producer" (Gentamicin: MIC=2.0 µg/ml; Vancomycin: MIC=2.0 µg/ml). Trehalase alone, at a dose 0.092 UI/well, significantly inhibited biofilm mass formation by about 67% (p<0.001, compared to the Control), with no effect on biofilm cell viability (by Resazurin assay) and growth (by colony counting as CFU/mL). Neither Gentamicin (GENT), nor Vancomycin (VAN) in sub-MICc doses (¼/MIC) triggered biofilm induction response. They both even showed a slight reduction in biofilm mass formation: about 10% (GENT) and about 20% (VAN) compared to the Control. Trehalase in combination with both antibiotics, significantly inhibited biofilm mass formation to the same degree as Trehalase alone did (by about 67% for both combinations T+GENT and T+VAN, p<0.001, p<0.001, compared to the Control). Trehalase in combination with Gentamicin (T+GENT) significantly inhibited biofilm cell viability (about 80% by Resazurin assay), and significantly reduced bacterial cell growth (p<0.05, compared to negative Controls, by colony counting as CFU/mL) in populations of both biofilm cells and planktonic cells removed from supernatant after 24 hour of biofilm growth. No such effects were recorded for Trehalase in combination with Vancomycin.

The tests showed the effect of Trehalase alone and in combination with antibiotics Gentamicin and Vancomycin in sub-MIC doses (¼ MIC) on biofilm produced by *S. aureus* 3-Belgium, clinical isolate, known as a "poor (low) biofilm producer" (Gentamicin: MIC=32.0 µg/ml; Vancomycin: MIC=2.0 µg/ml). Trehalase alone or in combination with sub-MIC (¼ MIC) doses of Gentamicin and Vancomycin did not induce a decrease in terms of biofilm mass formation, biofilm cell viability (by Resazurin assay) and bacterial cell growth (CFU/mL).

Further tests were conducted to explore the MIC (Minimum Inhibitory Concentration) determination with selected *S. aureus* strains (MSSA Oxford and MSSA ATCC 35556, and MRSA ATCC 25923) in the presence and absence of Trehalase [in vitro assay: Gentamicin, Vancomycin, Ciprofloxacin—MIC in broth according to CSLI guidelines]. Addition of Trehalase resulted in significant MIC value reduction with Gentamicin (up to 16-fold and 33-fold with clinical and reference isolates). No significant effect on Vancomycin MIC and Ciprofloxacin MIC was observed. There was testing of Trehalase on Clinical Isolates (*S. aureus* strains: Oxford, ATCC35556, and ATCC 25923 as the reference strain) at a time-point: 24 hours of biofilm growth.

Trehalase alone (at a dose 0.092 UI/well), added to the media at the beginning of experiment, significantly reduced biofilm mass formation with all three *S. aureus* strains tested: about 80% (ATCC25923), about 90% (ATCC35556), and about 50% (Oxford) ($p<0.001$, $p<0.001$, $p<0.05$ correspondingly, compared to the Control). In the presence of Trehalase, the biofilm cell viability (by Resazurin assay) was inhibited with all tested *S. aureus* strains: by about 40% (ATCC25923), about 25% (ATCC35556), and about 60% (Oxford). Biofilm cell growth (by colony counting as CFU/mL) was significantly reduced ($p<0.05$ compared to Control) in biofilms formed by *S. aureus* ATCC25923 (lab reference strain) and *S. aureus* Oxford (clinical isolate). No effect on planktonic cell growth was recorded. Overall, Trehalase added to the media at the beginning of experiment with the early (24 hour grown) biofilm, induced a reduction in biofilm mass formation and inhibition of viability of all three selected MSSA and MRSA strains at a 24 hour time-checking point.

Further tests showed the effect of Trehalase, added during the initial biofilm growth (up to 24 hours) and after 24 hours of initial biofilm growth (up to 24 hours of further incubation) on a catheter segment (14-gauge Teflon intravenous catheter): in vitro assay with *S. aureus* XEN 29, adapted by Kadurugamuwa et al., 2003). The bioluminescence signal on catheter was detected with the IVIS Lumina image system, and bacterial count (both biofilm and planktonic cells) was evaluated by colony counting (CFU/ml, agar plating). The addition of Trehalase at the beginning of the initial 24 hour biofilm growth, induced a significant reduction in biofilm mass formation on a catheter segment (inner and outer surfaces) as demonstrated by significantly lower intensity of bioluminescence signal with *S. aureus* XEN 29+Trehalase 0.092 UI, compared to the Negative Control (Blank), Positive Control (*S. aureus* XEN 29), and Vehicle (*S. aureus* XEN 29+buffer content 25 mM potassium phosphate, pH 6.5). Bacterial cell growth (CFU/ml) was significantly reduced in both bio film cells and population of planktonic cells ($p<0.05$, $p<0.05$, compared to Positive Control). There was no effect of Trehalase added after 24 hours of biofilm growth on catheter segment in terms of bioluminescence signal intensity and bacterial cell growth (CFU/ml), compared to Positive Control and Vehicle.

There now follows further details of the various experimental designs and materials and methods used to conduct many of the tests explained above. Various charts and tables that reflect the tests and conclusions drawn from these tests are also explained with reference to the drawing figures.

A number of the tests explained above evaluated the potential synergistic effect of a combination between trehalase and three antibiotics (at sub-MIC concentrations) on bacterial growth, viability and biofilm mass in early (24 hours) and late (48 hours) preformed biofilms produced by *S. aureus* ATCC25923 and *P. aeruginosa* PAO1. The experimental design in this test for a first strain included:

Strain: *P. aeruginosa* PAO1
Temperature: 35±2° C.
Incubation Conditions: Static
Time Points: 24-48 hours preformed biofilm
Treatment: (added to well containing a suspension of *P. aeruginosa* PAO1 ~$10^7$ CFU/ml)
Solvent Content: 50% glycerol containing 1% Triton™ X-100 and 25 mM potassium phosphate, pH 6.5
Trehalase Content: 0.092 UI
Antibiotic Concentration:
  Ceftazidime 0.25 ug/ml (¼ MIC)
  Ceftazidime 0.25 ug/ml+Trehalase 0.092 UI
  Tobramycin 0.06 ug/ml (¼ MIC)
  Tobramycin 0.06 ug/ml+Trehalase 0.092 UI
Parameters Assessed:
  Biofilm mass formation (staining with crystal violet 1%)
  Cells viability (incubation with resazurin)
  Cell growth by colony counting (CFU/mL)

The experimental design in this test for the second strain included:

Strain: *S. aureus* ATCC25923
Temperature: 35±2° C.
Incubation Conditions: Static
Time Points: 24-48 hours preformed biofilm
Treatment: (added to well containing a suspension of *S. aureus* ATCC25923 ~$10^7$ CFU/ml)
Solvent Content: 50% glycerol containing 1% Triton™ X-100 and 25 mM potassium phosphate, pH 6.5
Trehalase Content: 0.092 UI
Antibiotic Concentration:
  Ceftazidime 2 ug/ml (¼ MIC)
  Ceftazidime 2 ug/ml+Trehalase 0.092 UI
  Gentamicin 0.5 ug/ml (¼ MIC)
  Gentamicin 0.5 ug/ml+Trehalase 0.092 UI
Parameters Assessed:
  Biofilm mass formation (staining with crystal violet 0.06%)
  Cells viability (incubation with resazurin)
  Cell growth by colony counting (CFU/mL)

FIGS. 3 and 4 are the tables of the conclusions for these first and second strains.

Another series of tests evaluated the dialyzed trehalase on bacterial growth, viability and biofilm mass in early biofilm (24 hours growth) and early preformed biofilm (preformed for 24 hours) produced by *S. aureus* ATCC25923 (first strain) and *P. aeruginosa* PAO1 (second strain).

The dialysis of trehalase used Amicon® Ultra-15 centrifugal filter devices with the following procedure:

1) Added up to 15 mL of sample (1,600 µL of Trehalase SIGMA+13,400 µL buffer potassium phosphate to the AmiconR Ultra filter device;

2) Placed capped filter device into centrifuge rotor (at 4,000×g; T=4° C.) for 30 minutes;

3) Removed filtrate (bottom) and exchanged buffer suspension (filter device);
4) Repeated steps 2 and 3 twice;
5) As a last step recovered 250 μL of ultrafiltrate Trehalase and re-suspended it with 1,350 μL of buffered suspension to obtain 1,600 μL of dialyzed trehalase; and
6) Read spectrum of bottom filtrate.

As noted before, the dialysis procedure of Sigma Trehalase was introduced by using Amicon Ultra-15 Cenrifugal Filter Device. As a result of this procedure, 1,600 μL of dialyzed trehalase containing 5 UI (International Units of activity) was in buffer solution. This activity was the same as in Sigma Trehalase (1,600 μL, containing solvent) before the dialysis. The preparation of a Trehalase dose of 0.092 UI is used as 0.092 UI/well. The volume of each well was 200 μL and included 100 μL Dialyzed Trehalase (or Trehalase Sigma) and 100 μL of bacterial suspension of P. aeruginosa or S. aureus. To prepare a total volume 1004 of Trehalase (representing 0.092 UI/well), the test used 40 μL of Trehalase (5 UI activity)+60 μL of TSBG (media), so that the activity of Trehaalase was 0.092 UI/100 μL, i.e. 0.92 UI/mL, close to ~1 UI/mL (1 mL=1000 μL).

In these tests, dialyzed (purified) trehalase in a dose 0.92 UI/mL of media, inhibited biofilm formation by S. aureus by 72% in 24 hr-grown biofilm. Sigma Trehalase is sold as a liquid solution of Trehalase (as a proteinous substance in a solvent, but without the amount of protein by weight), only having activity in UIs. In the original tests, the concentration is: =or >0.4 units/mg. One unit will convert 1.0 μmole of trehalose to 2 μmoles of glucose per min at pH 5.7 at 37 A° C. (liberated glucose determined at pH 7.5). This concentration as =or >0.4 units/mg may represent Trehalase enzyme activity as =or >0.4 units in 1 mg of protein (i.e. dry weight of enzyme itself). The original assay: 2.0-6.0 mg/ml protein basis (BCA) in a buffered aqueous glycerol solution. Foreign activity (including a-galactosidase, invertase, a- and β-glucosidase, and amylase) was <or =1%, confirming that this enzyme is highly specific only for degradation of trehalose. The article by Reiko Ishihara et. al., "Molecular cloning, sequencing and expression of cDNA encoding human trehalase", Gene 202 (1997) 69-74), has the specific activity of human trehalase expressed in E. coli, introduced in units/mg of protein (i.e. protein from lysed bacterial cells).

The experimental design for the first strain on the early biofilm included:
Strain: S. aureus ATCC25923
Temperature: 35±2° C.
Incubation Conditions: Static
Time Points: 24 hours
Treatment: (added to well containing a suspension of S. aureus ATCC25923 ~$10^7$ CFU/ml)
Solvent 1: 50% glycerol containing 1% Triton™ X-100 and 25 mM potassium phosphate, pH 6.5
Solvent 2: 25 mM potassium phosphate, pH 6.5
SIGMA Trehalase: 0.092 UI
Dialyzed Trehalase: 0.092 UI
Parameters Assessed:
  Biofilm mass formation (staining with crystal violet 0.06%)
  Cells viability (incubation with resazurin)
  Cell growth by colony counting (CFU/mL)
The experimental design for the first strain on the preformed biofilm included:
Strain: S. aureus ATCC25923
Temperature: 35±2° C.
Incubation Conditions: Static
Time Points: Preformed biofilm for 24 hours, 24 hours of further growth
Treatment: (added to well containing a suspension of S. aureus ATCC25923 ~$10^7$ CFU/ml)
Solvent 1: 50% glycerol containing 1% Triton™ X-100 and 25 mM potassium phosphate, pH 6.5
Solvent 2: 25 mM potassium phosphate, pH 6.5
SIGMA Trehalase: 0.092 UI
Dialyzed Trehalase: 0.092 UI
Parameters Assessed:
  Biofilm mass formation (staining with crystal violet 0.06%)
  Cells viability (incubation with resazurin)
  Cell growth by colony counting (CFU/mL)
The experimental design for the second strain on the early biofilm included:
Strain: P. aeruginosa PAO1
Temperature: 35±2° C.
Incubation Conditions: Static
Time Points: 24 hours
Treatment: (added to well containing a suspension of P. aeruginosa PAO1 ~$10^7$ CFU/ml)
Solvent 1: 50% glycerol containing 1% Triton™ X-100 and 25 mM potassium phosphate, pH 6.5
Solvent 2: 25 mM potassium phosphate, pH 6.5
SIGMA Trehalase: 0.092 UI
Dialyzed Trehalase: 0.092 UI
Parameters Assessed:
  Biofilm mass formation (staining with crystal violet 0.06%)
  Cells viability (incubation with resazurin)
  Cell growth by colony counting (CFU/mL)
The experimental design for the second strain on the preformed biofilm included:
Strain: P. aeruginosa PAO1
Temperature: 35±2° C.
Incubation Conditions: Static
Time Points: Preformed biofilm for 24 hours, 24 hours of further growth
Treatment: (added to well containing a suspension of P. aeruginosa PAO1 ~$10^7$ CFU/ml)
Solvent 1: 50% glycerol containing 1% Triton™ X-100 and 25 mM potassium phosphate, pH 6.5
Solvent 2: 25 mM potassium phosphate, pH 6.5
SIGMA Trehalase: 0.092 UI
Dialyzed Trehalase: 0.092 UI
Parameters Assessed:
  Biofilm mass formation (staining with crystal violet 0.06%)
  Cells viability (incubation with resazurin)
  Cell growth by colony counting (CFU/mL)
FIGS. 5 and 6 are summary tables for the test results of the biofilm produced by S. aureus ATCC25923 (FIG. 5) and the biofilm produced by P. aeruginosa PAO1 (FIG. 6).

Tests were also conducted to explore the dialyzed trehalase potential in gram-positive bacteria (reference strains and clinical isolates). The experiment included:
Step 1: The MIC (Minimum Inhibitory Concentration) activity determination in S. aureus ATCC25923, ATCC33591, and XEN29 in combination with Trehalase; based on the data, ATCC33591 and XEN29 strains were replaced with ATCC35556 and Oxford strains.
Step 2: Evaluate the effect of Trehalase on biofilm formation by different clinical isolates:
Phase 1: Screening of clinical isolates for biofilm formation;
Phase 2: Testing Trehalase on selected clinical isolates.

Step 3: Verify the effect of Trehalase on biofilm growth on Teflon catheter surface:

Phase 1: Effect of Trehalase added during biofilm growth (up to 24 hours);

Phase 2: Effect of Trehalase (added after 24 hours of initial biofilm growth) during the next 24 hours from addition).

The MIC determination with selected *S. aureus* strains proceeded as a first step. The materials and methods included:

*S. aureus* strains: Oxford; ATCC35556 and ATCC25923 (as reference strain)

In vitro assay: MIC in broth (according to CLSI guidelines)

Treatment group (for each strain):
1) Negative control: blank
2) Positive control: bacterial growth
3) Trehalase: bacteria+/−trehalase 0.092 UT
4) Gentamicin: compound+/−trehalase 0.092 UI
5) Vancomycin: compound+/−trehalase 0.092 UI
6) Ciprofloxacin: compound+/−trehalase 0.092 UI Antibiotic concentration: two-fold series dilution from 16 to 0.0078 µg/mL Time-point: 24 hours Incubation: T 37° C.; static condition The results for the MIC determination with selected *S. aureus* strains are shown in FIG. 7. The addition of Trehalase resulted in the MIC value reduction with Gentamicin (up to 16-fold and 33-fold with clinical and reference isolates). No significant effect on Vancomycin and Ciprofloxacin was observed.

The screening of clinical isolates proceeded as a second step (phase 1) and included the following materials and methods:

*S. aureus* strains:
Oxford; PK2; 3226; IH-1018129; ATCCBAA1556; ATCC49230; ATCC35556

*S. aureus* ATCC25923 as the reference strain

Medium: TSB enriched with 1% glucose (TSBG)

In vitro assay format: 96 well-MTP (Microtiter Plate)

Samples: 4 samples for each bacterial strain

Time-point: 24 hours of biofilm growth

Incubation: T 37° C.; static condition

Read-out: Biomass (0.1% safranin staining)

Figure 8:
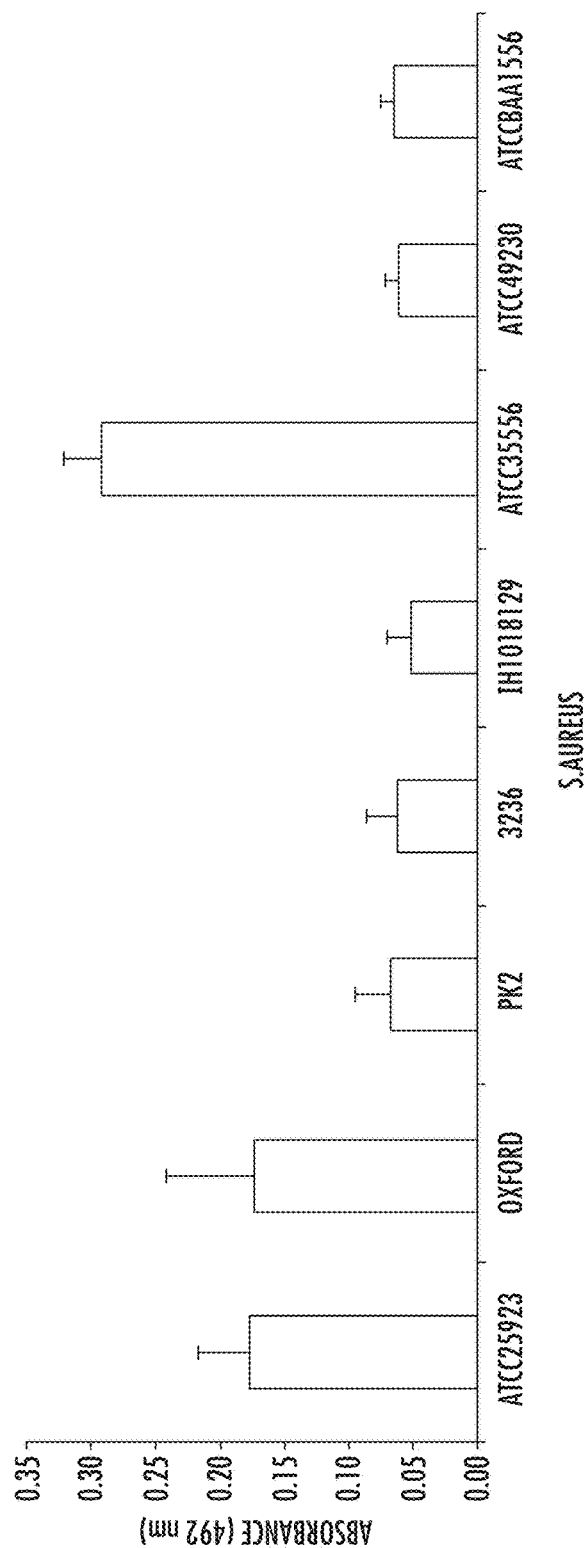
FIG. 8 is a summary table for the results of the screening of clinical isolates in accordance with a non-limiting example.

The results of the screening of clinical isolates are shown in FIG. 8. The *S. aureus* Oxford and ATCC35556 as the strains were selected for the next steps (both MSSA).

In the next phase (phase 2), the testing of the Trehalase on clinical isolates included the following materials and methods:

*S. aureus* strains: Oxford; ATCC35556 and ATCC25923 as the reference strain

Medium: TSB enriched with 1% glucose (TSBG)

In vitro assay format: 96 well-MTP

Treatment Groups (treatment added during the growth of biofilm):

Negative control: blank
Positive control: *S. aureus* strains
Vehicle: *S. aureus* strains+buffer content 25 mM potassium phosphate, pH 6.5
Trehalase: *S. aureus* strains+Trehalase 0.092 UI
Samples: 4 samples for each bacterial strain
Time-point: 24 hours of biofilm growth
Incubation: T 37° C.; static condition
Read-out: Biomass (crystal violet), cell viability (resazurin), planktonic and biofilm bacterial count (agar plating)

The results of the Trehalase testing on clinical isolates are shown in FIGS. 9A, 9B and 9C and FIGS. 10A, 10B and 10C. Overall, the addition of Trehalase during the 24 hours biofilm growth induced a reduction in biomass and viability of selected MSSA strains.

The next step (Step 3) of experiment explored the effect of Trehalase during the 24-hr initial biofilm growth (added at the start of experiment) and after preliminary (24-hr) biofilm growth on catheters. Bacterial biofilm was developed on the catheter segments (14-gauge Teflon intravenous catheter) by incubating individual segments into tubes containing a *S. aureus* Xen 29 suspension in the exponential phase of growth. The bioluminescence signal on catheter segments was detected with the IVIS Lumina image system, and bacterial count CFU/ml for biofilm cells and planktonic cells was evaluated (agar plating). The Step 3—phase 1 explored the effect of Trehalase added during initial biofilm growth (up to 24 hours) and included the following materials and methods:

Bacterial strain: *S. aureus* XEN29 (suspension ~$10^7$ CFU/ml)

Medium: TSB enriched with 1% glucose (TSBG)

In vitro assay: Biofilm formation on catheter (adapted by Kadurugamuwa et al., 2003)

Samples: 3-4 samples for each treatment condition

Treatment:
Negative control: blank (catheter without bacterial suspension)
Positive control: control infection *S. aureus* XEN29 (catheter with bacterial suspension)
Vehicle: *S. aureus* XEN29+buffer content 25 mM potassium phosphate, pH 6.5
Trehalase: *S. aureus* XEN29+Trehalase 0.092 UI
Time-point: Treatment added during the incubation—biofilm growth for 24 hours
Incubation: T 37° C.; static condition
Read-out: Bioluminescence signal and biofilm and planktonic cells bacterial count CFU/ml (agar plating)

The results for exploring the effect of Trehalase added during initial biofilm growth (up to 24 hours) on catheter segments are shown in FIGS. 11A, 11B and 11C. As a second phase, the effect of Trehalase (added after preliminary 24-hr biofilm growth) during the following 24 hours of biofilm growth on catheter segments was explored and used the following materials and methods:

Bacterial strain: *S. aureus* XEN29 (suspension ~$10^7$ CFU/ml)

Medium: TSB enriched with 1% glucose (TSBG)

In vitro assay: Biofilm formation on catheter (adapted by Kadurugamuwa et al., 2003)

Samples: 3-4 samples for each treatment condition

Treatment:
Negative control: blank (catheter without bacterial suspension)
Positive control: control infection *S. aureus* XEN29 (catheter with bacterial suspension)
Vehicle: *S. aureus* XEN29+buffer content 25 mM potassium phosphate, pH 6.5
Trehalase: *S. aureus* XEN29+Trehalase 0.092 UI
Time-point: Treatment added after 24 hours of initial bacterial incubation—biofilm growth for further 24 hours
Incubation: T 37° C.; static condition
Read-out: Bioluminescence signal and biofilm and planktonic cells counting (CFU/ml-agar plating)

FIGS. 12A, 12B and 12C show the results from the testing of Trehalase added after 24 hours biofilm growth (up to 24 hours). The addition of Trehalase at the beginning of experiment (during the initial 24 hours of incubation) induced a significant reduction in biofilm mass and biofilm cells and planktonic cells growth of S. aureus XEN29 on the catheter. There was not as much effect of the Trehalase when added after 24 hours biofilm growth in terms of bioluminescence signal and CFU.

These tests prompted further study and analysis of the use of Trehalase with other antimicrobials and ingredients of potential over-the-counter (OTC) products besides the listed antibiotics. For example, further analysis and study determined that Trehalase may be combined with silver in an effective amount so that the Trehalase operates to break down the biofilm and help the host cells, for example, macrophages, to obtain access to kill the bacteria and eliminate them from the human body together with any accumulated silver. The breakdown of the biofilm with the added Trehalase allows the silver to operate in a more effective manner against infectious pathogens with an absence of toxicity and immunogenicity for humans and animals. It is known that silver exhibits low toxicity in the human body and there is minimal risk due to clinical exposure by inhalation, ingestion and dermal application. It is possible to use colloidal silver preparations and silver sulphadiazine or the more popular silver nitrate. This is especially effective when it can be used as coatings for indwelling catheters and cardiac devices in combination with the Trehalase. With the emergence of antibiotic-resistant strains such as CA-MRSA and HA-MRSA as flesh-eating bacteria, there is renewed interest in using silver as an antibacterial agent and it has been determined from the study that the Trehalase may make the silver even more efficient and effective as an antibacterial agent with the breakdown of biofilm.

The silver source releases silver ions that are effective as an antimicrobial and based on the conformational changes in trans-membrane proteins, the Trehalase helps break down more of the biofilm and parts of the matrix and may ease entry of silver ions into the cell. Different compounds may be used both in medical devices, textiles and in ointments for dermatological applications, including metallic silver that includes nanocrystalline forms in silver coatings. Phosphate silver compounds have moderate ionizing capacity while the silver nitrate has very high ionizing capacity and is commonly used with some dermatological carriers. Silver chloride has low ionizing capability while silver sulfate has a moderate ionizing capability. The sulphadiazine complexes have high ionizing capacity and colloidal silver preparations have moderate to high ionizing capacity. All these compounds may be used in combination with the Trehalase in effective amounts, including ointments, sprays and other applications. Nanochemistry techniques can be used to produce micro-fine silver particles of less than 20 nm diameter with increased solubility and release of silver ions at about 70 to 100 ppm. The disruption produced by the Trehalase facilitates the silver ion interaction. Typically, the ionization of silver metal is proportional to the surface area of a particle that is exposed.

It is possible to use a sustained silver release dressing on a tissue dressing in combination with Trehalase. The silver nitrate should not exceed 1% in contact with living tissue and at 0.5% has been effective in inhibiting P. aeruginosa. In combination with the Trehalase, it is even more effective. Silver sulphadiazine combines the antibiotic properties of silver with sulphonamide and avoids the disadvantage related to silver nitrate and may be used at 1% in a cream base in combination with an effective amount of Trehalase. It may be combined with polyethylene glycol plus poly-2-hydroxyethyl methacrylate, liposomes, poly-L-leucine or even cadaver skin. It may be combined with a lipocolloid formulation such as 1% to 5% silver sulphadiazine at about 0.25 to 0.3% of Trehalase in a non-limiting example and up to 1% or 2%. In a preferred embodiment, it should include 0.5 to 10.0 mg protein per ml based on the BCA (bicinchoninic acid) and dry weight of the enzyme, and with 0.4 units in 1 mg of protein optimal and with the range of 0.2 to 1.0.

In terms of the dressing, the silver could be about less than 10 mg per 100 $cm^2$ to more than 100 mg per 100 $cm^2$ with an effective amount of Trehalase of a similar 0.5 mg to 10 mg/$cm^2$ and with a proper enzyme unit activity. This amount may vary depending on the type of Trehalase. Silver ions may be incorporated into a substance and released slowly with time as with silver sulfadiazine or may come from ionizing the surface of a solid piece of silver as with silver nanoparticles. Although the action is not positive, it is observed that some cells exposed to silver (Ag) ions may have activated a stress response that lead to the condensation of DNA in the center of the cell and there is some cell membrane detachment from the cell wall, cell wall damage and electron dense granules outside and sometimes inside the cell. Thus, the silver may help inactivate proteins by binding the sulfur-containing compounds. Further research and development has observed that the silver in combination with the Trehalase may disrupt the biofilm and provide enhanced structural change to help inactivate proteins even more. This is found to be effective with gram-negative bacteria that may sustain more structural damage than gram-positive bacteria such as E. Coli for the gram-negative bacteria as compared to the gram-positive S. Aureus. The silver may lead to cell shrinkage and dehydration so that in combination with the Trehalase it is even more effective. This makes sense since gram-positive bacteria have a charge of peptidoglycan molecules in the bacterial cell wall and peptidoglycan is negatively charged. Silver ions are positively charged and more silver may get trapped by peptidoglycan. With the enhancement and effectiveness from the added Trehalase degrading the biofilm, this mechanism may trap even more of the silver.

It is known that silver nitrate usually releases its silver ions immediately into solution while silver sulfadiazine gradually releases the majority of its silver ions over an extended period of time, and thus, may provide a more steady supply of silver ions that would be more effective perhaps in a wound cream or bandage. It is possible to use silver salts and other silver components with silver nanoparticles. The nanoparticles may be spherical or rod-shaped and triangular. Different sizes may be used such as 1 ug, 12.5 ug, 50 ug or 100 ug. It is possible that the silver nanoparticles or other silver may be applied to wound dressings and endrotracheal tubes as a coating, including surgical masks. It has been found that cotton fibers are more desirable in some cases.

The amounts of Trehalase can vary but for one possible composition, silver nitrate at 55 ppm may be used in a wound gel and may vary from 50 to 60 ppm in one example and 40 to 60 ppm in yet another example. The gel may include a water-based product with glycerin, carbomer, sodium chloride, silver nitrate and triethanolamine or any or their equivalents. An equivalent amount of Trehalase may be added corresponding to in one example to 0.5 to 10 mg/ml and in yet another example, 0.2 to 0.6 units per mg of protein and for a specific amount, and 0.4 units in 1 mg of protein. The ppm equivalence could be similar to the silver in yet another example. The Trehalase could be 0.5 to 10.0 mg protein/ml. It has also been determined that the silver-killed bacteria may increase the antibacterial activity by the "zombies" effect as noted in the article "Antibacterial Activity of Silver-Killed Bacteria: The "Zombie" Effect," Scientific Reports, 2015, the disclosure which is hereby incorporated by reference in its entirety.

It is possible to use an antimicrobial composition such as disclosed in U.S. Pat. No. 8,568,711, the disclosure which is hereby incorporated by reference in its entirety, and which includes the silver ion and 80% water as a solvent including a hydrophilic polymer where the silver content has the addition of the Trehalase also ranging from 0.0001 to 0.01 milliliter. It should be understood that the activity units are to be acceptable units of USP per milligram.

In one example as a solution, it is possible to use 0.5 to 10 mg/mL on a protein basis for the Trehalase and yet another example in an assay 2.0 to 6.0 mg/ml or about 0.4 units/mg. One unit is defined as the amount of enzyme that may convert 1.0 umol of Trehalose to 2.0 umols of glucose per minute at a pH of about 5.7 at 37 Degrees C. (the liberated glucose is determined at pH 7.5). Its physical form may be contained in 50% glycerol containing 1% Triton X-100 and 25 mM potassium phosphate at a pH of about 6.5. The molecular weight varies but could be about 80,000 Daltons and can range from 70,000 to 85,000 Daltons depending on the origin of the Trehalase in an aspect. One technique that can be used to prepare the Trehalase is described in an article from Yoneyama entitled, "Purification and Properties of Detergent-Solubilized Pig Kidney Trehalase," Archives of Biochemistry and Biophysics (1987), the disclosure which is hereby incorporated by reference in its entirety.

It is possible that Trehalase as alpha, alpha-trehalase, EC 3.2.1.28 could be solubilized from the brush border membrane of pig kidney cortex by Triton X-100 and sodium deoxycholate in the presence of inhibitors of proteolytic enzymes. In this example, the kidney enzyme can be purified 3060-fold using gel filtration, ion exchange chromatography, Con A-Sepharose chromatography, phenyl-Sepharose CL-4B hydrophobic interaction chromatography. Contaminant proteins can be absorbed as described in the article with 99% or greater purity based on amino-terminal amino acid analysis. This purified enzyme in this example had a specific activity of 278 units/mg protein, a molecular weight of about 80,000 on sodium dodecyl sulfate-polyacrylamide gel electrophoresis. It is a glycoprotein and contained 2 mol of glucosamine per mole of trehalase. The apparent Km for this trehalase was calculated to be 2.1 mM. This type of produced kidney trehalase was highly specific for trehalose and exhibited an optimal pH of 5.9, and an isoelectric point is between about pH 4.7 and 4.4. Other details may be found in the incorporated by reference article.

The Trehalase may also be combined with chlorhexidine gluconate or an equivalent both as an antiseptic skin cleanser and as in an oral rinse. In one example, the chlorhexidine gluconate is about 0.12% and in an oral rinse and may be used 3 to 4 times daily. The Trehalase may be added in units as noted before and in a percentage if used for labeling at about 0.1% to 0.3% and in yet another example, 0.1% to 0.5% and up to 1% to 2% in yet another example. It has been found that a small amount is effective to aid in an oral rinse for potential applications and to help in breaking down some biofilm to make the chlorhexidine gluconate more effective. As an antiseptic skin cleanser, great amounts of the Trehalase may be used and the higher end range closer to 50 to 100 mg protein/ml and up to 1% to 7% and in another example about 4% in combination with 4% solution chlorhexidine gluconate. This use of the oral cleaner and skin cleanser is excellent for the extremely-drug-resistant (XDR) strains of *Klebsiella pneumoniae* that may have reduced susceptibility to chlorhexidine and with the added Trehalase, allows the chlorhexidine to be more effective since the added Trehalase helps break apart the biofilm to allow more effective chlorhexidine.

It is possible to use another decolonization measure such as mupirocin to prevent *Staphylococcus aureus* skin and soft tissue infections (SSTI). It is also possible to use it on the *Acinetobacter baylyi* adp1. It may be used in a water-based solution in one example and for a skin cleanser could be mixed with an alcohol-based solution of 70% or a water-based solution that may include other components such as some glycol. The incorporation of about 2 weight percent and 3 weight percent chlorhexidine in combination with a 1 to 4 weight percent Trehalase at an effective enzyme activity is believed to be effective at that range for the antiseptic skin cleanser. Concentrations may be about or greater than 1 μg/ml and in some applications, concentrations up to 10 or even greater than 73 μg/ml in some cases as a wipe with Trehalase.

In one example, it is possible to use 4% w/w for chlorhexidine gluconate and alcohol at 4% w/w in water with a similar preparation of the Trehalase. Another possible application is with denture cleaning tablets that includes a number of components such as a mild bleach, for example, dilute sodium hypochlorite and may include other ingredients such as sodium bicarbonate to alkalize the water and may include citric acid to help remove stains and sodium perborate, sodium polyphosphate, and potassium monopersulfate as a cleaning and bleaching agent and EDTA. As a percent w/w, it may be added to about 1% to 5% for the Trehalase. It can be added but at an effective 0.5 to 10 mg protein per ml, and about 0.2 to 1.0 units in a milligram (mg) of protein based on a dry weight basis, and in an example, 0.4 units/mg. An example of some the components that may be included with Trehalase include the following:

| Chemical Name | Proportion (% w/w) |
|---|---|
| Potassium peroxymonosulfate sulfate | <10 |
| Sodium carbonate peroxide | 10-<30 |
| Sodium carbonate | 10-<30 |
| Citric acid | 10-<30 |
| Malic acid | <10 |
| Other ingredients classified as not hazardous according to NOHSC | to 100 |

It is possible to include Trehalase in mouthwashes, toothpastes, and cement material for dental applications where the Trehalase is combined with chlorhexidine (as the antimicrobial), or with essential oils (or their active fractions). For example, some mouthwashes may include Chlorhexidine Digluconate at 0.06% w/v and Sodium Fluoride (250 ppm fluoride) and include the added Trehalase in an amount equivalent to the optimal doses similar to that added to other compositions and treatments discussed above. Another example is a mouthwash that may contain as active ingredients Eucalyptol at 0.092%; Menthol at 0.042%; Thymol at 0.064%, (these are active antimicrobial fractions of essential oils) and Methylsalicylate at 0.060%. These components may be labeled together on the bottle as Antiplaque/antigingivitis. Another type of mouthwash contains as active ingredient Sodium fluoride 0.02% (0.01% w/v fluoride ion) along with all ingredients from the first type (but without their doses, just mentioned as inactive ingredients). Trehalase can be added to all three mouthwashes in amount equivalent to the "optimal" doses noted above. Trehalase may be added to a toothpaste, for example, a type having an active ingredient as Sodium fluoride at 0.310% w/w (1400 ppm fluoride), or another toothpaste that has active ingredients such as Sodium fluoride at 0.24% (0.15% w/v fluoride ion) and Triclosan at 0.30%, as antigingivitis, i.e., antimicrobial.

As noted before, silver and the Trehalase is effective and it has also been found that copper is effective. Hospital environments may act as a reservoir for biofilm-forming pathogens that cause healthcare-associated infections (HCAIs), so that approaches to reducing environmental microbial contamination in addition to cleaning, attracted attention over the last decade. Copper is well recognized as a powerful antimicrobial with rapid broad spectrum efficacy against bacteria, viruses and fungi. In a novel cross-over study in an acute medical ward, a toilet seat, a set of tap handles and a ward entrance door push plate, each containing copper, were sampled for the presence of microorganisms and compared to equivalent standard, non-copper-containing items on the same ward, demonstrating a statistically significant decrease of microbial contamination on copper-covered surfaces (A. L. Casey, D. Adams, T. J. Karpanen, et.al. "Role of Copper in reducing hospital environment contamination", The Journal of Hospital Infection, Vol. 74, Issue 1, pages 72-77 (January 2010).

Extensive scientific information on the role of Antimicrobial Copper in reducing transmission of infection and spread of antimicrobial resistance is introduced in "Scientific References" (http://www.antimicrobialcopper.org/uk/antimicrobial-resistance) in multiple laboratory tests carried out under typical indoor conditions, it was demonstrated that "antimicrobial copper" was effective against many pathogens, including those with drug-resistance: MRSA *S. aureus*, MDR Tubercle *bacillus*, MDR *Acinetobacter baumannii*, Vancomycin-resistant *enterococcus* (VRE), Carbapenem-resistant Enterobacteriaceae (CRE), ESBL-producing *Klebsiella pneumoniae*, ESBL-producing *E. coli*.

This efficacy translates into the clinical environment, as demonstrated in a multi-center ICU trial in the US (M G Schmidt, H H Attaway, P A Sharpe, et. al., "Sustained Reduction of Microbial Burden on Common Hospital Surfaces through Introduction of Copper", Journal of Clinical Microbiology 2012, Vol. 50 No. 7 2217-2223). Six near-patient surfaces were upgraded to copper, and sampling was undertaken weekly over a period of 23 months. Over the intervention period, the combined MRSA and VRE burdens were 96.8% lower on copper surfaces than on comparable plastic, wood, metal, and painted surfaces and were 98.8% lower on the bed rails, the most heavily burdened object. In this US trial, the bioburden reduction was associated with a 58% reduction in infections (C D Salgado, K A Sepkowitz, J F John, J R Cantey, H H Attaway, K D Freeman, M G Schmidt, "Copper Surfaces Reduce the Rate of Healthcare-Acquired Infections in the Intensive Care Unit", Infection Control and Hospital Epidemiology 2013, 34(5), 479-486).

The enzyme Trehalase can be immobilized on the copper-containing surfaces to prevent microbial biofilm formation by microorganisms accumulated on such surfaces during the time periods between the cleaning procedures (frequency of cleaning such surfaces is usually introduced in guidelines for maintenance of such surfaces). The enzyme Trehalase can also be included in disinfecting solutions for such cleaning procedures (as described in previous embodiments for prevention and treatment of biofilm-based infections on medical devices and medical equipment surfaces).

Waterborne infections contribute to transmission of infections in hospital settings, in particular when used in medical equipment (surgical instruments, endoscope washer-disinfectors, nebulizers, endotracheal tubes) disinfection procedures. For example, surgical instruments may have high post-cleaning levels of carbohydrates (up to 352 $\mu g/cm^2$) and endotoxin (up to 25 373 $EU/cm^2$), suggesting unrecognized issues with the quality of water used for the final rinse, and showing the necessity to monitor the water quality used in instrument washers (M. J. Alfa, N Olson, A Al-Fadhaly, "Cleaning efficacy of medical device washer in North American healthcare facilities", The Journal of Hospital Infection, Vol. 74, Issue 2, Pages 168-177 (February 2010). The development of microbial biofilm in washer-disinfectors, the type of biofilms and the nature of the bacteria within them, along with increasing antimicrobial resistance in those pathogens is of a major concern (W. G. MacKay, A. T. Leanord, C. L. Williams, "Water, water everywhere nor any of a sterile drop to rinse your endoscope", The Journal of Hospital Infection, Vol. 51, Issue 4, pages 256-261 (August 2002). Growing resistance of HCAIs to antimicrobials and biocides is on the rise. Various biocides show a wide range of their efficacy. For example, in a comparative study on polytetrafluoroethylene (PTFE) tubes, contaminated by a liquid medium inoculated with *Pseudomonas aeruginosa*, using five different alternative disinfectant solutions: two peracetic acid solutions (with and without an activator), glutaraldehyde, orthophthaldehyde and succine dialdehyde, it was shown that repeated treatments of a PTFE tube with a 2% glutaraldehyde solution induced an important accumulation and/or fixation of protein, compared to peracetic-acid-based disinfectants, for which the accumulation and/or fixation of protein remained low, but varied from one formulation to another (L. Pineau, C. Desbuquois, B. Marchetti, D. Luu Duck, "Comparison of the fixative properties of five disinfectant solutions", The Journal of Hospital Infection, Vol. 68, Issue 2, Pages 171-177 (February 2008).

In this context again, the enzyme Trehalase can be included in various formulations of disinfection solutions, and can be used as directed in the previous embodiments for composition and methods for treatment of biofilm-based infections on medical devices.

It should be understood that the copper may operate to short circuit the current in the cell membrane to disturb the "trans membrane potential" and can cause oxidative damage and thus, "punch" a hole in the bacterium. It is possible to add Trehalase to Medicinal Copper, and even possible to apply Trehalase and copper in a spray as an adhesive and spray it onto surfaces. Besides copper, it is also possible to use Trehalase in combination with biofilm disrupters such as xylitol, lactoferrin, and D-amino acids. Xylitol is a sugar alcohol used as a sweetener.

The bacterial biofilms are the major contributing factors to chronic wounds, such as diabetic foot ulcers, pressure ulcers, and venous leg ulcers, providing increased bioburden to the wounds and interfering with the healing process. Traditional methods of treatment have proven ineffective, therefore therapy of non-healing wounds demands biofilm-targeted strategies.

Studies using a colony-drip-flow reactor biofilm model, demonstrated positive result of the combined treatment of bacterial biofilms with the innate immune molecule lactoferrin and the rare sugar-alcohol xylitol against a clinical wound isolate; for both a single species biofilm and a dual species biofilm, the lactoferrin/xylitol hydrogel in combination with the silver wound dressing Acticoat™ had a statistically significant reduction in biofilm cell viability compared to the commercially available wound hydrogel (Ammons M C, Ward L S, James G A, "Anti-biofilm efficacy of a lactoferrin/xylitol wound hydrogel used in combination with silver wound dressings", Int Wound J, 2011 June 8(3); 268-73). In an in vitro biofilm model with a clinical isolate of *P. aeruginosa*, subjected to treatment with either lactoferrin or xylitol alone or in combination, it was shown that combined lactoferrin and xylitol treatment disrupted the structure of the *P. aeruginosa* biofilm and resulted in a >2 log reduction in biofilm cell viability; in situ analysis indicated that xylitol appeared to disrupt the biofilm structure and lactoferrin increased the permeability of bacterial cells (Ammons M C, Ward L S, Fisher S T, Wolcott R D, James G A, "In vitro susceptibility of established biofilms composed of a clinical wound isolate of *Pseudomonas aeruginosa* treated with lactoferrin and xylitol", Int J Antimicrob Agents, 2009 March, 33(3):230-6).

As noted before, the enzyme trehalase can be used in combination with antimicrobials (ex, silver gel or silver-based wound dressings) for chronic wounds treatment along with other antimicrobials, or can be used in combination with lactoferrin or lactoferrin/xylitol to increase effectiveness of these treatment modalities. As further noted before, to increase the healing process of such chronic wounds, trehalase in combination with antimicrobials can be used along with antioxidants, anti-inflammatory and immune-modulating substances. Trehalase may be added in the preparation and amounts disclosed previously.

In many cases, chronic wounds have tendency to be additionally contaminated by Gram-positive pathogens, such as *S. aureus* and *Streptococci* spp. that contribute to increased bioburden in mixed species biofilms. In these cases, Trehalase in combination with polymicrobial antibiotics and/or natural antimicrobials (i.e., silver compounds as noted before) can provide dual effect, targeting the biofilm structure and reducing viability of biofilm-forming pathogens (including both biofilm-embedded cells and dispersed planktonic cells).

It is also possible to add units of Trehalase enzyme to an antibiotic ointment that may include one or more of bacitracin zinc, neomycin sulfate that may be equivalent to a neomycin base and a polymyxin B sulfate. Although the amounts can vary in one example, 300 to 500 units of a bacitracin zinc may be added to 2.5 to 4.5 mg of the neomycin base and 4,000 to 6,000 polymyxin B units added as the polymyxin B sulfate together with units of Trehalase with sufficient units of activity and in one example, 0.2 to 1.0 units per mg and around 0.4 units per milligram.

A sufficient amount of Trehalase may be added to an enzyme supplement that could include protease as either 4.5, 6.0 and/or 3.0 such as respective amounts of 14,000 to 23,000 HUT for the protease 4.5, 2,000 to 4,000 HUT for the protease 6.0, and 13 to 19 SAPU for protease 3.0 and in specific amounts about 19,000; 3,000; and 16. About 3,000 to 5,000 DU of amylase may be added and in a specific amount 4,200, and 7 to 13 AGU of glucoamylase and in a specific amount 10 AGU, 20 to 28 LU of lipase and in a specific amount 24 LU. 90 to 150 CU of cellulase may be added (specific 120 CU) and 180 to 260 SU of invertase (specific amount 220 SU), and 500 to 600 DP for malt diastase (specific 550 DP). There may also be included about 80 to 120 GALU (100 GALU) for alpha-galactosidase and 1,600 to 2,400 HUT of peptidase (specific amount 2,000 HUT). Many of these quantities can vary and be supplemented with other enzymes depending on the end use desired. The Trehalase can be supplemented in an effective amount of 0.2 to 1.0 unit in 1 mg of protein. It may also be added with probiotics such as a blend of *Lactobacillus acidophilus* and *biphobacterium lactis* such as around 4 billion for the probiotic in one non-limiting example.

It is also possible to combine the Trehalase with antimicrobial peptides that may be an alternative to small molecule antibiotics, including modifications of short antimicrobial peptides. This could include lipopeptides and a combination of fatty acids with cationic antimicrobial peptides that help change the confirmation of the antimicrobial peptides secondary structure in the presence of bacterial membranes.

It is possible assay Trehalase based on the technique described in Dahlquist, A., (Assay of Intestinal Disaccharidases Analytical Biochemistry (1968)). An enzymatic assay of Trehalase has been formulated as (EC 3.2.1.28) by Sigma-Andrich.

Principle: Trehalose+$H_2O$ $\xrightarrow{Trehalase}$ 2 Glucose

Conditions: T=37° C., pH=5.7, $A_{340\ nm}$, Light path=1 cm

Method: Spectrophotometric Stop Rate Determination

The Reagents in this assay include:

A. 135 mM Citric Acid Buffer, pH 5.7 at 37° C., which is prepared 100 ml in deionized water using Citric Acid, Free Acid, Monohydrate, as Sigma Prod. No. C-7129, corresponding to the citric acid monohydrate. It is adjusted to pH 5.7 at 37 C with 1 M NaOH.

B. 140 mM D-Trehalose Solution, which is prepared by 10 ml in Reagent A using D(+)Trehalose, Dihydrate, as Sigma Prod. No. T-5251 corresponding to D-(+)-Trehalose dehydrate C. 500 mM Tris Buffer, pH 7.5 at 37° C., which is prepared by 100 ml in deionized water using Trizma Base, as Sigma Prod. No. T-1503. It is adjusted to pH 7.5 at 37 C with 1 M HCl.

D. Trehalase Enzyme Solution. Immediately before use, prepare a solution containing 0.1-0.3 unit/ml of Trehalase in cold Reagent A.

E. Glucose Determination Vial. It is possible to use an ion exchange type as Sigma Stock No. 16-10 (Mono QHR 16/10), Glucose (HK) 10 Reagent. The contents are dissolved in 10 ml of deionized water.

Procedure:

Step 1: Pipette (in milliliters) the following reagents into suitable cuvettes:

|  | Test | Blank |
| --- | --- | --- |
| Reagent A (Citrate Buffer) | 0.3 | 0.3 |
| Reagent D (Enzyme Solution) | 0.1 | 0.1 |

Mix by inversion and equilibrate to 37° C. using a suitably thermostatted spectrophotometer. Then add:

|  |  |  |
| --- | --- | --- |
| Reagent B (D-Trehalose) | 0.1 | — |

Immediately mix by inversion and incubate at 37° C. for exactly 15 minutes. Then add:

|  |  |  |
| --- | --- | --- |
| Reagent C (Tris Buffer) | 0.5 | 0.5 |
| Reagent B (D-Trehalose) | — | 0.1 |

Step 2: Pipette (in milliliters) the following reagents into suitable cuvettes:

|  | Test | Blank |
| --- | --- | --- |
| Reagent E (16-10) | 3.0 | 3.0 |

Equilibrate to 37° C. Monitor the $A_{340nm}$ until constant, using a suitably thermostatted spectrophotometer. Record the initial $A_{340nm}$ for both Test and Blank. Then add:

|  |  |  |
| --- | --- | --- |
| Test Solution | 0.1 | — |
| Blank Solution | — | 0.1 |

Immediately mix by inversion and record the increase in $A_{340nm}$ until complete (approximately 5 minutes). Obtain the final $A_{340nm}$ for both the Test and Blank.
Calculations:

$$\Delta A_{340nm}\ Test = A_{340nm}\ Test\ Final - A_{340nm}\ Test\ Initial$$

$$\Delta A_{340nm}\ Blank = A_{340nm}\ Blank\ Final - A_{340nm}\ Blank\ Initial$$

$$\text{Units/ml enzyme} = (\Delta A_{340nm}\ Test - A_{340nm}\ Blank)(1.0)(3.1)/(6.22)(2)(15)(0.1)(0.1)$$

6.22=Millimolar extinction coefficient of β-NADH at 340 nm
2=Number of Glucose molecules per molecule of Trehalose
15=Reaction time (in minutes) of Step 1
1.0=Final volume (in milliliters) of Step 1
3.1=Final volume (in milliliters) of Step 2
0.1=Volume From Step 1 used in Step 2
0.1=Volume (in milliliters) of enzyme used
Units/mg protein=units/ml enzyme/mg protein/ml enzyme
Unit Definition:

One unit will convert 1.0 μmole of trehalose to 2.0 μmoles of glucose per minute at pH 5.7 at 37° C. (liberated glucose determined at pH 7.5).
Final Assay Concentration:

In a 0.50 ml reaction mix, the final concentrations are 135 mM citric acid, 28 mM D-trehalose, and 0.01-0.03 unit of trehalase.

The previous description of the disclosed embodiments is provided to enable any person skilled in the art to make or use the disclosed embodiments. Various modifications to these embodiments will be readily apparent to those skilled in the art, and the principles defined herein may be applied to other embodiments without departing from the scope of the disclosure. Thus, the present disclosure is not intended to be limited to the embodiments shown herein but is to be accorded the widest scope possible consistent with the principles and novel features as defined by the following claims.

That which is claimed is:

1. A method of reducing growth of biofilm mass and biofilm cells on a catheter resulting from *Staphylococcus aureus* bacteria, comprising:
    providing a catheter that has no biofilm growth resulting from *S. aureus* bacteria on the catheter; and
    adding onto the catheter a composition as a solution comprising trehalase, wherein the trehalase comprises about 0.05%-5% by weight of the composition and the trehalase is derived from a mammalian or plant source wherein biofilm mass and biofilm cell growth by *S. aureus* on the catheter is reduced.

2. The method of claim 1, wherein the adding comprises immersing the catheter within the composition as the solution comprising trehalase.

3. The method of claim 1, further comprising adding silver into the composition, wherein the silver comprises silver particles of less than 20 nanometer diameter that are about 1% to about 5% by weight of the composition.

4. The method of claim 1, wherein said trehalase comprises 0.5 mg to 10.0 mg per milliliter on a protein basis of the composition.

5. The method of claim 1, wherein the composition further comprises compounds selected from the group consisting of saccharidases, proteolytic enzymes, fibrinolytic enzymes, lipolytic enzymes, or any combination thereof.

6. The method according to claim 1, wherein the composition includes an antibiotic selected from the group consisting of Ceftazidime, Gentamicin, Tobramycin, Vancomycin, and Ciprofloxacin.

7. The method according to claim 6, wherein the antibiotic comprise Gentamicin.

8. The method according to claim 1, wherein the solution comprises an aqueous or saline solution.

9. The method according to claim 1, wherein the composition as a solution includes a delayed-release coating added onto the catheter.

10. The method according to claim 1, further comprising adding the composition as a solution onto the interior lumen surface of the catheter.

* * * * *

UNITED STATES PATENT AND TRADEMARK OFFICE
CERTIFICATE OF CORRECTION

PATENT NO. : 10,420,822 B2
APPLICATION NO. : 15/632618
DATED : September 24, 2019
INVENTOR(S) : Ivanova et al.

It is certified that error appears in the above-identified patent and that said Letters Patent is hereby corrected as shown below:

On the Title Page

Item (72) Inventors: Delete:
"Thomas K. Connellan, Charlottesville, FL (US)"
Substitute:
-- Thomas K. Connellan, Charlottesville, VA (US) --

Signed and Sealed this
Nineteenth Day of November, 2019

Andrei Iancu
*Director of the United States Patent and Trademark Office*